US006933366B2

(12) United States Patent
Sallberg et al.

(10) Patent No.: US 6,933,366 B2
(45) Date of Patent: *Aug. 23, 2005

(54) SPECIFICITY EXCHANGERS THAT REDIRECT ANTIBODIES TO BACTERIAL ADHESION RECEPTORS

(75) Inventors: Matti Sallberg, Alvsjo (SE); Jan-Ingmar Flock, Bromma (SE)

(73) Assignee: Tripep AB, Huddinge (SE)

( * ) Notice: Subject to any disclaimer, the term of this patent is extended or adjusted under 35 U.S.C. 154(b) by 147 days.

This patent is subject to a terminal disclaimer.

(21) Appl. No.: 10/372,735

(22) Filed: Feb. 21, 2003

(65) Prior Publication Data

US 2003/0225251 A1 Dec. 4, 2003

Related U.S. Application Data

(63) Continuation-in-part of application No. 10/234,579, filed on Aug. 30, 2002, which is a continuation of application No. 09/839,666, filed on Apr. 19, 2001, now Pat. No. 6,469,143, which is a continuation of application No. 09/532,106, filed on Mar. 21, 2000, now Pat. No. 6,245,895, which is a continuation of application No. 09/246,258, filed on Feb. 8, 1999, now Pat. No. 6,040,137, which is a continuation of application No. 08/737,085, filed as application No. PCT/SE95/00468 on Apr. 27, 1995, now Pat. No. 5,869,232, application No. 10/372,735, which is a continuation-in-part of application No. 09/664,945, filed on Sep. 19, 2000, now Pat. No. 6,660,842, and a continuation-in-part of application No. 09/664,025, filed on Sep. 19, 2000, now abandoned, application No. 10/372,735, which is a continuation-in-part of application No. PCT/IB01/02327, filed on Sep. 19, 2001, application No. 10/372,735, which is a continuation-in-part of application No. 10/153,271, filed on May 21, 2002, now abandoned, which is a division of application No. 09/556,605, filed on Apr. 21, 2000, now Pat. No. 6,417,324, application No. 10/372,735, which is a continuation-in-part of application No. 09/839,447, filed on Apr. 20, 2001, now abandoned, which is a continuation-in-part of application No. 09/556,605, filed on Apr. 21, 2000, now Pat. No. 6,417,324.

(51) Int. Cl.[7] ............................................. C07K 1/00
(52) U.S. Cl. ..................... 530/350; 530/324; 530/325; 530/326; 530/327; 530/328; 530/329; 530/330
(58) Field of Search ..................... 435/5; 530/324–330, 530/350

(56) References Cited

U.S. PATENT DOCUMENTS

| | | |
|---|---|---|
| 4,169,138 A | 9/1979 | Jonsson |
| 4,376,110 A | 3/1983 | David et al. |
| 4,471,058 A | 9/1984 | Smith et al. |
| 4,486,530 A | 12/1984 | David et al. |
| 4,589,881 A | 5/1986 | Pierschbacher et al. |
| 4,946,778 A | 8/1990 | Ladner et al. |
| 5,091,513 A | 2/1992 | Huston et al. |
| 5,175,096 A | 12/1992 | Hook et al. |
| 5,189,015 A | 2/1993 | Hook et al. |
| 5,196,510 A | 3/1993 | Rodwell et al. |
| 5,260,189 A | 11/1993 | Formoso et al. |
| 5,320,951 A | 6/1994 | Hook et al. |
| 5,416,021 A | 5/1995 | Hook et al. |
| 5,440,014 A | 8/1995 | Hook et al. |
| 5,561,049 A | 10/1996 | Vold et al. |
| 5,571,511 A | 11/1996 | Fischer |
| 5,571,514 A | 11/1996 | Hook et al. |
| 5,582,975 A | 12/1996 | Milliman |
| 5,601,830 A | 2/1997 | Su et al. |
| 5,627,263 A | 5/1997 | Ruoslahti et al. |
| 5,652,217 A | 7/1997 | Hook et al. |
| 5,700,928 A | 12/1997 | Hodgson et al. |
| 5,766,857 A | 6/1998 | Ruoslahti et al. |
| 5,766,951 A | 6/1998 | Brown |
| 5,770,208 A | 6/1998 | Fattom et al. |
| 5,770,702 A | 6/1998 | Hook et al. |
| 5,776,712 A | 7/1998 | Kuusela et al. |
| 5,789,549 A | 8/1998 | Hook et al. |
| 5,840,846 A | 11/1998 | Hook et al. |
| 5,843,774 A | 12/1998 | Ginsberg |
| 5,846,536 A | 12/1998 | Bissell et al. |
| 5,866,541 A | 2/1999 | Hook et al. |
| 5,869,232 A  * | 2/1999 | Sallberg ........................ 435/5 |
| 5,888,738 A | 3/1999 | Hendry |
| 5,929,220 A | 7/1999 | Tong et al. |
| 5,939,273 A | 8/1999 | Lussow et al. |
| 5,942,606 A | 8/1999 | Lal et al. |
| 5,955,078 A | 9/1999 | Burnham et al. |
| 5,980,908 A | 11/1999 | Hook et al. |
| 5,981,274 A | 11/1999 | Tyrell et al. |
| 6,008,341 A | 12/1999 | Foster et al. |
| 6,030,613 A | 2/2000 | Blumberg et al. ........ 424/134.1 |
| 6,040,137 A  * | 3/2000 | Sallberg ........................ 435/5 |
| 6,066,648 A | 5/2000 | Duggan et al. |
| 6,077,677 A | 6/2000 | Hodgson et al. |

(Continued)

FOREIGN PATENT DOCUMENTS

| | | |
|---|---|---|
| EP | 0 182 546 A2 | 5/1986 |
| EP | 0 508 427 A | 10/1992 |
| WO | WO 93/15210 | 8/1993 |
| WO | WO 93/17044 | 9/1993 |
| WO | WO 94/13804 | 6/1994 |

(Continued)

OTHER PUBLICATIONS

Leibiger et al. (1998) Structural characterization of the oligosaccharides of a human monoclonal anti–lipopolyssaccharide immunoglobulin M. Glycobiology. 8(5):497–507.

(Continued)

Primary Examiner—Jeffrey Stucker
(74) Attorney, Agent, or Firm—Knobbe, Martens, Olson & Bear, LLP

(57) ABSTRACT

Specificity exchangers and methods of making and using specificity exchangers are disclosed. Specificity exchangers are useful for preventing and treating human diseases including cancer and those resulting from pathogens such as bacteria, yeast, parasites, fungus, viruses, and the like. More specifically, specificity exchangers can redirect existing antibodies in a subject to pathogens and cancer cells.

19 Claims, No Drawings

U.S. PATENT DOCUMENTS

| | | | |
|---|---|---|---|
| 6,086,875 A | 7/2000 | Blumberg et al. | 424/134.1 |
| 6,086,895 A | 7/2000 | Hook et al. | |
| 6,087,330 A | 7/2000 | Kogan et al. | |
| 6,090,388 A | 7/2000 | Wang | |
| 6,090,944 A | 7/2000 | Hutchinson | |
| 6,093,539 A | 7/2000 | Maddon et al. | |
| 6,245,985 B1 | 6/2001 | Sasaki et al. | |
| 6,417,324 B1 | 7/2002 | Sällberg | |
| 6,469,143 B2 * | 10/2002 | Sallberg | 530/350 |
| 6,485,726 B1 | 11/2002 | Blumberg et al. | 424/178.1 |
| 6,660,842 B1 * | 12/2003 | Sallberg | 530/350 |
| 2002/0025513 A1 | 2/2002 | Sällberg | |
| 2002/0058247 A1 | 5/2002 | Sällberg | |
| 2003/0021789 A1 | 1/2003 | Xu et al. | 424/164.1 |
| 2003/0044418 A1 | 3/2003 | Davis et al. | 424/184.1 |

FOREIGN PATENT DOCUMENTS

| | | |
|---|---|---|
| WO | WO 95/08577 | 3/1995 |
| WO | WO 95 29938 | 11/1995 |
| WO | WO 95/29938 | 11/1995 |
| WO | WO 98/03543 | 1/1998 |
| WO | WO 98/31389 | 7/1998 |
| WO | WO 98/43677 | 10/1998 |
| WO | WO 99/27109 | 6/1999 |
| WO | WO 99 61041 A | 12/1999 |
| WO | WO 00 26385 A | 5/2000 |
| WO | WO 95 22249 A | 5/2000 |
| WO | WO 00/66621 | 11/2000 |
| WO | WO 01/82546 | of 2001 |
| WO | WO 01/81421 | 11/2001 |
| WO | WO 02/24887 | 3/2002 |

OTHER PUBLICATIONS

Lin et al. (1998) Differential recognition by proteins of α–galactosyl residues on endothelial cell surfaces. Glycobiology. 8(5):433–443.

Mizukami et al. (1988) Binding region for human immunodeficiency virus (HIV) and epitopes for HIV–blocking monoclonal antibodies of the CD4 molecule defined by site–directed mutagenesis. Proc. Natl. Acad. Sci. 85:9273–9277.

E. Bianchi et al., "The Making of the Minibody: An Engineered Beta–Proten for the Display of Conformationally Constrained Peptides," *Journal of Molecular Recognition,* 7(1):9–24 (1994).

Database Genseq 'Online! Oct. 21, 1991, Asahi Chemical Ind. KK: "L–chain variable region of plasminogen activator antibody" XP002183673, Accession AAP61027 (published in JP11729000).

Database Genseq 'Online! Jan. 8, 1993, Clonatec SA: "Hepatitis B irus HBc antigen II," XP002183674, Accession AAR25272 (published in EP494825).

Database Genseq 'Online! Jul. 1, 1993, Cytel Corp: "Cytotoxic T–lymphocyte inducing peptide 802.03." XP002183675, Accession AAR33488.

Database WPI, Section Ch., Week 199713, Derwent Publications Ltd., London, GB: Class B04, AN 1997–140911, XP002183678 & JP 09 020798 A (Asahi Kasei Kogyo KK) Jan. 21, 1997, abstract.

Database Patent_PRT 'Online! Mar. 21, 2001, Eurodiagnostica AB: "Sequence 9 from Patent W)0116163" XP002183677, Accession AX 090806.

Database Genseq 'Online! Jul. 31, 2000, Yeda Res & Dev Co Ltd: "Murine anti–Pab–421 IDI–1 mAb heavy chain CDR based Peptide IDI–H1", XP002183676, Accession AAY70799 (published in WO0023082).

Ganem, "Hepadnaviridae and their replication," *Fields Virology,* Third Ed., pp. 2703–2705 (1996).

GenCore Sequence Alignment of Sequence ID No: 16 with the L–chain variable region of plasminogen activator antibody of JP61172900–A, Ashi Chemical Ind. KK. (Apr. 8, 1986) ID No: p. 61027.

Grabowska et al., "Identification of type–specific domains within glycoprotein G of herpes simplex virus type 2 (HSV–2) recognized by the majority of patients infected with HSV–2, but not by those infected with HSV–1," *Journal of General Virology,* 80(pt.7):1789–1798 (1999).

Greenspan et al., Nature Biotechnology, 7:936–937 (1999).

Korba and Gerin, "Generation of a large combinatorial library of immunoglobulin repertoire in Phage Lambda," Science, 256:1275–1281 (1989).

Korba and Milman, "A cell culture assay for compounds which inhibit hepatitis B virus repolication," Antiviral Res, 15(3):217–228 (1991).

Lazdina et al., Journal of Virology, 75(14):6367–6374 (2001).

Machida et al., "Antigenic sites on the arginine–rich carboxyl–terminal doman of the capsid protein of hepatitis B virus distinct form hepatitis B core or e antigen," Mol. Immunol. 26(4):421–431 (1989).

McDevvit et al., "Identification of the ligand–binding domain of the surface–located fibrinogen receptor (clumping factor) of *Staphylococcus aureus,*" Molecular Microbiology, vol. 16, No. 5, pp. 895–907 (1995).

Milich et al., "The humoral immune response in acute and chronic hepatitis B virus infection," *Springer Semin. Immunopathol.,* 17:149–166 (1995).

Milich et al, "The Nucleocapsid of Hepatitis B Virus is both a T–Cell–Independent Antigen," Science, 234:1398–1401 (1986).

Milich et al., "Role of B cells in antigen presentation of the hepatitis B core," *Proc. Natl. Acad. Sci. USA,* 94:14648–14653 (1997).

Prange et al., Journal of Biological Chemistry, 380(3):305–314 (1999).

Salfeld et al., "Antigenic determinants an dfunctional domains in core antigen and e antigen from hepatitis B virus," Journal of Virology, 63(2):798–808 (1989).

Sallberg et al., "Characterization of a linear binding site for a monoclonal antibody to hepatitis B core antigen," J. Med. Virol., 33(4):248–252 (1991).

Sallberg et al., "Immunochemical structure of the carboxy–terminal part of hepatitis B e antigen: identification of internal and surface–exposed sequences," *Journal of General Virology,* 74:1335–1340 (1993).

Sallberg et al., "Human and murine B–cells recognize the HBeAg/beta (or HBe2) epitope as a linear determinant," Mol. Immunol., 28(7):719–726 (1991).

Sallberg et al., "Rapid 'tea–bag' peptide synthesis using 9–fluorenylmethoxycarbonyl (Fmoc) protected amino acids applied for antigenic mapping of viral proteins," *Immunology Letters,* 30:59–68 (1991).

Schodel et al., "Structure of Hepatitis B Virus Core and e–antigen," *The Journal of Biological Chemistry,* 268:1332–1337 (1993).

Sequence alignment of Genseq sequence alignment of instant SEQ. ID No.: 28 with the antihuman parathyroid hormone–related protein of JP04228089–A, Kaneka Corp., (Aug. 18, 1992), ID No.: AR27008.

Sequence alignment of Genseq sequence alignment of instant SEQ. ID No.: 29 with anti–DNA antibody 7b3 heavy chain variable region of WO 96/36361–a1. University of Michigan, (Aug. 12, 1997) ID No.: AAW04593.

Sequence alignment of Genseq sequence alignment of instant SEQ. ID No.: 33 with anti–proenkephalin antibody PE–19 of WO 9606863, University of Dundee (Oct. 9, 1996) ID No.: AAR91370.

Skrivelis et al., Scand. J. Immunol., 37:637–643 (1993).

Steinbergs et al., Proceedings of the Latvian Academy of Sciences, Section B, 50(2):74–77 (1996).

Takahashi et al., "Acute hepatitis in rates expressing human hepatitis B virus transgenes," Proc. Natl. Acad. Sci USA, 92:1470–1474 (1995).

Wood et al., Veterinary Immunobiology and Immunopathology, 54(1–4):33–44 (1994).

Zhang et al., "Characterization of a monoclonal antibody and its single–chain antibody fragment recognizing the nucleotide triphosphatase/helicase domain of the hepatitis C virus nonstructural 3 protein," Clin. Diag. Lab. Immunol., 7(1)::58–63 (2000).

Zhang et al., "Molecular basis for antibody cross–reactivity between the hepatitis C virus core protein and the hos-derived GOR protein," Clin. Exp. Immunol., 6(33):403–409 (1994).

Kreitman et al., "Immunotoxins for targeted cancer therapy," Advanced Drug Delivery Reviews, 31:53–88 (1998).

Lew et al., "Site–directed Immune responses in DNA vaccines encoding ligand–antigen fusions," Vaccine, England, vol. 18, No. 16, pp. 1681–1685 (2000).

Mollick, et al., "Localization of a Site on Bacterial Superantigens that Determines T Cell Receptor 3 Chain Specificity," J. Exp. Med., 177:283–293 (1993).

Ogg, et al., "Sensitization of tumour cells to lysis by virus–specific CTL using antibody–targeted MHC class I/peptide complexes," British Journal of Cancer, 82(5):1058–1062 (2000).

Owens et al., "Mapping the Collagen–Binding Site of Human Fibronectin by Expression in Escherichia Coli," Embo Journal, IRL Press, Eynsham, GB, vol. 5, No. 11, pp. 2825–2830 (1986).

Barbas et al., "Assembly of combinatorial antibody libraries on phage surfaces: The gene III site," Proc Natl Acad Sci USA, 88:7978–7982, (1991).

Bianchi et al., "Chemical Synthesis of a Designed Beta–Protein through the Flow–Polyamide Method," Int J Pept Protein Res, 41(4):385–393 (1993).

Bianchi et al., "Afinity Purification of a Difficult–Sequence Protein: Implications for the Inclusion of Capping in Synthetic Protocols," Int J Pept Protein Res, 42(1):93–96 (1993).

Bichko et al., "Epitopes recognized by antibodies to denatured core protein of hepatitis B virus," Mol. Immunol., 30(3):221–231, (1993).

Brett et al., "The invasin protein of Yersinia spp. Provides co–stimulatory activity to human T cells thorugh interaction with beta 1 integrins," Eur. J. Immunol., 23(7):1608–1614 (1993).

Cello, J, et al., "Identification of group–common linear epitopes in structural and nonstructural proteins of enteroviruses by using synthetic peptides," J. Clin. Microbiol., 31(4):911–916 (1993).

Chien et al., "Identification of group–common linear epitopes in structural and nonstructural proteins of enteroviruses by using synthetic peptides," Proc Natl Acad Sci USA, 88:9578–9582 (1991).

Cohen, J., et al., "Ligand binding to the cell surface receptor for reovirus type 3 stimulates galactocerebroside expression by developing oligodendrocytes," Proc. Natl. Acad. Sci. USA, 87(13):4922–4926 (1990).

Colberre–Garapin et al., "A new dominant hybrid selective marker for higher eukaryotic cells," J. Molecular Biology, 150:1 (1981).

Doolittle et al., "The amino Acid Sequence of the alpha–Chain of Human Fibrinogen." Nature, 280(5722):464–468, (1979).

Felding–Habermann et al., "Role of β3 Integrins in Melanoma cell Adhesion to Activated Platelets under Flow," J. Biol. Chem., 271(10):5892–5900 (1996).

Flock, "Extracellular–Matrix–Binding Proteins as Targets for the Prevention of Staphylococcus aureus Infections," Molecular Medicine Today, 5(12):532–537 (1999).

Haseltine, "Replication and Pathogenesis of the AIDS Virus," Journal of Acquired Immune Deficiency Syndromes, 1(3):217–240 and 231–236, (1988).

Henschen et al., "Amino acid sequence of human fibrin. Preliminary note on the Completion of the β–Chain Sequence," Z. Physiol. Chem., 358(12):1643–1646 (1977).

Holliger et al., "Diabodies': Small Bivalent and Bispecific Antibody Fragments," Proc Natl Acad Sci USA, 90(14):6444–6448, (1993).

Huse et al., "Generation of a large combinatorial library of the immunoglobulin repertoire in Phage Lambda." Science, 256:1275–1281 (1989).

Katada et al., "A Novel Peptide Motif for Platelet Fibrinogen Receptor Recognition," J. Biol. Chem., 272(12):7720–7726 (1997).

Leanna & Hannink, "The reverse two–hybrid system: a genetic scheme for selection against specific protein/protein interactions," Nucl. Acid. Res., 24:3341–3347 (1996).

Levi et al., "A complementarity–determining region synthetic peptide acts as a miniantiody and neutralizes human immunodeficiency virus type 1 in vitro," Proc Natl Acad Sci USA, 90(10):4374–4378, (1993).

Lottspeich et al., "Amino acid sequence of human fibrin. Preliminary note on the Completion of the gamma–Chain Sequence," Z. Physiol. Chem., 358(7):935–938 (1977).

Lowman HB, "Bacteriophage display and discovery of peptide leads for drug development," Annu. Rev. Biophys. Biomol. Struct., 26:401–424 (1997).

McDevvit et al., "Characterization of the interaction between Staphylococcus aureus clumping factor (ClfA) and fibrinogen," Eur. J. Biochem., 247(1):416–424 (1997).

Morrison et al., "Chimeric human antibody molecules: mouse antigen–binding domains with human constant region domains," Proc Natl Acad Sci USA, 81(21):6851–6855 (1984).

Neuberger et al., "Recombinant antibodies possessing novel effector functions," Nature, 312:604–608 (1984).

Pei et al., "Functional Studies of a Fibrinogen Binding Protein from Staphylococcus epidermidis," Infection and Immunity, 67(9):4525–4530 (1999).

Roivanen et al., "Antigenic regions of poliovirus type 3/Sabin capsid proteins recognized by human sera in the peptide scanning technique," *Virology,* 180:99–107 (1991).

Rüther and Müller–Hill, "Easy identification of cDNA clones," *EMBO Journal,* 2(10):1791–1794 (1983).

Sällberg et al., "Synthetic peptides as mini antibodies," Peptides: Chemistry and Biology, eds. Hodges, R. and J. Rivier, ESCOM, Leiden, pp. 715–718 (1993).

Sällberg et al., "The Antigen/Antibody Specificity Exchanger: A New Peptide Based Tool for Re–directing Antibodies of Other Specificities to Recognize the V3 Domain of HIV–1 GP120," *Biochemical and Biophysical Research Communications,* 205:1386–1390 (1994).

Sällberg, M. "Ligand/Receptor Specificity Exchangers that Redirect Antibodies to Receptors on a Pathogen," U.S. Appl. No. 09/664,025, filed Sep. 19, 2000.

Sällberg, M. "Ligand/Receptor Specificity Exchangers that Redirect Antibodies to Receptors on a Pathogen," U.S. Appl. No. 09/664,945, filed Sep. 19, 2000.

Sällberg, M. "Synthetic Peptides That Bind to the Hepatitis B Virus Core and E Antigens," U.S. Appl. No. 10/153,271, filed May 21, 2002.

Saragovi et al., "Design and Synthesis of a Mimetic from an Antibody Complementarity–Determining Region," *Science,* 253(5021):792–795 (1991).

Takeda et al., "Construction of chimaeric processed immunoglobulin genes containing mouse variable and human constant regionsequences," *Nature,* 314:452–454 (1985).

Taub, R., et al., "A monoclonal antibody against the platelet fibrinogen receptor contains a sequence that mimics a receptor recognition domain in fibrinogen," *J. Biol. Chem.,* 264(1):259–265 (1989).

Tramontano et al., "The making of the minibody: an engineered β–protein for the display of conformationally constrained peptides," *J. of Molecular Recognition,* 7(1):9–24 (1994).

Watt et al., "Amino Acid Sequence of the β–Chain of Human Fibrinogen," *Biochemistry,* 18(1):68–76 (1979).

Watt et al., "Amino acid sequence studies on the alpha chain of human fibrinogen overlapping sequences providing the complete sequence," *Biochemistry,* 18(24):5410–5416 (1979).

Williams et al., "Design of bioactive peptides based on antibody hypervariable region structures. Development of conformationally constrained and dimeric peptides with enhanced affinity," *J. Biol. Chem.,* 266(8):5182–5190 (1991).

Williams et al., "Development of biologically active peptides based on antibody structure," *Proc Natl Acad Sci USA,* 86(14):5537–5541 (1989).

Winter and Milstein, "Man–made antibodies," *Nature,* 349(6307):293–299 (1991).

Zanetti, "Antigenized Antibodies," *Nature,* 355:476–477 (1992).

* cited by examiner

SEQUENCE LISTING

```
<160> NUMBER OF SEQ ID NOS: 199

<210> SEQ ID NO 1
<211> LENGTH: 18
<212> TYPE: PRT
<213> ORGANISM: Artificial Sequence
```

```
<220> FEATURE:
<223> OTHER INFORMATION: Artificially Synthesized Peptides

<400> SEQUENCE: 1

Tyr Gly Glu Gly Gln Gln His His Leu Gly Gly Ala Lys Gln Ala Gly
 1               5                  10                  15

Asp Val

<210> SEQ ID NO 2
<211> LENGTH: 20
<212> TYPE: PRT
<213> ORGANISM: Artificial Sequence
<220> FEATURE:
<223> OTHER INFORMATION: Artificially Synthesized Peptides

<400> SEQUENCE: 2

Met Ser Trp Ser Leu His Pro Arg Asn Leu Ile Leu Tyr Phe Tyr Ala
 1               5                  10                  15

Leu Leu Phe Leu
            20

<210> SEQ ID NO 3
<211> LENGTH: 19
<212> TYPE: PRT
<213> ORGANISM: Artificial Sequence
<220> FEATURE:
<223> OTHER INFORMATION: Artificially Synthesized Peptides

<400> SEQUENCE: 3

Ile Leu Tyr Phe Tyr Ala Leu Leu Phe Leu Ser Thr Cys Val Ala Tyr
 1               5                  10                  15

Val Ala Thr

<210> SEQ ID NO 4
<211> LENGTH: 20
<212> TYPE: PRT
<213> ORGANISM: Artificial Sequence
<220> FEATURE:
<223> OTHER INFORMATION: Artificially Synthesized Peptides

<400> SEQUENCE: 4

Ser Ser Thr Cys Val Ala Tyr Val Ala Thr Arg Asp Asn Cys Cys Ile
 1               5                  10                  15

Leu Asp Glu Arg
            20

<210> SEQ ID NO 5
<211> LENGTH: 20
<212> TYPE: PRT
<213> ORGANISM: Artificial Sequence
<220> FEATURE:
<223> OTHER INFORMATION: Artificially Synthesized Peptides

<400> SEQUENCE: 5

Arg Asp Asn Cys Cys Ile Leu Asp Glu Arg Phe Gly Ser Tyr Cys Pro
 1               5                  10                  15

Thr Thr Cys Gly
            20

<210> SEQ ID NO 6
<211> LENGTH: 20
<212> TYPE: PRT
<213> ORGANISM: Artificial Sequence
<220> FEATURE:
```

```
<223> OTHER INFORMATION: Artificially Synthesized Peptides

<400> SEQUENCE: 6

Phe Gly Ser Tyr Cys Pro Thr Thr Cys Gly Ile Ala Asp Phe Leu Ser
1               5                   10                  15

Thr Tyr Gln Thr
            20

<210> SEQ ID NO 7
<211> LENGTH: 20
<212> TYPE: PRT
<213> ORGANISM: Artificial Sequence
<220> FEATURE:
<223> OTHER INFORMATION: Artificially Synthesized Peptides

<400> SEQUENCE: 7

Ile Ala Asp Phe Leu Ser Thr Tyr Gln Thr Lys Val Asp Lys Asp Leu
1               5                   10                  15

Gln Ser Leu Glu
            20

<210> SEQ ID NO 8
<211> LENGTH: 20
<212> TYPE: PRT
<213> ORGANISM: Artificial Sequence
<220> FEATURE:
<223> OTHER INFORMATION: Artificially Synthesized Peptides

<400> SEQUENCE: 8

Lys Val Asp Lys Asp Leu Gln Ser Leu Glu Asp Ile Leu His Gln Val
1               5                   10                  15

Glu Asn Lys Thr
            20

<210> SEQ ID NO 9
<211> LENGTH: 20
<212> TYPE: PRT
<213> ORGANISM: Artificial Sequence
<220> FEATURE:
<223> OTHER INFORMATION: Artificially Synthesized Peptides

<400> SEQUENCE: 9

Asp Ile Leu His Gln Val Glu Asn Lys Thr Ser Glu Val Lys Gln Leu
1               5                   10                  15

Ile Lys Ala Ile
            20

<210> SEQ ID NO 10
<211> LENGTH: 20
<212> TYPE: PRT
<213> ORGANISM: Artificial Sequence
<220> FEATURE:
<223> OTHER INFORMATION: Artificially Synthesized Peptides

<400> SEQUENCE: 10

Ser Glu Val Lys Gln Leu Ile Lys Ala Ile Gln Leu Thr Tyr Asn Pro
1               5                   10                  15

Asp Glu Ser Ser
            20

<210> SEQ ID NO 11
<211> LENGTH: 20
<212> TYPE: PRT
<213> ORGANISM: Artificial Sequence
```

```
<220> FEATURE:
<223> OTHER INFORMATION: Artificially Synthesized Peptides

<400> SEQUENCE: 11

Gln Leu Thr Tyr Asn Pro Asp Glu Ser Ser Lys Pro Asn Met Ile Asp
 1               5                  10                  15

Ala Ala Thr Leu
            20

<210> SEQ ID NO 12
<211> LENGTH: 20
<212> TYPE: PRT
<213> ORGANISM: Artificial Sequence
<220> FEATURE:
<223> OTHER INFORMATION: Artificially Synthesized Peptides

<400> SEQUENCE: 12

Lys Pro Asn Met Ile Asp Ala Ala Thr Leu Lys Ser Arg Ile Met Leu
 1               5                  10                  15

Glu Glu Ile Met
            20

<210> SEQ ID NO 13
<211> LENGTH: 20
<212> TYPE: PRT
<213> ORGANISM: Artificial Sequence
<220> FEATURE:
<223> OTHER INFORMATION: Artificially Synthesized Peptides

<400> SEQUENCE: 13

Lys Ser Arg Ile Met Leu Glu Glu Ile Met Lys Tyr Glu Ala Ser Ile
 1               5                  10                  15

Leu Thr His Asp
            20

<210> SEQ ID NO 14
<211> LENGTH: 20
<212> TYPE: PRT
<213> ORGANISM: Artificial Sequence
<220> FEATURE:
<223> OTHER INFORMATION: Artificially Synthesized Peptides

<400> SEQUENCE: 14

Lys Tyr Glu Ala Ser Ile Leu Thr His Asp Ser Ser Ile Arg Tyr Leu
 1               5                  10                  15

Gln Glu Ile Tyr
            20

<210> SEQ ID NO 15
<211> LENGTH: 20
<212> TYPE: PRT
<213> ORGANISM: Artificial Sequence
<220> FEATURE:
<223> OTHER INFORMATION: Artificially Synthesized Peptides

<400> SEQUENCE: 15

Ser Ser Ile Arg Tyr Leu Gln Glu Ile Tyr Asn Ser Asn Asn Gln Lys
 1               5                  10                  15

Ile Val Asn Leu
            20

<210> SEQ ID NO 16
<211> LENGTH: 20
<212> TYPE: PRT
```

<213> ORGANISM: Artificial Sequence
<220> FEATURE:
<223> OTHER INFORMATION: Artificially Synthesized Peptides

<400> SEQUENCE: 16

Asn Ser Asn Asn Gln Lys Ile Val Asn Leu Lys Glu Lys Val Ala Gln
 1               5                   10                  15
Leu Glu Ala Gln
            20

<210> SEQ ID NO 17
<211> LENGTH: 20
<212> TYPE: PRT
<213> ORGANISM: Artificial Sequence
<220> FEATURE:
<223> OTHER INFORMATION: Artificially Synthesized Peptides

<400> SEQUENCE: 17

Cys Gln Glu Pro Cys Lys Asp Thr Val Gln Ile His Asp Ile Thr Gly
 1               5                   10                  15
Lys Asp Cys Gln
            20

<210> SEQ ID NO 18
<211> LENGTH: 20
<212> TYPE: PRT
<213> ORGANISM: Artificial Sequence
<220> FEATURE:
<223> OTHER INFORMATION: Artificially Synthesized Peptides

<400> SEQUENCE: 18

Ile His Asp Ile Thr Gly Lys Asp Cys Gln Asp Ile Ala Asn Lys Gly
 1               5                   10                  15
Ala Lys Gln Ser
            20

<210> SEQ ID NO 19
<211> LENGTH: 20
<212> TYPE: PRT
<213> ORGANISM: Artificial Sequence
<220> FEATURE:
<223> OTHER INFORMATION: Artificially Synthesized Peptides

<400> SEQUENCE: 19

Asp Ile Ala Asn Lys Gly Ala Lys Gln Ser Gly Leu Tyr Phe Ile Lys
 1               5                   10                  15
Pro Leu Lys Ala
            20

<210> SEQ ID NO 20
<211> LENGTH: 20
<212> TYPE: PRT
<213> ORGANISM: Artificial Sequence
<220> FEATURE:
<223> OTHER INFORMATION: Artificially Synthesized Peptides

<400> SEQUENCE: 20

Gly Leu Tyr Phe Ile Lys Pro Leu Lys Ala Asn Gln Gln Phe Leu Val
 1               5                   10                  15
Tyr Cys Glu Ile
            20

<210> SEQ ID NO 21
<211> LENGTH: 20

```
<212> TYPE: PRT
<213> ORGANISM: Artificial Sequence
<220> FEATURE:
<223> OTHER INFORMATION: Artificially Synthesized Peptides

<400> SEQUENCE: 21

Asn Gln Gln Phe Leu Val Tyr Cys Glu Ile Asp Gly Ser Gly Asn Gly
 1               5                  10                  15

Trp Thr Val Phe
            20

<210> SEQ ID NO 22
<211> LENGTH: 20
<212> TYPE: PRT
<213> ORGANISM: Artificial Sequence
<220> FEATURE:
<223> OTHER INFORMATION: Artificially Synthesized Peptides

<400> SEQUENCE: 22

Asp Gly Ser Gly Asn Gly Trp Thr Val Phe Gln Lys Arg Leu Asp Gly
 1               5                  10                  15

Ser Val Asp Phe
            20

<210> SEQ ID NO 23
<211> LENGTH: 20
<212> TYPE: PRT
<213> ORGANISM: Artificial Sequence
<220> FEATURE:
<223> OTHER INFORMATION: Artificially Synthesized Peptides

<400> SEQUENCE: 23

Gln Lys Arg Leu Asp Gly Ser Val Asp Phe Lys Lys Asn Trp Ile Gln
 1               5                  10                  15

Tyr Lys Glu Gly
            20

<210> SEQ ID NO 24
<211> LENGTH: 20
<212> TYPE: PRT
<213> ORGANISM: Artificial Sequence
<220> FEATURE:
<223> OTHER INFORMATION: Artificially Synthesized Peptides

<400> SEQUENCE: 24

Lys Lys Asn Trp Ile Gln Tyr Lys Glu Gly Phe Gly His Leu Ser Pro
 1               5                  10                  15

Thr Gly Thr Thr
            20

<210> SEQ ID NO 25
<211> LENGTH: 20
<212> TYPE: PRT
<213> ORGANISM: Artificial Sequence
<220> FEATURE:
<223> OTHER INFORMATION: Artificially Synthesized Peptides

<400> SEQUENCE: 25

Phe Gly His Leu Ser Pro Thr Gly Thr Thr Glu Phe Trp Leu Gly Asn
 1               5                  10                  15

Glu Lys Ile His
            20

<210> SEQ ID NO 26
```

```
<211> LENGTH: 20
<212> TYPE: PRT
<213> ORGANISM: Artificial Sequence
<220> FEATURE:
<223> OTHER INFORMATION: Artificially Synthesized Peptides

<400> SEQUENCE: 26

Glu Phe Trp Leu Gly Asn Glu Lys Ile His Leu Ile Ser Thr Gln Ser
 1               5                  10                  15

Ala Ile Pro Tyr
            20

<210> SEQ ID NO 27
<211> LENGTH: 20
<212> TYPE: PRT
<213> ORGANISM: Artificial Sequence
<220> FEATURE:
<223> OTHER INFORMATION: Artificially Synthesized Peptides

<400> SEQUENCE: 27

Leu Ile Ser Thr Gln Ser Ala Ile Pro Tyr Ala Leu Arg Val Glu Leu
 1               5                  10                  15

Glu Asp Trp Asn
            20

<210> SEQ ID NO 28
<211> LENGTH: 20
<212> TYPE: PRT
<213> ORGANISM: Artificial Sequence
<220> FEATURE:
<223> OTHER INFORMATION: Artificially Synthesized Peptides

<400> SEQUENCE: 28

Ala Leu Arg Val Glu Leu Glu Asp Trp Asn Gly Arg Thr Ser Thr Ala
 1               5                  10                  15

Asp Tyr Ala Met
            20

<210> SEQ ID NO 29
<211> LENGTH: 20
<212> TYPE: PRT
<213> ORGANISM: Artificial Sequence
<220> FEATURE:
<223> OTHER INFORMATION: Artificially Synthesized Peptides

<400> SEQUENCE: 29

Gly Arg Thr Ser Thr Ala Asp Tyr Ala Met Phe Lys Val Gly Pro Glu
 1               5                  10                  15

Ala Asp Lys Tyr
            20

<210> SEQ ID NO 30
<211> LENGTH: 20
<212> TYPE: PRT
<213> ORGANISM: Artificial Sequence
<220> FEATURE:
<223> OTHER INFORMATION: Artificially Synthesized Peptides

<400> SEQUENCE: 30

Phe Lys Val Gly Pro Glu Ala Asp Lys Tyr Arg Leu Thr Tyr Ala Tyr
 1               5                  10                  15

Phe Ala Gly Gly
            20
```

```
<210> SEQ ID NO 31
<211> LENGTH: 20
<212> TYPE: PRT
<213> ORGANISM: Artificial Sequence
<220> FEATURE:
<223> OTHER INFORMATION: Artificially Synthesized Peptides

<400> SEQUENCE: 31

Arg Leu Thr Tyr Ala Tyr Phe Ala Gly Gly Asp Ala Gly Asp Ala Phe
 1               5                  10                  15

Asp Gly Phe Asp
            20

<210> SEQ ID NO 32
<211> LENGTH: 20
<212> TYPE: PRT
<213> ORGANISM: Artificial Sequence
<220> FEATURE:
<223> OTHER INFORMATION: Artificially Synthesized Peptides

<400> SEQUENCE: 32

Asp Ala Gly Asp Ala Phe Asp Gly Phe Asp Phe Gly Asp Asp Pro Ser
 1               5                  10                  15

Asp Lys Phe Phe
            20

<210> SEQ ID NO 33
<211> LENGTH: 20
<212> TYPE: PRT
<213> ORGANISM: Artificial Sequence
<220> FEATURE:
<223> OTHER INFORMATION: Artificially Synthesized Peptides

<400> SEQUENCE: 33

Phe Gly Asp Asp Pro Ser Asp Lys Phe Phe Thr Ser His Asn Gly Met
 1               5                  10                  15

Gln Phe Ser Thr
            20

<210> SEQ ID NO 34
<211> LENGTH: 20
<212> TYPE: PRT
<213> ORGANISM: Artificial Sequence
<220> FEATURE:
<223> OTHER INFORMATION: Artificially Synthesized Peptides

<400> SEQUENCE: 34

Thr Ser His Asn Gly Met Gln Phe Ser Thr Trp Asp Asn Asp Asn Asp
 1               5                  10                  15

Lys Phe Glu Gly
            20

<210> SEQ ID NO 35
<211> LENGTH: 20
<212> TYPE: PRT
<213> ORGANISM: Artificial Sequence
<220> FEATURE:
<223> OTHER INFORMATION: Artificially Synthesized Peptides

<400> SEQUENCE: 35

Trp Asp Asn Asp Asn Asp Lys Phe Glu Gly Asn Cys Ala Glu Gln Asp
 1               5                  10                  15

Gly Ser Gly Trp
            20
```

<210> SEQ ID NO 36
<211> LENGTH: 20
<212> TYPE: PRT
<213> ORGANISM: Artificial Sequence
<220> FEATURE:
<223> OTHER INFORMATION: Artificially Synthesized Peptides

<400> SEQUENCE: 36

Asn Cys Ala Glu Gln Asp Gly Ser Gly Trp Trp Met Asn Lys Cys His
 1               5                  10                  15

Ala Gly His Leu
            20

<210> SEQ ID NO 37
<211> LENGTH: 20
<212> TYPE: PRT
<213> ORGANISM: Artificial Sequence
<220> FEATURE:
<223> OTHER INFORMATION: Artificially Synthesized Peptides

<400> SEQUENCE: 37

Trp Met Asn Lys Cys His Ala Gly His Leu Asn Gly Val Tyr Tyr Gln
 1               5                  10                  15

Gly Gly Thr Tyr
            20

<210> SEQ ID NO 38
<211> LENGTH: 20
<212> TYPE: PRT
<213> ORGANISM: Artificial Sequence
<220> FEATURE:
<223> OTHER INFORMATION: Artificially Synthesized Peptides

<400> SEQUENCE: 38

Asn Gly Val Tyr Tyr Gln Gly Gly Thr Tyr Ser Lys Ala Ser Thr Pro
 1               5                  10                  15

Asn Gly Tyr Asp
            20

<210> SEQ ID NO 39
<211> LENGTH: 20
<212> TYPE: PRT
<213> ORGANISM: Artificial Sequence
<220> FEATURE:
<223> OTHER INFORMATION: Artificially Synthesized Peptides

<400> SEQUENCE: 39

Ser Lys Ala Ser Thr Pro Asn Gly Tyr Asp Asn Gly Ile Ile Trp Ala
 1               5                  10                  15

Thr Trp Lys Thr
            20

<210> SEQ ID NO 40
<211> LENGTH: 20
<212> TYPE: PRT
<213> ORGANISM: Artificial Sequence
<220> FEATURE:
<223> OTHER INFORMATION: Artificially Synthesized Peptides

<400> SEQUENCE: 40

Asn Gly Ile Ile Trp Ala Thr Trp Lys Thr Arg Trp Tyr Ser Met Lys
 1               5                  10                  15

Lys Thr Thr Met
            20

```
<210> SEQ ID NO 41
<211> LENGTH: 20
<212> TYPE: PRT
<213> ORGANISM: Artificial Sequence
<220> FEATURE:
<223> OTHER INFORMATION: Artificially Synthesized Peptides

<400> SEQUENCE: 41

Arg Trp Tyr Ser Met Lys Lys Thr Thr Met Lys Ile Ile Pro Phe Asn
 1               5                  10                  15

Arg Leu Thr Ile
            20

<210> SEQ ID NO 42
<211> LENGTH: 27
<212> TYPE: PRT
<213> ORGANISM: Artificial Sequence
<220> FEATURE:
<223> OTHER INFORMATION: Artificially Synthesized Peptides

<400> SEQUENCE: 42

Lys Ile Ile Pro Phe Asn Arg Leu Thr Ile Gly Glu Gly Gln Gln His
 1               5                  10                  15

His Leu Gly Gly Ala Lys Gln Ala Gly Asp Val
            20                  25

<210> SEQ ID NO 43
<211> LENGTH: 14
<212> TYPE: PRT
<213> ORGANISM: Artificial Sequence
<220> FEATURE:
<223> OTHER INFORMATION: Artificially Synthesized Peptides

<400> SEQUENCE: 43

Cys Asp Leu Ile Tyr Tyr Asp Tyr Glu Glu Asp Tyr Tyr Phe
 1               5                  10

<210> SEQ ID NO 44
<211> LENGTH: 13
<212> TYPE: PRT
<213> ORGANISM: Artificial Sequence
<220> FEATURE:
<223> OTHER INFORMATION: Artificially Synthesized Peptides

<400> SEQUENCE: 44

Cys Asp Leu Ile Tyr Tyr Asp Tyr Glu Glu Asp Tyr Tyr
 1               5                  10

SEQ ID NO 45

LENGTH: 5
TYPE: PRT
<213> ORGANISM: Artificial Sequence
<220> FEATURE:
<223> OTHER INFORMATION: Artificially Synthesized Peptides

<400> SEQUENCE: 45

Thr Tyr Ala Met Asn
 1               5

<210> SEQ ID NO 46
<211> LENGTH: 19
<212> TYPE: PRT
<213> ORGANISM: Artificial Sequence
<220> FEATURE:
```

<223> OTHER INFORMATION: Artificially Synthesized Peptides

<400> SEQUENCE: 46

Arg Val Arg Ser Lys Ser Phe Asn Tyr Ala Thr Tyr Tyr Ala Asp Ser
1               5                   10                  15
Val Lys Gly

<210> SEQ ID NO 47
<211> LENGTH: 14
<212> TYPE: PRT
<213> ORGANISM: Artificial Sequence
<220> FEATURE:
<223> OTHER INFORMATION: Artificially Synthesized Peptides

<400> SEQUENCE: 47

Pro Ala Gln Gly Ile Tyr Phe Asp Tyr Gly Gly Phe Ala Tyr
1               5                   10

<210> SEQ ID NO 48
<211> LENGTH: 17
<212> TYPE: PRT
<213> ORGANISM: Artificial Sequence
<220> FEATURE:
<223> OTHER INFORMATION: Artificially Synthesized Peptides

<400> SEQUENCE: 48

Gly Leu Tyr Ser Ser Ile Trp Leu Ser Pro Gly Arg Ser Tyr Phe Glu
1               5                   10                  15
Thr

<210> SEQ ID NO 49
<211> LENGTH: 17
<212> TYPE: PRT
<213> ORGANISM: Artificial Sequence
<220> FEATURE:
<223> OTHER INFORMATION: Artificially Synthesized Peptides

<400> SEQUENCE: 49

Tyr Thr Asp Ile Lys Tyr Asn Pro Phe Thr Asp Arg Gly Glu Gly Asn
1               5                   10                  15
Met

<210> SEQ ID NO 50
<211> LENGTH: 17
<212> TYPE: PRT
<213> ORGANISM: Artificial Sequence
<220> FEATURE:
<223> OTHER INFORMATION: Artificially Synthesized Peptides

<400> SEQUENCE: 50

Asp Gln Asn Ile His Met Asn Ala Arg Leu Leu Ile Arg Ser Pro Phe
1               5                   10                  15
Thr

<210> SEQ ID NO 51
<211> LENGTH: 17
<212> TYPE: PRT
<213> ORGANISM: Artificial Sequence
<220> FEATURE:
<223> OTHER INFORMATION: Artificially Synthesized Peptides

<400> SEQUENCE: 51

Leu Ile Arg Ser Pro Phe Thr Asp Pro Gln Leu Leu Val His Thr Asp
1               5                   10                  15

Pro

<210> SEQ ID NO 52
<211> LENGTH: 17
<212> TYPE: PRT
<213> ORGANISM: Artificial Sequence
<220> FEATURE:
<223> OTHER INFORMATION: Artificially Synthesized Peptides

<400> SEQUENCE: 52

Gln Lys Glu Ser Leu Leu Phe Pro Pro Val Lys Leu Leu Arg Arg Val
 1               5                  10                  15
Pro

<210> SEQ ID NO 53
<211> LENGTH: 11
<212> TYPE: PRT
<213> ORGANISM: Artificial Sequence
<220> FEATURE:
<223> OTHER INFORMATION: Artificially Synthesized Peptides

<400> SEQUENCE: 53

Pro Ala Leu Thr Ala Val Glu Thr Gly Ala Thr
 1               5                  10

<210> SEQ ID NO 54
<211> LENGTH: 8
<212> TYPE: PRT
<213> ORGANISM: Artificial Sequence
<220> FEATURE:
<223> OTHER INFORMATION: Artificially Synthesized Peptides

<400> SEQUENCE: 54

Ser Thr Leu Val Pro Glu Thr Thr
 1               5

<210> SEQ ID NO 55
<211> LENGTH: 13
<212> TYPE: PRT
<213> ORGANISM: Artificial Sequence
<220> FEATURE:
<223> OTHER INFORMATION: Artificially Synthesized Peptides

<400> SEQUENCE: 55

Thr Pro Pro Ala Tyr Arg Pro Pro Asn Ala Pro Ile Leu
 1               5                  10

<210> SEQ ID NO 56
<211> LENGTH: 9
<212> TYPE: PRT
<213> ORGANISM: Artificial Sequence
<220> FEATURE:
<223> OTHER INFORMATION: Artificially Synthesized Peptides

<400> SEQUENCE: 56

Glu Ile Pro Ala Leu Thr Ala Val Glu
 1               5

<210> SEQ ID NO 57
<211> LENGTH: 10
<212> TYPE: PRT
<213> ORGANISM: Artificial Sequence
<220> FEATURE:
<223> OTHER INFORMATION: Artificially Synthesized Peptides

<400> SEQUENCE: 57

```
Leu Glu Asp Pro Ala Ser Arg Asp Leu Val
  1               5                  10
```

```
<210> SEQ ID NO 58
<211> LENGTH: 8
<212> TYPE: PRT
<213> ORGANISM: Artificial Sequence
<220> FEATURE:
<223> OTHER INFORMATION: Artificially Synthesized Peptides

<400> SEQUENCE: 58
```

```
His Arg Gly Gly Pro Glu Glu Phe
  1               5
```

```
<210> SEQ ID NO 59
<211> LENGTH: 7
<212> TYPE: PRT
<213> ORGANISM: Artificial Sequence
<220> FEATURE:
<223> OTHER INFORMATION: Artificially Synthesized Peptides

<400> SEQUENCE: 59
```

```
His Arg Gly Gly Pro Glu Glu
  1               5
```

```
<210> SEQ ID NO 60
<211> LENGTH: 17
<212> TYPE: PRT
<213> ORGANISM: Artificial Sequence
<220> FEATURE:
<223> OTHER INFORMATION: Artificially Synthesized Peptides

<400> SEQUENCE: 60
```

```
Val Leu Ile Cys Gly Glu Asn Thr Val Ser Arg Asn Tyr Ala Thr His
  1               5                  10                  15
Ser
```

```
<210> SEQ ID NO 61
<211> LENGTH: 17
<212> TYPE: PRT
<213> ORGANISM: Artificial Sequence
<220> FEATURE:
<223> OTHER INFORMATION: Artificially Synthesized Peptides

<400> SEQUENCE: 61
```

```
Lys Ile Asn Thr Met Pro Pro Phe Leu Asp Thr Glu Leu Thr Ala Pro
  1               5                  10                  15
Ser
```

```
<210> SEQ ID NO 62
<211> LENGTH: 17
<212> TYPE: PRT
<213> ORGANISM: Artificial Sequence
<220> FEATURE:
<223> OTHER INFORMATION: Artificially Synthesized Peptides

<400> SEQUENCE: 62
```

```
Pro Asp Glu Lys Ser Gln Arg Glu Ile Leu Leu Asn Lys Ile Ala Ser
  1               5                  10                  15
Tyr
```

```
<210> SEQ ID NO 63
<211> LENGTH: 17
<212> TYPE: PRT
```

-continued

```
<213> ORGANISM: Artificial Sequence
<220> FEATURE:
<223> OTHER INFORMATION: Artificially Synthesized Peptides

<400> SEQUENCE: 63

Thr Ala Thr Thr Thr Thr Tyr Ala Tyr Pro Gly Thr Asn Arg Pro Pro
 1               5                  10                  15

Val

<210> SEQ ID NO 64
<211> LENGTH: 8
<212> TYPE: PRT
<213> ORGANISM: Artificial Sequence
<220> FEATURE:
<223> OTHER INFORMATION: Artificially Synthesized Peptides

<400> SEQUENCE: 64

Ser Thr Pro Leu Pro Glu Thr Thr
 1               5

<210> SEQ ID NO 65
<211> LENGTH: 8
<212> TYPE: PRT
<213> ORGANISM: Artificial Sequence
<220> FEATURE:
<223> OTHER INFORMATION: Artificially Synthesized Peptides

<400> SEQUENCE: 65

Pro Pro Asn Ala Pro Ile Leu Ser
 1               5

<210> SEQ ID NO 66
<211> LENGTH: 10
<212> TYPE: PRT
<213> ORGANISM: Artificial Sequence
<220> FEATURE:
<223> OTHER INFORMATION: Artificially Synthesized Peptides

<400> SEQUENCE: 66

Arg Pro Pro Asn Ala Pro Ile Leu Ser Thr
 1               5                  10

<210> SEQ ID NO 67
<211> LENGTH: 12
<212> TYPE: PRT
<213> ORGANISM: Artificial Sequence
<220> FEATURE:
<223> OTHER INFORMATION: Artificially Synthesized Peptides

<400> SEQUENCE: 67

Lys Glu Ile Pro Ala Leu Thr Ala Val Glu Thr Gly
 1               5                  10

<210> SEQ ID NO 68
<211> LENGTH: 12
<212> TYPE: PRT
<213> ORGANISM: Artificial Sequence
<220> FEATURE:
<223> OTHER INFORMATION: Artificially Synthesized Peptides

<400> SEQUENCE: 68

Pro Ala His Ser Lys Glu Ile Pro Ala Leu Thr Ala
 1               5                  10

<210> SEQ ID NO 69
<211> LENGTH: 10
```

```
<212> TYPE: PRT
<213> ORGANISM: Artificial Sequence
<220> FEATURE:
<223> OTHER INFORMATION: Artificially Synthesized Peptides

<400> SEQUENCE: 69

Trp Gly Cys Ser Gly Lys Leu Ile Cys Thr
 1               5                  10

<210> SEQ ID NO 70
<211> LENGTH: 10
<212> TYPE: PRT
<213> ORGANISM: Artificial Sequence
<220> FEATURE:
<223> OTHER INFORMATION: Artificially Synthesized Peptides

<400> SEQUENCE: 70

Cys Thr Thr Ala Val Pro Trp Asn Ala Ser
 1               5                  10

<210> SEQ ID NO 71
<211> LENGTH: 11
<212> TYPE: PRT
<213> ORGANISM: Artificial Sequence
<220> FEATURE:
<223> OTHER INFORMATION: Artificially Synthesized Peptides

<400> SEQUENCE: 71

Gln Arg Lys Thr Lys Arg Asn Thr Asn Arg Arg
 1               5                  10

<210> SEQ ID NO 72
<211> LENGTH: 26
<212> TYPE: PRT
<213> ORGANISM: Artificial Sequence
<220> FEATURE:
<223> OTHER INFORMATION: Artificially Synthesized Peptides

<400> SEQUENCE: 72

Tyr Gly Glu Gly Gln Gln His His Leu Gly Gly Ala Lys Gln Ala Gly
 1               5                  10                  15

Asp Val His Arg Gly Gly Pro Glu Glu Phe
            20                  25

<210> SEQ ID NO 73
<211> LENGTH: 25
<212> TYPE: PRT
<213> ORGANISM: Artificial Sequence
<220> FEATURE:
<223> OTHER INFORMATION: Artificially Synthesized Peptides

<400> SEQUENCE: 73

Tyr Gly Glu Gly Gln Gln His His Leu Gly Gly Ala Lys Gln Ala Gly
 1               5                  10                  15

Asp Val His Arg Gly Gly Pro Glu Glu
            20                  25

<210> SEQ ID NO 74
<211> LENGTH: 26
<212> TYPE: PRT
<213> ORGANISM: Artificial Sequence
<220> FEATURE:
<223> OTHER INFORMATION: Artificially Synthesized Peptides

<400> SEQUENCE: 74

Tyr Gly Glu Gly Gln Gln His His Leu Gly Gly Ala Lys Gln Ala Gly
```

```
                1               5              10              15

Asp Val Ser Thr Pro Leu Pro Glu Thr Thr
                20              25

<210> SEQ ID NO 75
<211> LENGTH: 27
<212> TYPE: PRT
<213> ORGANISM: Artificial Sequence
<220> FEATURE:
<223> OTHER INFORMATION: Artificially Synthesized Peptides

<400> SEQUENCE: 75

Met Ser Trp Ser Leu His Pro Arg Asn Leu Ile Leu Tyr Phe Tyr Ala
 1               5              10              15

Leu Leu Phe Leu His Arg Gly Gly Pro Glu Glu
                20              25

<210> SEQ ID NO 76
<211> LENGTH: 26
<212> TYPE: PRT
<213> ORGANISM: Artificial Sequence
<220> FEATURE:
<223> OTHER INFORMATION: Artificially Synthesized Peptides

<400> SEQUENCE: 76

Ile Leu Tyr Phe Tyr Ala Leu Leu Phe Leu Ser Thr Cys Val Ala Tyr
 1               5              10              15

Val Ala Thr His Arg Gly Gly Pro Glu Glu
                20              25

<210> SEQ ID NO 77
<211> LENGTH: 27
<212> TYPE: PRT
<213> ORGANISM: Artificial Sequence
<220> FEATURE:
<223> OTHER INFORMATION: Artificially Synthesized Peptides

<400> SEQUENCE: 77

Ser Ser Thr Cys Val Ala Tyr Val Ala Thr Arg Asp Asn Cys Cys Ile
 1               5              10              15

Leu Asp Glu Arg His Arg Gly Gly Pro Glu Glu
                20              25

<210> SEQ ID NO 78
<211> LENGTH: 27
<212> TYPE: PRT
<213> ORGANISM: Artificial Sequence
<220> FEATURE:
<223> OTHER INFORMATION: Artificially Synthesized Peptides

<400> SEQUENCE: 78

Arg Asp Asn Cys Cys Ile Leu Asp Glu Arg Phe Gly Ser Tyr Cys Pro
 1               5              10              15

Thr Thr Cys Gly His Arg Gly Gly Pro Glu Glu
                20              25

<210> SEQ ID NO 79
<211> LENGTH: 27
<212> TYPE: PRT
<213> ORGANISM: Artificial Sequence
<220> FEATURE:
<223> OTHER INFORMATION: Artificially Synthesized Peptides

<400> SEQUENCE: 79
```

-continued

Phe Gly Ser Tyr Cys Pro Thr Thr Cys Gly Ile Ala Asp Phe Leu Ser
1               5                   10                  15

Thr Tyr Gln Thr His Arg Gly Gly Pro Glu Glu
            20                  25

<210> SEQ ID NO 80
<211> LENGTH: 27
<212> TYPE: PRT
<213> ORGANISM: Artificial Sequence
<220> FEATURE:
<223> OTHER INFORMATION: Artificially Synthesized Peptides

<400> SEQUENCE: 80

Ile Ala Asp Phe Leu Ser Thr Tyr Gln Thr Lys Val Asp Lys Asp Leu
1               5                   10                  15

Gln Ser Leu Glu His Arg Gly Gly Pro Glu Glu
            20                  25

<210> SEQ ID NO 81
<211> LENGTH: 27
<212> TYPE: PRT
<213> ORGANISM: Artificial Sequence
<220> FEATURE:
<223> OTHER INFORMATION: Artificially Synthesized Peptides

<400> SEQUENCE: 81

Lys Val Asp Lys Asp Leu Gln Ser Leu Glu Asp Ile Leu His Gln Val
1               5                   10                  15

Glu Asn Lys Thr His Arg Gly Gly Pro Glu Glu
            20                  25

<210> SEQ ID NO 82
<211> LENGTH: 27
<212> TYPE: PRT
<213> ORGANISM: Artificial Sequence
<220> FEATURE:
<223> OTHER INFORMATION: Artificially Synthesized Peptides

<400> SEQUENCE: 82

Asp Ile Leu His Gln Val Glu Asn Lys Thr Ser Glu Val Lys Gln Leu
1               5                   10                  15

Ile Lys Ala Ile His Arg Gly Gly Pro Glu Glu
            20                  25

<210> SEQ ID NO 83
<211> LENGTH: 27
<212> TYPE: PRT
<213> ORGANISM: Artificial Sequence
<220> FEATURE:
<223> OTHER INFORMATION: Artificially Synthesized Peptides

<400> SEQUENCE: 83

Ser Glu Val Lys Gln Leu Ile Lys Ala Ile Gln Leu Thr Tyr Asn Pro
1               5                   10                  15

Asp Glu Ser Ser His Arg Gly Gly Pro Glu Glu
            20                  25

<210> SEQ ID NO 84
<211> LENGTH: 27
<212> TYPE: PRT
<213> ORGANISM: Artificial Sequence
<220> FEATURE:
<223> OTHER INFORMATION: Artificially Synthesized Peptides

<400> SEQUENCE: 84

Gln Leu Thr Tyr Asn Pro Asp Glu Ser Ser Lys Pro Asn Met Ile Asp
1               5                   10                  15

Ala Ala Thr Leu His Arg Gly Gly Pro Glu Glu
            20                  25

<210> SEQ ID NO 85
<211> LENGTH: 27
<212> TYPE: PRT
<213> ORGANISM: Artificial Sequence
<220> FEATURE:
<223> OTHER INFORMATION: Artificially Synthesized Peptides

<400> SEQUENCE: 85

Lys Pro Asn Met Ile Asp Ala Ala Thr Leu Lys Ser Arg Ile Met Leu
1               5                   10                  15

Glu Glu Ile Met His Arg Gly Gly Pro Glu Glu
            20                  25

<210> SEQ ID NO 86
<211> LENGTH: 27
<212> TYPE: PRT
<213> ORGANISM: Artificial Sequence
<220> FEATURE:
<223> OTHER INFORMATION: Artificially Synthesized Peptides

<400> SEQUENCE: 86

Lys Ser Arg Ile Met Leu Glu Glu Ile Met Lys Tyr Glu Ala Ser Ile
1               5                   10                  15

Leu Thr His Asp His Arg Gly Gly Pro Glu Glu
            20                  25

<210> SEQ ID NO 87
<211> LENGTH: 27
<212> TYPE: PRT
<213> ORGANISM: Artificial Sequence
<220> FEATURE:
<223> OTHER INFORMATION: Artificially Synthesized Peptides

<400> SEQUENCE: 87

Lys Tyr Glu Ala Ser Ile Leu Thr His Asp Ser Ser Ile Arg Tyr Leu
1               5                   10                  15

Gln Glu Ile Tyr His Arg Gly Gly Pro Glu Glu
            20                  25

<210> SEQ ID NO 88
<211> LENGTH: 27
<212> TYPE: PRT
<213> ORGANISM: Artificial Sequence
<220> FEATURE:
<223> OTHER INFORMATION: Artificially Synthesized Peptides

<400> SEQUENCE: 88

Ser Ser Ile Arg Tyr Leu Gln Glu Ile Tyr Asn Ser Asn Asn Gln Lys
1               5                   10                  15

Ile Val Asn Leu His Arg Gly Gly Pro Glu Glu
            20                  25

<210> SEQ ID NO 89
<211> LENGTH: 27
<212> TYPE: PRT
<213> ORGANISM: Artificial Sequence
<220> FEATURE:
<223> OTHER INFORMATION: Artificially Synthesized Peptides

```
<400> SEQUENCE: 89

Asn Ser Asn Asn Gln Lys Ile Val Asn Leu Lys Glu Lys Val Ala Gln
1               5                   10                  15

Leu Glu Ala Gln His Arg Gly Gly Pro Glu Glu
            20                  25

<210> SEQ ID NO 90
<211> LENGTH: 27
<212> TYPE: PRT
<213> ORGANISM: Artificial Sequence
<220> FEATURE:
<223> OTHER INFORMATION: Artificially Synthesized Peptides

<400> SEQUENCE: 90

Cys Gln Glu Pro Cys Lys Asp Thr Val Gln Ile His Asp Ile Thr Gly
1               5                   10                  15

Lys Asp Cys Gln His Arg Gly Gly Pro Glu Glu
            20                  25

<210> SEQ ID NO 91
<211> LENGTH: 27
<212> TYPE: PRT
<213> ORGANISM: Artificial Sequence
<220> FEATURE:
<223> OTHER INFORMATION: Artificially Synthesized Peptides

<400> SEQUENCE: 91

Ile His Asp Ile Thr Gly Lys Asp Cys Gln Asp Ile Ala Asn Lys Gly
1               5                   10                  15

Ala Lys Gln Ser His Arg Gly Gly Pro Glu Glu
            20                  25

<210> SEQ ID NO 92
<211> LENGTH: 27
<212> TYPE: PRT
<213> ORGANISM: Artificial Sequence
<220> FEATURE:
<223> OTHER INFORMATION: Artificially Synthesized Peptides

<400> SEQUENCE: 92

Asp Ile Ala Asn Lys Gly Ala Lys Gln Ser Gly Leu Tyr Phe Ile Lys
1               5                   10                  15

Pro Leu Lys Ala His Arg Gly Gly Pro Glu Glu
            20                  25

<210> SEQ ID NO 93
<211> LENGTH: 27
<212> TYPE: PRT
<213> ORGANISM: Artificial Sequence
<220> FEATURE:
<223> OTHER INFORMATION: Artificially Synthesized Peptides

<400> SEQUENCE: 93

Gly Leu Tyr Phe Ile Lys Pro Leu Lys Ala Asn Gln Gln Phe Leu Val
1               5                   10                  15

Tyr Cys Glu Ile His Arg Gly Gly Pro Glu Glu
            20                  25

<210> SEQ ID NO 94
<211> LENGTH: 27
<212> TYPE: PRT
<213> ORGANISM: Artificial Sequence
<220> FEATURE:
<223> OTHER INFORMATION: Artificially Synthesized Peptides
```

<400> SEQUENCE: 94

Asn Gln Gln Phe Leu Val Tyr Cys Glu Ile Asp Gly Ser Gly Asn Gly
1               5                   10                  15

Trp Thr Val Phe His Arg Gly Gly Pro Glu Glu
            20                  25

<210> SEQ ID NO 95
<211> LENGTH: 27
<212> TYPE: PRT
<213> ORGANISM: Artificial Sequence
<220> FEATURE:
<223> OTHER INFORMATION: Artificially Synthesized Peptides

<400> SEQUENCE: 95

Asp Gly Ser Gly Asn Gly Trp Thr Val Phe Gln Lys Arg Leu Asp Gly
1               5                   10                  15

Ser Val Asp Phe His Arg Gly Gly Pro Glu Glu
            20                  25

<210> SEQ ID NO 96
<211> LENGTH: 27
<212> TYPE: PRT
<213> ORGANISM: Artificial Sequence
<220> FEATURE:
<223> OTHER INFORMATION: Artificially Synthesized Peptides

<400> SEQUENCE: 96

Gln Lys Arg Leu Asp Gly Ser Val Asp Phe Lys Lys Asn Trp Ile Gln
1               5                   10                  15

Tyr Lys Glu Gly His Arg Gly Gly Pro Glu Glu
            20                  25

<210> SEQ ID NO 97
<211> LENGTH: 27
<212> TYPE: PRT
<213> ORGANISM: Artificial Sequence
<220> FEATURE:
<223> OTHER INFORMATION: Artificially Synthesized Peptides

<400> SEQUENCE: 97

Lys Lys Asn Trp Ile Gln Tyr Lys Glu Gly Phe Gly His Leu Ser Pro
1               5                   10                  15

Thr Gly Thr Thr His Arg Gly Gly Pro Glu Glu
            20                  25

<210> SEQ ID NO 98
<211> LENGTH: 27
<212> TYPE: PRT
<213> ORGANISM: Artificial Sequence
<220> FEATURE:
<223> OTHER INFORMATION: Artificially Synthesized Peptides

<400> SEQUENCE: 98

Phe Gly His Leu Ser Pro Thr Gly Thr Thr Glu Phe Trp Leu Gly Asn
1               5                   10                  15

Glu Lys Ile His His Arg Gly Gly Pro Glu Glu
            20                  25

<210> SEQ ID NO 99
<211> LENGTH: 27
<212> TYPE: PRT
<213> ORGANISM: Artificial Sequence
<220> FEATURE:

<223> OTHER INFORMATION: Artificially Synthesized Peptides

<400> SEQUENCE: 99

Glu Phe Trp Leu Gly Asn Glu Lys Ile His Leu Ile Ser Thr Gln Ser
1               5                   10                  15

Ala Ile Pro Tyr His Arg Gly Gly Pro Glu Glu
                20                  25

<210> SEQ ID NO 100
<211> LENGTH: 27
<212> TYPE: PRT
<213> ORGANISM: Artificial Sequence
<220> FEATURE:
<223> OTHER INFORMATION: Artificially Synthesized Peptides

<400> SEQUENCE: 100

Leu Ile Ser Thr Gln Ser Ala Ile Pro Tyr Ala Leu Arg Val Glu Leu
1               5                   10                  15

Glu Asp Trp Asn His Arg Gly Gly Pro Glu Glu
                20                  25

<210> SEQ ID NO 101
<211> LENGTH: 27
<212> TYPE: PRT
<213> ORGANISM: Artificial Sequence
<220> FEATURE:
<223> OTHER INFORMATION: Artificially Synthesized Peptides

<400> SEQUENCE: 101

Ala Leu Arg Val Glu Leu Glu Asp Trp Asn Gly Arg Thr Ser Thr Ala
1               5                   10                  15

Asp Tyr Ala Met His Arg Gly Gly Pro Glu Glu
                20                  25

<210> SEQ ID NO 102
<211> LENGTH: 27
<212> TYPE: PRT
<213> ORGANISM: Artificial Sequence
<220> FEATURE:
<223> OTHER INFORMATION: Artificially Synthesized Peptides

<400> SEQUENCE: 102

Gly Arg Thr Ser Thr Ala Asp Tyr Ala Met Phe Lys Val Gly Pro Glu
1               5                   10                  15

Ala Asp Lys Tyr His Arg Gly Gly Pro Glu Glu
                20                  25

<210> SEQ ID NO 103
<211> LENGTH: 27
<212> TYPE: PRT
<213> ORGANISM: Artificial Sequence
<220> FEATURE:
<223> OTHER INFORMATION: Artificially Synthesized Peptides

<400> SEQUENCE: 103

Phe Lys Val Gly Pro Glu Ala Asp Lys Tyr Arg Leu Thr Tyr Ala Tyr
1               5                   10                  15

Phe Ala Gly Gly His Arg Gly Gly Pro Glu Glu
                20                  25

<210> SEQ ID NO 104
<211> LENGTH: 27
<212> TYPE: PRT
<213> ORGANISM: Artificial Sequence

```
<220> FEATURE:
<223> OTHER INFORMATION: Artificially Synthesized Peptides

<400> SEQUENCE: 104

Arg Leu Thr Tyr Ala Tyr Phe Ala Gly Gly Asp Ala Gly Asp Ala Phe
1               5                   10                  15

Asp Gly Phe Asp His Arg Gly Gly Pro Glu Glu
            20                  25

<210> SEQ ID NO 105
<211> LENGTH: 27
<212> TYPE: PRT
<213> ORGANISM: Artificial Sequence
<220> FEATURE:
<223> OTHER INFORMATION: Artificially Synthesized Peptides

<400> SEQUENCE: 105

Asp Ala Gly Asp Ala Phe Asp Gly Phe Asp Phe Gly Asp Asp Pro Ser
1               5                   10                  15

Asp Lys Phe Phe His Arg Gly Gly Pro Glu Glu
            20                  25

<210> SEQ ID NO 106
<211> LENGTH: 27
<212> TYPE: PRT
<213> ORGANISM: Artificial Sequence
<220> FEATURE:
<223> OTHER INFORMATION: Artificially Synthesized Peptides

<400> SEQUENCE: 106

Phe Gly Asp Asp Pro Ser Asp Lys Phe Phe Thr Ser His Asn Gly Met
1               5                   10                  15

Gln Phe Ser Thr His Arg Gly Gly Pro Glu Glu
            20                  25

<210> SEQ ID NO 107
<211> LENGTH: 27
<212> TYPE: PRT
<213> ORGANISM: Artificial Sequence
<220> FEATURE:
<223> OTHER INFORMATION: Artificially Synthesized Peptides

<400> SEQUENCE: 107

Thr Ser His Asn Gly Met Gln Phe Ser Thr Trp Asp Asn Asp Asn Asp
1               5                   10                  15

Lys Phe Glu Gly His Arg Gly Gly Pro Glu Glu
            20                  25

<210> SEQ ID NO 108
<211> LENGTH: 27
<212> TYPE: PRT
<213> ORGANISM: Artificial Sequence
<220> FEATURE:
<223> OTHER INFORMATION: Artificially Synthesized Peptides

<400> SEQUENCE: 108

Trp Asp Asn Asp Asn Asp Lys Phe Glu Gly Asn Cys Ala Glu Gln Asp
1               5                   10                  15

Gly Ser Gly Trp His Arg Gly Gly Pro Glu Glu
            20                  25

<210> SEQ ID NO 109
<211> LENGTH: 27
<212> TYPE: PRT
```

```
<213> ORGANISM: Artificial Sequence
<220> FEATURE:
<223> OTHER INFORMATION: Artificially Synthesized Peptides

<400> SEQUENCE: 109

Asn Cys Ala Glu Gln Asp Gly Ser Gly Trp Trp Met Asn Lys Cys His
 1               5                  10                  15

Ala Gly His Leu His Arg Gly Gly Pro Glu Glu
            20                  25

<210> SEQ ID NO 110
<211> LENGTH: 27
<212> TYPE: PRT
<213> ORGANISM: Artificial Sequence
<220> FEATURE:
<223> OTHER INFORMATION: Artificially Synthesized Peptides

<400> SEQUENCE: 110

Trp Met Asn Lys Cys His Ala Gly His Leu Asn Gly Val Tyr Tyr Gln
 1               5                  10                  15

Gly Gly Thr Tyr His Arg Gly Gly Pro Glu Glu
            20                  25

<210> SEQ ID NO 111
<211> LENGTH: 27
<212> TYPE: PRT
<213> ORGANISM: Artificial Sequence
<220> FEATURE:
<223> OTHER INFORMATION: Artificially Synthesized Peptides

<400> SEQUENCE: 111

Asn Gly Val Tyr Tyr Gln Gly Gly Thr Tyr Ser Lys Ala Ser Thr Pro
 1               5                  10                  15

Asn Gly Tyr Asp His Arg Gly Gly Pro Glu Glu
            20                  25

<210> SEQ ID NO 112
<211> LENGTH: 27
<212> TYPE: PRT
<213> ORGANISM: Artificial Sequence
<220> FEATURE:
<223> OTHER INFORMATION: Artificially Synthesized Peptides

<400> SEQUENCE: 112

Ser Lys Ala Ser Thr Pro Asn Gly Tyr Asp Asn Gly Ile Ile Trp Ala
 1               5                  10                  15

Thr Trp Lys Thr His Arg Gly Gly Pro Glu Glu
            20                  25

<210> SEQ ID NO 113
<211> LENGTH: 27
<212> TYPE: PRT
<213> ORGANISM: Artificial Sequence
<220> FEATURE:
<223> OTHER INFORMATION: Artificially Synthesized Peptides

<400> SEQUENCE: 113

Asn Gly Ile Ile Trp Ala Thr Trp Lys Thr Arg Trp Tyr Ser Met Lys
 1               5                  10                  15

Lys Thr Thr Met His Arg Gly Gly Pro Glu Glu
            20                  25

<210> SEQ ID NO 114
<211> LENGTH: 27
```

```
<212> TYPE: PRT
<213> ORGANISM: Artificial Sequence
<220> FEATURE:
<223> OTHER INFORMATION: Artificially Synthesized Peptides

<400> SEQUENCE: 114

Arg Trp Tyr Ser Met Lys Lys Thr Thr Met Lys Ile Ile Pro Phe Asn
1               5                   10                  15

Arg Leu Thr Ile His Arg Gly Gly Pro Glu Glu
            20                  25

<210> SEQ ID NO 115
<211> LENGTH: 34
<212> TYPE: PRT
<213> ORGANISM: Artificial Sequence
<220> FEATURE:
<223> OTHER INFORMATION: Artificially Synthesized Peptides

<400> SEQUENCE: 115

Lys Ile Ile Pro Phe Asn Arg Leu Thr Ile Gly Glu Gly Gln Gln His
1               5                   10                  15

His Leu Gly Gly Ala Lys Gln Ala Gly Asp Val His Arg Gly Gly Pro
            20                  25                  30

Glu Glu

<210> SEQ ID NO 116
<211> LENGTH: 7
<212> TYPE: PRT
<213> ORGANISM: Artificial Sequence
<220> FEATURE:
<223> OTHER INFORMATION: Artificially Synthesized Peptides

<400> SEQUENCE: 116

Pro Asn Ala Pro Ile Leu Ser
1               5

<210> SEQ ID NO 117
<211> LENGTH: 10
<212> TYPE: PRT
<213> ORGANISM: Artificial Sequence
<220> FEATURE:
<223> OTHER INFORMATION: Artificially Synthesized Peptides

<400> SEQUENCE: 117

His Leu Gly Gly Ala Lys Gln Ala Gly Asp
1               5                   10

<210> SEQ ID NO 118
<211> LENGTH: 22
<212> TYPE: PRT
<213> ORGANISM: Artificial Sequence
<220> FEATURE:
<223> OTHER INFORMATION: Artificially Synthesized Peptides

<400> SEQUENCE: 118

Cys Asp Leu Ile Tyr Tyr Asp Tyr Glu Glu Asp Tyr Tyr Phe Pro Pro
1               5                   10                  15

Asn Ala Pro Ile Leu Ser
            20

<210> SEQ ID NO 119
<211> LENGTH: 24
<212> TYPE: PRT
<213> ORGANISM: Artificial Sequence
<220> FEATURE:
```

-continued

<223> OTHER INFORMATION: Artificially Synthesized Peptides

<400> SEQUENCE: 119

Cys Asp Leu Ile Tyr Tyr Asp Tyr Glu Glu Asp Tyr Tyr Phe Arg Pro
1               5                   10                  15

Pro Asn Ala Pro Ile Leu Ser Thr
            20

<210> SEQ ID NO 120
<211> LENGTH: 26
<212> TYPE: PRT
<213> ORGANISM: Artificial Sequence
<220> FEATURE:
<223> OTHER INFORMATION: Artificially Synthesized Peptides

<400> SEQUENCE: 120

Cys Asp Leu Ile Tyr Tyr Asp Tyr Glu Glu Asp Tyr Tyr Phe Lys Glu
1               5                   10                  15

Ile Pro Ala Leu Thr Ala Val Glu Thr Gly
            20                  25

<210> SEQ ID NO 121
<211> LENGTH: 26
<212> TYPE: PRT
<213> ORGANISM: Artificial Sequence
<220> FEATURE:
<223> OTHER INFORMATION: Artificially Synthesized Peptides

<400> SEQUENCE: 121

Cys Asp Leu Ile Tyr Tyr Asp Tyr Glu Glu Asp Tyr Tyr Phe Pro Ala
1               5                   10                  15

His Ser Lys Glu Ile Pro Ala Leu Thr Ala
            20                  25

<210> SEQ ID NO 122
<211> LENGTH: 24
<212> TYPE: PRT
<213> ORGANISM: Artificial Sequence
<220> FEATURE:
<223> OTHER INFORMATION: Artificially Synthesized Peptides

<400> SEQUENCE: 122

Cys Asp Leu Ile Tyr Tyr Asp Tyr Glu Glu Asp Tyr Tyr Phe Trp Gly
1               5                   10                  15

Cys Ser Gly Lys Leu Ile Cys Thr
            20

<210> SEQ ID NO 123
<211> LENGTH: 24
<212> TYPE: PRT
<213> ORGANISM: Artificial Sequence
<220> FEATURE:
<223> OTHER INFORMATION: Artificially Synthesized Peptides

<400> SEQUENCE: 123

Cys Asp Leu Ile Tyr Tyr Asp Tyr Glu Glu Asp Tyr Tyr Phe Cys Thr
1               5                   10                  15

Thr Ala Val Pro Trp Asn Ala Ser
            20

<210> SEQ ID NO 124
<211> LENGTH: 39
<212> TYPE: PRT
<213> ORGANISM: Artificial Sequence

```
<220> FEATURE:
<223> OTHER INFORMATION: Artificially Synthesized Peptides

<400> SEQUENCE: 124

Cys Asp Leu Ile Tyr Tyr Asp Tyr Glu Glu Asp Tyr Tyr Phe Lys Arg
 1               5                  10                  15

Pro Pro Asn Ala Pro Ile Leu Ser Thr Cys Asp Leu Ile Tyr Tyr Asp
             20                  25                  30

Tyr Glu Glu Asp Tyr Tyr Phe
             35

<210> SEQ ID NO 125
<211> LENGTH: 13
<212> TYPE: PRT
<213> ORGANISM: Artificial Sequence
<220> FEATURE:
<223> OTHER INFORMATION: Artificially Synthesized Peptides

<400> SEQUENCE: 125

Thr Tyr Ala Met Asn Pro Pro Asn Ala Pro Ile Leu Ser
 1               5                  10

<210> SEQ ID NO 126
<211> LENGTH: 27
<212> TYPE: PRT
<213> ORGANISM: Artificial Sequence
<220> FEATURE:
<223> OTHER INFORMATION: Artificially Synthesized Peptides

<400> SEQUENCE: 126

Arg Val Arg Ser Lys Ser Phe Asn Tyr Ala Thr Tyr Tyr Ala Asp Ser
 1               5                  10                  15

Val Lys Gly Pro Pro Asn Ala Pro Ile Leu Ser
             20                  25

<210> SEQ ID NO 127
<211> LENGTH: 22
<212> TYPE: PRT
<213> ORGANISM: Artificial Sequence
<220> FEATURE:
<223> OTHER INFORMATION: Artificially Synthesized Peptides

<400> SEQUENCE: 127

Pro Ala Gln Gly Ile Tyr Phe Asp Tyr Gly Gly Phe Ala Tyr Pro Pro
 1               5                  10                  15

Asn Ala Pro Ile Leu Ser
             20

<210> SEQ ID NO 128
<211> LENGTH: 24
<212> TYPE: PRT
<213> ORGANISM: Artificial Sequence
<220> FEATURE:
<223> OTHER INFORMATION: Artificially Synthesized Peptides

<400> SEQUENCE: 128

Cys Asp Leu Ile Tyr Tyr Asp Tyr Glu Glu Asp Tyr Tyr Gln Arg Lys
 1               5                  10                  15

Thr Lys Arg Asn Thr Asn Arg Arg
             20

<210> SEQ ID NO 129
<211> LENGTH: 10
<212> TYPE: PRT
```

```
<213> ORGANISM: Artificial Sequence
<220> FEATURE:
<223> OTHER INFORMATION: Artificially Synthesized Peptides

<400> SEQUENCE: 129

Ala Leu Gly Gly Ala Lys Gln Ala Gly Asp
1               5                   10

<210> SEQ ID NO 130
<211> LENGTH: 20
<212> TYPE: PRT
<213> ORGANISM: Artificial Sequence
<220> FEATURE:
<223> OTHER INFORMATION: Artificially Synthesized Peptides

<400> SEQUENCE: 130

Leu Thr Ile Gly Glu Gly Gln Gln His His Leu Gly Gly Ala Lys Gln
1               5                   10                  15

Ala Gly Asp Val
            20

<210> SEQ ID NO 131
<211> LENGTH: 17
<212> TYPE: PRT
<213> ORGANISM: Artificial Sequence
<220> FEATURE:
<223> OTHER INFORMATION: Artificially Synthesized Peptides

<400> SEQUENCE: 131

Gly Glu Gly Gln Gln His His Leu Gly Gly Ala Lys Gln Ala Gly Asp
1               5                   10                  15

Val

<210> SEQ ID NO 132
<211> LENGTH: 14
<212> TYPE: PRT
<213> ORGANISM: Artificial Sequence
<220> FEATURE:
<223> OTHER INFORMATION: Artificially Synthesized Peptides

<400> SEQUENCE: 132

Gln Gln His His Leu Gly Gly Ala Lys Gln Ala Gly Asp Val
1               5                   10

<210> SEQ ID NO 133
<211> LENGTH: 13
<212> TYPE: PRT
<213> ORGANISM: Artificial Sequence
<220> FEATURE:
<223> OTHER INFORMATION: Artificially Synthesized Peptides

<400> SEQUENCE: 133

Gln His His Leu Gly Gly Ala Lys Gln Ala Gly Asp Val
1               5                   10

<210> SEQ ID NO 134
<211> LENGTH: 12
<212> TYPE: PRT
<213> ORGANISM: Artificial Sequence
<220> FEATURE:
<223> OTHER INFORMATION: Artificially Synthesized Peptides

<400> SEQUENCE: 134

His His Leu Gly Gly Ala Lys Gln Ala Gly Asp Val
1               5                   10
```

```
<210> SEQ ID NO 135
<211> LENGTH: 11
<212> TYPE: PRT
<213> ORGANISM: Artificial Sequence
<220> FEATURE:
<223> OTHER INFORMATION: Artificially Synthesized Peptides

<400> SEQUENCE: 135

His Leu Gly Gly Ala Lys Gln Ala Gly Asp Val
 1               5                  10

<210> SEQ ID NO 136
<211> LENGTH: 10
<212> TYPE: PRT
<213> ORGANISM: Artificial Sequence
<220> FEATURE:
<223> OTHER INFORMATION: Artificially Synthesized Peptides

<400> SEQUENCE: 136

Leu Gly Gly Ala Lys Gln Ala Gly Asp Val
 1               5                  10

<210> SEQ ID NO 137
<211> LENGTH: 9
<212> TYPE: PRT
<213> ORGANISM: Artificial Sequence
<220> FEATURE:
<223> OTHER INFORMATION: Artificially Synthesized Peptides

<400> SEQUENCE: 137

Gly Gly Ala Lys Gln Ala Gly Asp Val
 1               5

<210> SEQ ID NO 138
<211> LENGTH: 8
<212> TYPE: PRT
<213> ORGANISM: Artificial Sequence
<220> FEATURE:
<223> OTHER INFORMATION: Artificially Synthesized Peptides

<400> SEQUENCE: 138

Gly Ala Lys Gln Ala Gly Asp Val
 1               5

<210> SEQ ID NO 139
<211> LENGTH: 12
<212> TYPE: PRT
<213> ORGANISM: Artificial Sequence
<220> FEATURE:
<223> OTHER INFORMATION: Artificially Synthesized Peptides

<400> SEQUENCE: 139

Gln His His Leu Gly Gly Ala Lys Gln Ala Gly Asp
 1               5                  10

<210> SEQ ID NO 140
<211> LENGTH: 11
<212> TYPE: PRT
<213> ORGANISM: Artificial Sequence
<220> FEATURE:
<223> OTHER INFORMATION: Artificially Synthesized Peptides

<400> SEQUENCE: 140

Gln His His Leu Gly Gly Ala Lys Gln Ala Gly
 1               5                  10
```

<210> SEQ ID NO 141
<211> LENGTH: 10
<212> TYPE: PRT
<213> ORGANISM: Artificial Sequence
<220> FEATURE:
<223> OTHER INFORMATION: Artificially Synthesized Peptides

<400> SEQUENCE: 141

Gln His His Leu Gly Gly Ala Lys Gln Ala
1               5                   10

<210> SEQ ID NO 142
<211> LENGTH: 9
<212> TYPE: PRT
<213> ORGANISM: Artificial Sequence
<220> FEATURE:
<223> OTHER INFORMATION: Artificially Synthesized Peptides

<400> SEQUENCE: 142

Gln His His Leu Gly Gly Ala Lys Gln
1               5

<210> SEQ ID NO 143
<211> LENGTH: 8
<212> TYPE: PRT
<213> ORGANISM: Artificial Sequence
<220> FEATURE:
<223> OTHER INFORMATION: Artificially Synthesized Peptides

<400> SEQUENCE: 143

Gln His His Leu Gly Gly Ala Lys
1               5

<210> SEQ ID NO 144
<211> LENGTH: 7
<212> TYPE: PRT
<213> ORGANISM: Artificial Sequence
<220> FEATURE:
<223> OTHER INFORMATION: Artificially Synthesized Peptides

<400> SEQUENCE: 144

Gln His His Leu Gly Gly Ala
1               5

<210> SEQ ID NO 145
<211> LENGTH: 12
<212> TYPE: PRT
<213> ORGANISM: Artificial Sequence
<220> FEATURE:
<223> OTHER INFORMATION: Artificially Synthesized Peptides

<400> SEQUENCE: 145

His His Leu Gly Gly Ala Lys Gln Ala Gly Asp Val
1               5                   10

<210> SEQ ID NO 146
<211> LENGTH: 11
<212> TYPE: PRT
<213> ORGANISM: Artificial Sequence
<220> FEATURE:
<223> OTHER INFORMATION: Artificially Synthesized Peptides

<400> SEQUENCE: 146

His His Leu Gly Gly Ala Lys Gln Ala Gly Asp
1               5                   10

<210> SEQ ID NO 147

```
<211> LENGTH: 10
<212> TYPE: PRT
<213> ORGANISM: Artificial Sequence
<220> FEATURE:
<223> OTHER INFORMATION: Artificially Synthesized Peptides

<400> SEQUENCE: 147

His His Leu Gly Gly Ala Lys Gln Ala Gly
 1               5                  10

<210> SEQ ID NO 148
<211> LENGTH: 11
<212> TYPE: PRT
<213> ORGANISM: Artificial Sequence
<220> FEATURE:
<223> OTHER INFORMATION: Artificially Synthesized Peptides

<400> SEQUENCE: 148

His Leu Gly Gly Ala Lys Gln Ala Gly Asp Val
 1               5                  10

<210> SEQ ID NO 149
<211> LENGTH: 10
<212> TYPE: PRT
<213> ORGANISM: Artificial Sequence
<220> FEATURE:
<223> OTHER INFORMATION: Artificially Synthesized Peptides

<400> SEQUENCE: 149

His Leu Gly Gly Ala Lys Gln Ala Gly Asp
 1               5                  10

<210> SEQ ID NO 150
<211> LENGTH: 9
<212> TYPE: PRT
<213> ORGANISM: Artificial Sequence
<220> FEATURE:
<223> OTHER INFORMATION: Artificially Synthesized Peptides

<400> SEQUENCE: 150

Ala Leu Gly Gly Ala Lys Gln Ala Gly
 1               5

<210> SEQ ID NO 151
<211> LENGTH: 9
<212> TYPE: PRT
<213> ORGANISM: Artificial Sequence
<220> FEATURE:
<223> OTHER INFORMATION: Artificially Synthesized Peptides

<400> SEQUENCE: 151

His Ala Gly Gly Ala Lys Gln Ala Gly
 1               5

<210> SEQ ID NO 152
<211> LENGTH: 9
<212> TYPE: PRT
<213> ORGANISM: Artificial Sequence
<220> FEATURE:
<223> OTHER INFORMATION: Artificially Synthesized Peptides

<400> SEQUENCE: 152

His Leu Ala Gly Ala Lys Gln Ala Gly
 1               5

<210> SEQ ID NO 153
<211> LENGTH: 9
```

```
<212> TYPE: PRT
<213> ORGANISM: Artificial Sequence
<220> FEATURE:
<223> OTHER INFORMATION: Artificially Synthesized Peptides

<400> SEQUENCE: 153

His Leu Gly Ala Ala Lys Gln Ala Gly
 1               5

<210> SEQ ID NO 154
<211> LENGTH: 9
<212> TYPE: PRT
<213> ORGANISM: Artificial Sequence
<220> FEATURE:
<223> OTHER INFORMATION: Artificially Synthesized Peptides

<400> SEQUENCE: 154

His Leu Gly Gly Gly Lys Gln Ala Gly
 1               5

<210> SEQ ID NO 155
<211> LENGTH: 9
<212> TYPE: PRT
<213> ORGANISM: Artificial Sequence
<220> FEATURE:
<223> OTHER INFORMATION: Artificially Synthesized Peptides

<400> SEQUENCE: 155

His Leu Gly Gly Ala Ala Gln Ala Gly
 1               5

<210> SEQ ID NO 156
<211> LENGTH: 9
<212> TYPE: PRT
<213> ORGANISM: Artificial Sequence
<220> FEATURE:
<223> OTHER INFORMATION: Artificially Synthesized Peptides

<400> SEQUENCE: 156

His Leu Gly Gly Ala Lys Ala Ala Gly
 1               5

<210> SEQ ID NO 157
<211> LENGTH: 9
<212> TYPE: PRT
<213> ORGANISM: Artificial Sequence
<220> FEATURE:
<223> OTHER INFORMATION: Artificially Synthesized Peptides

<400> SEQUENCE: 157

His Leu Gly Gly Ala Lys Gln Gly Gly
 1               5

<210> SEQ ID NO 158
<211> LENGTH: 9
<212> TYPE: PRT
<213> ORGANISM: Artificial Sequence
<220> FEATURE:
<223> OTHER INFORMATION: Artificially Synthesized Peptides

<400> SEQUENCE: 158

His Leu Gly Gly Ala Lys Gln Ala Ala
 1               5

<210> SEQ ID NO 159
<211> LENGTH: 19
<212> TYPE: PRT
```

```
<213> ORGANISM: Artificial Sequence
<220> FEATURE:
<223> OTHER INFORMATION: Artificially Synthesized Peptides

<400> SEQUENCE: 159

His Arg Gly Gly Pro Glu Glu Phe His His Leu Gly Gly Ala Lys Gln
 1               5                   10                  15

Ala Gly Asp

<210> SEQ ID NO 160
<211> LENGTH: 19
<212> TYPE: PRT
<213> ORGANISM: Artificial Sequence
<220> FEATURE:
<223> OTHER INFORMATION: Artificially Synthesized Peptides

<400> SEQUENCE: 160

His Arg Gly Gly Pro Glu Glu Phe His His Leu Gly Gly Ala Lys Arg
 1               5                   10                  15

Ala Gly Arg

<210> SEQ ID NO 161
<211> LENGTH: 19
<212> TYPE: PRT
<213> ORGANISM: Artificial Sequence
<220> FEATURE:
<223> OTHER INFORMATION: Artificially Synthesized Peptides

<400> SEQUENCE: 161

His Arg Gly Gly Pro Glu Glu Phe His His Leu Gly Gly Ala Arg Arg
 1               5                   10                  15

Ala Gly Arg

<210> SEQ ID NO 162
<211> LENGTH: 19
<212> TYPE: PRT
<213> ORGANISM: Artificial Sequence
<220> FEATURE:
<223> OTHER INFORMATION: Artificially Synthesized Peptides

<400> SEQUENCE: 162

His Arg Gly Gly Pro Glu Glu Phe His His Leu Gly His Ala Lys Gln
 1               5                   10                  15

Ala Gly Arg

<210> SEQ ID NO 163
<211> LENGTH: 19
<212> TYPE: PRT
<213> ORGANISM: Artificial Sequence
<220> FEATURE:
<223> OTHER INFORMATION: Artificially Synthesized Peptides

<400> SEQUENCE: 163

His Arg Gly Gly Pro Glu Glu Phe His His Leu Gly His Ala Arg Gln
 1               5                   10                  15

Ala Gly Arg

<210> SEQ ID NO 164
<211> LENGTH: 19
<212> TYPE: PRT
<213> ORGANISM: Artificial Sequence
<220> FEATURE:
<223> OTHER INFORMATION: Artificially Synthesized Peptides
```

-continued

```
<400> SEQUENCE: 164

His Arg Gly Gly Pro Glu Glu Phe His His Leu Gly His Ala Lys Arg
1               5                   10                  15

Ala Gly Leu

<210> SEQ ID NO 165
<211> LENGTH: 19
<212> TYPE: PRT
<213> ORGANISM: Artificial Sequence
<220> FEATURE:
<223> OTHER INFORMATION: Artificially Synthesized Peptides

<400> SEQUENCE: 165

His Arg Gly Gly Pro Glu Glu Phe His His Leu Gly His Ala Lys Arg
1               5                   10                  15

Ala Gly Arg

<210> SEQ ID NO 166
<211> LENGTH: 19
<212> TYPE: PRT
<213> ORGANISM: Artificial Sequence
<220> FEATURE:
<223> OTHER INFORMATION: Artificially Synthesized Peptides

<400> SEQUENCE: 166

His His Leu Gly Gly Ala Lys Gln Ala Gly Asp His Arg Gly Gly Pro
1               5                   10                  15

Glu Glu Phe

<210> SEQ ID NO 167
<211> LENGTH: 19
<212> TYPE: PRT
<213> ORGANISM: Artificial Sequence
<220> FEATURE:
<223> OTHER INFORMATION: Artificially Synthesized Peptides

<400> SEQUENCE: 167

His His Leu Gly Gly Ala Lys Arg Ala Gly Arg His Arg Gly Gly Pro
1               5                   10                  15

Glu Glu Phe

<210> SEQ ID NO 168
<211> LENGTH: 19
<212> TYPE: PRT
<213> ORGANISM: Artificial Sequence
<220> FEATURE:
<223> OTHER INFORMATION: Artificially Synthesized Peptides

<400> SEQUENCE: 168

His His Leu Gly Gly Ala Arg Arg Ala Gly Arg His Arg Gly Gly Pro
1               5                   10                  15

Glu Glu Phe

<210> SEQ ID NO 169
<211> LENGTH: 19
<212> TYPE: PRT
<213> ORGANISM: Artificial Sequence
<220> FEATURE:
<223> OTHER INFORMATION: Artificially Synthesized Peptides

<400> SEQUENCE: 169

His His Leu Gly His Ala Lys Gln Ala Gly Arg His Arg Gly Gly Pro
1               5                   10                  15
```

```
<210> SEQ ID NO 170
<211> LENGTH: 19
<212> TYPE: PRT
<213> ORGANISM: Artificial Sequence
<220> FEATURE:
<223> OTHER INFORMATION: Artificially Synthesized Peptides

<400> SEQUENCE: 170

His His Leu Gly His Ala Arg Gln Ala Gly Arg His Arg Gly Gly Pro
 1               5                  10                  15

Glu Glu Phe

<210> SEQ ID NO 171
<211> LENGTH: 19
<212> TYPE: PRT
<213> ORGANISM: Artificial Sequence
<220> FEATURE:
<223> OTHER INFORMATION: Artificially Synthesized Peptides

<400> SEQUENCE: 171

His His Leu Gly His Ala Lys Arg Ala Gly Leu His Arg Gly Gly Pro
 1               5                  10                  15

Glu Glu Phe

<210> SEQ ID NO 172
<211> LENGTH: 19
<212> TYPE: PRT
<213> ORGANISM: Artificial Sequence
<220> FEATURE:
<223> OTHER INFORMATION: Artificially Synthesized Peptides

<400> SEQUENCE: 172

His His Leu Gly His Ala Lys Arg Ala Gly Arg His Arg Gly Gly Pro
 1               5                  10                  15

Glu Glu Phe

<210> SEQ ID NO 173
<211> LENGTH: 25
<212> TYPE: PRT
<213> ORGANISM: Artificial Sequence
<220> FEATURE:
<223> OTHER INFORMATION: Artificially Synthesized Peptides

<400> SEQUENCE: 173

Pro Ala Leu Thr Ala Val Glu Thr Gly Ala Thr Asn Pro Leu His His
 1               5                  10                  15

Leu Gly Gly Ala Lys Gln Ala Gly Asp
             20                  25

<210> SEQ ID NO 174
<211> LENGTH: 25
<212> TYPE: PRT
<213> ORGANISM: Artificial Sequence
<220> FEATURE:
<223> OTHER INFORMATION: Artificially Synthesized Peptides

<400> SEQUENCE: 174

Pro Ala Leu Thr Ala Val Glu Thr Gly Ala Thr Asn Pro Leu His His
 1               5                  10                  15

Leu Gly Gly Ala Lys Arg Ala Gly Arg
             20                  25
```

<210> SEQ ID NO 175
<211> LENGTH: 25
<212> TYPE: PRT
<213> ORGANISM: Artificial Sequence
<220> FEATURE:
<223> OTHER INFORMATION: Artificially Synthesized Peptides

<400> SEQUENCE: 175

Pro Ala Leu Thr Ala Val Glu Thr Gly Ala Thr Asn Pro Leu His His
1               5                   10                  15

Leu Gly Gly Ala Arg Arg Ala Gly Arg
            20                  25

<210> SEQ ID NO 176
<211> LENGTH: 25
<212> TYPE: PRT
<213> ORGANISM: Artificial Sequence
<220> FEATURE:
<223> OTHER INFORMATION: Artificially Synthesized Peptides

<400> SEQUENCE: 176

Pro Ala Leu Thr Ala Val Glu Thr Gly Ala Thr Asn Pro Leu His His
1               5                   10                  15

Leu Gly His Ala Lys Gln Ala Gly Arg
            20                  25

<210> SEQ ID NO 177
<211> LENGTH: 25
<212> TYPE: PRT
<213> ORGANISM: Artificial Sequence
<220> FEATURE:
<223> OTHER INFORMATION: Artificially Synthesized Peptides

<400> SEQUENCE: 177

Pro Ala Leu Thr Ala Val Glu Thr Gly Ala Thr Asn Pro Leu His His
1               5                   10                  15

Leu Gly His Ala Arg Gln Ala Gly Arg
            20                  25

<210> SEQ ID NO 178
<211> LENGTH: 25
<212> TYPE: PRT
<213> ORGANISM: Artificial Sequence
<220> FEATURE:
<223> OTHER INFORMATION: Artificially Synthesized Peptides

<400> SEQUENCE: 178

Pro Ala Leu Thr Ala Val Glu Thr Gly Ala Thr Asn Pro Leu His His
1               5                   10                  15

Leu Gly His Ala Lys Arg Ala Gly Leu
            20                  25

<210> SEQ ID NO 179
<211> LENGTH: 25
<212> TYPE: PRT
<213> ORGANISM: Artificial Sequence
<220> FEATURE:
<223> OTHER INFORMATION: Artificially Synthesized Peptides

<400> SEQUENCE: 179

Pro Ala Leu Thr Ala Val Glu Thr Gly Ala Thr Asn Pro Leu His His
1               5                   10                  15

Leu Gly His Ala Lys Arg Ala Gly Arg 20                  25

<210> SEQ ID NO 180
<211> LENGTH: 25
<212> TYPE: PRT
<213> ORGANISM: Artificial Sequence
<220> FEATURE:
<223> OTHER INFORMATION: Artificially Synthesized Peptides

<400> SEQUENCE: 180

His His Leu Gly Gly Ala Lys Gln Ala Gly Asp Pro Ala Leu Thr Ala
 1               5                  10                  15

Val Glu Thr Gly Ala Thr Asn Pro Leu
            20                  25

<210> SEQ ID NO 181
<211> LENGTH: 25
<212> TYPE: PRT
<213> ORGANISM: Artificial Sequence
<220> FEATURE:
<223> OTHER INFORMATION: Artificially Synthesized Peptides

<400> SEQUENCE: 181

His His Leu Gly Gly Ala Lys Arg Ala Gly Arg Pro Ala Leu Thr Ala
 1               5                  10                  15

Val Glu Thr Gly Ala Thr Asn Pro Leu
            20                  25

<210> SEQ ID NO 182
<211> LENGTH: 25
<212> TYPE: PRT
<213> ORGANISM: Artificial Sequence
<220> FEATURE:
<223> OTHER INFORMATION: Artificially Synthesized Peptides

<400> SEQUENCE: 182

His His Leu Gly Gly Ala Arg Arg Ala Gly Arg Pro Ala Leu Thr Ala
 1               5                  10                  15

Val Glu Thr Gly Ala Thr Asn Pro Leu
            20                  25

<210> SEQ ID NO 183
<211> LENGTH: 25
<212> TYPE: PRT
<213> ORGANISM: Artificial Sequence
<220> FEATURE:
<223> OTHER INFORMATION: Artificially Synthesized Peptides

<400> SEQUENCE: 183

His His Leu Gly His Ala Lys Gln Ala Gly Arg Pro Ala Leu Thr Ala
 1               5                  10                  15

Val Glu Thr Gly Ala Thr Asn Pro Leu
            20                  25

<210> SEQ ID NO 184
<211> LENGTH: 25
<212> TYPE: PRT
<213> ORGANISM: Artificial Sequence
<220> FEATURE:
<223> OTHER INFORMATION: Artificially Synthesized Peptides

<400> SEQUENCE: 184

His His Leu Gly His Ala Arg Gln Ala Gly Arg Pro Ala Leu Thr Ala
 1               5                  10                  15

```
Val Glu Thr Gly Ala Thr Asn Pro Leu
            20                  25

<210> SEQ ID NO 185
<211> LENGTH: 25
<212> TYPE: PRT
<213> ORGANISM: Artificial Sequence
<220> FEATURE:
<223> OTHER INFORMATION: Artificially Synthesized Peptides

<400> SEQUENCE: 185

His His Leu Gly His Ala Lys Arg Ala Gly Leu Pro Ala Leu Thr Ala
 1               5                  10                  15

Val Glu Thr Gly Ala Thr Asn Pro Leu
            20                  25

<210> SEQ ID NO 186
<211> LENGTH: 25
<212> TYPE: PRT
<213> ORGANISM: Artificial Sequence
<220> FEATURE:
<223> OTHER INFORMATION: Artificially Synthesized Peptides

<400> SEQUENCE: 186

His His Leu Gly His Ala Lys Arg Ala Gly Arg Pro Ala Leu Thr Ala
 1               5                  10                  15

Val Glu Thr Gly Ala Thr Asn Pro Leu
            20                  25

<210> SEQ ID NO 187
<211> LENGTH: 27
<212> TYPE: PRT
<213> ORGANISM: Artificial Sequence
<220> FEATURE:
<223> OTHER INFORMATION: Artificially Synthesized Peptides

<400> SEQUENCE: 187

Cys Pro Ala Leu Thr Ala Val Glu Thr Gly Cys Thr Asn Pro Leu Ala
 1               5                  10                  15

Ala His His Leu Gly Gly Ala Lys Gln Ala Gly
            20                  25

<210> SEQ ID NO 188
<211> LENGTH: 27
<212> TYPE: PRT
<213> ORGANISM: Artificial Sequence
<220> FEATURE:
<223> OTHER INFORMATION: Artificially Synthesized Peptides

<400> SEQUENCE: 188

His His Leu Gly Gly Ala Lys Gln Ala Gly Ala Ala Cys Pro Ala Leu
 1               5                  10                  15

Thr Ala Val Glu Thr Gly Cys Thr Asn Pro Leu
            20                  25

<210> SEQ ID NO 189
<211> LENGTH: 25
<212> TYPE: PRT
<213> ORGANISM: Artificial Sequence
<220> FEATURE:
<223> OTHER INFORMATION: Artificially Synthesized Peptides

<400> SEQUENCE: 189

Cys Pro Ala Leu Thr Ala Val Glu Thr Gly Cys Thr Asn Pro Leu His
 1               5                  10                  15
```

```
His Leu Gly Gly Ala Lys Gln Ala Gly
            20                  25

<210> SEQ ID NO 190
<211> LENGTH: 25
<212> TYPE: PRT
<213> ORGANISM: Artificial Sequence
<220> FEATURE:
<223> OTHER INFORMATION: Artificially Synthesized Peptides

<400> SEQUENCE: 190

His His Leu Gly Gly Ala Lys Gln Ala Gly Cys Pro Ala Leu Thr Ala
 1               5                  10                  15

Val Glu Thr Gly Cys Thr Asn Pro Leu
            20                  25

<210> SEQ ID NO 191
<211> LENGTH: 27
<212> TYPE: PRT
<213> ORGANISM: Artificial Sequence
<220> FEATURE:
<223> OTHER INFORMATION: Artificially Synthesized Peptides

<400> SEQUENCE: 191

His His Leu Gly Gly Ala Lys Gln Ala Gly Ala Ala Cys Pro Ala Leu
 1               5                  10                  15

Thr Ala Val Glu Thr Gly Cys Thr Asn Pro Leu
            20                  25

<210> SEQ ID NO 192
<211> LENGTH: 27
<212> TYPE: PRT
<213> ORGANISM: Artificial Sequence
<220> FEATURE:
<223> OTHER INFORMATION: Artificially Synthesized Peptides

<400> SEQUENCE: 192

Cys Pro Ala Leu Thr Ala Val Glu Thr Gly Cys Thr Asn Pro Leu Ala
 1               5                  10                  15

Ala His His Leu Gly Gly Ala Lys Gln Ala Gly
            20                  25

<210> SEQ ID NO 193
<211> LENGTH: 25
<212> TYPE: PRT
<213> ORGANISM: Artificial Sequence
<220> FEATURE:
<223> OTHER INFORMATION: Artificially Synthesized Peptides

<400> SEQUENCE: 193

Cys Pro Ala Leu Thr Ala Val Glu Thr Gly Cys Thr Asn Pro Leu His
 1               5                  10                  15

His Leu Gly Gly Ala Lys Gln Ala Gly
            20                  25

<210> SEQ ID NO 194
<211> LENGTH: 25
<212> TYPE: PRT
<213> ORGANISM: Artificial Sequence
<220> FEATURE:
<223> OTHER INFORMATION: Artificially Synthesized Peptides

<400> SEQUENCE: 194

His His Leu Gly Gly Ala Lys Gln Ala Gly Cys Pro Ala Leu Thr Ala
```

```
                1               5                  10                 15
Val Glu Thr Gly Cys Thr Asn Pro Leu
                20                  25
```

<210> SEQ ID NO 195
<211> LENGTH: 24
<212> TYPE: PRT
<213> ORGANISM: Artificial Sequence
<220> FEATURE:
<223> OTHER INFORMATION: Artificially Synthesized Peptides

<400> SEQUENCE: 195

```
Pro Ala Leu Thr Ala Val Glu Thr Gly Ala Thr Asn Pro Leu His His
 1               5                  10                  15
Leu Gly Gly Ala Lys Gln Ala Gly
                20
```

<210> SEQ ID NO 196
<211> LENGTH: 24
<212> TYPE: PRT
<213> ORGANISM: Artificial Sequence
<220> FEATURE:
<223> OTHER INFORMATION: Artificially Synthesized Peptides

<400> SEQUENCE: 196

```
His His Leu Gly Gly Ala Lys Gln Ala Gly Pro Ala Leu Thr Ala Val
 1               5                  10                  15
Glu Thr Gly Ala Thr Asn Pro Leu
                20
```

<210> SEQ ID NO 197
<211> LENGTH: 13
<212> TYPE: PRT
<213> ORGANISM: Artificial Sequence
<220> FEATURE:
<223> OTHER INFORMATION: Artificially Synthesized Peptides

<400> SEQUENCE: 197

```
Gly Arg Gly Asp Ser Pro His Arg Gly Gly Pro Glu Glu
 1               5                  10
```

<210> SEQ ID NO 198
<211> LENGTH: 13
<212> TYPE: PRT
<213> ORGANISM: Artificial Sequence
<220> FEATURE:
<223> OTHER INFORMATION: Artificially Synthesized Peptides

<400> SEQUENCE: 198

```
Trp Ser Arg Gly Asp Trp His Arg Gly Gly Pro Glu Glu
 1               5                  10
```

<210> SEQ ID NO 199
<211> LENGTH: 12
<212> TYPE: PRT
<213> ORGANISM: Artificial Sequence
<220> FEATURE:
<223> OTHER INFORMATION: Artificially Synthesized Peptides

<400> SEQUENCE: 199

```
Arg Gly Asp Ser Ala Ala Thr Pro Pro Ala Tyr Arg
 1               5                  10
```

SPECIFICITY EXCHANGERS THAT REDIRECT ANTIBODIES TO BACTERIAL ADHESION RECEPTORS

CROSS-REFERENCE TO RELATED APPLICATIONS

The present application is a Continuation-In-Part of prior U.S. application Ser. No. 10/234,579, filed Aug. 30, 2002, which is a continuation of prior U.S. application Ser. No. 09/839,666, filed Apr. 19, 2001 (now U.S. Pat. No. 6,469,143, issued Oct. 22, 2002), which is a continuation of prior U.S. application Ser. No. 09/532,106, filed Mar. 21, 2000 (now U.S. Pat. No. 6,245,895, issued Jun. 12, 2001), which is a continuation of prior U.S. application Ser. No. 09/246,258, filed Feb. 8, 1999 (now U.S. Pat. No. 6,040,137, issued Mar. 21, 2000), which is a continuation of prior U.S. application Ser. No. 08/737,085, filed Dec. 27, 1996 (now U.S. Pat. No. 5,869,232, issued Feb. 9, 1999), which is a National Phase application under 35 U.S.C. §371 of PCT/SE95/00468 filed Apr. 27, 1995.

The present application is also a Continuation-In-Part of prior U.S. application Ser. No. 09/664,945, filed Sep. 19, 2000 now U.S. Pat. No. 6,660,842.

The present application is also a Continuation-In-Part of prior U.S. application Ser. No. 09/664,025, filed Sep. 19, 2000 now abandoned.

The present application is also a Continuation-In-Part of international application number PCT/IB01/02327, and claims the benefit of priority of international application number PCT/IB01/02327, having an international filing date of Sep. 19, 2001, designating the United States of America and published in English, which claims the benefit of priority of U.S. application Ser. No. 09/664,025, filed Sep. 19, 2000.

The present application is also a Continuation-In-Part of prior U.S. application Ser. No. 10/153,271, filed May 21, 2002 now abandoned, which is a divisional of prior U.S. application Ser. No. 09/556,605, filed Apr. 21, 2000 (now U.S. Pat. No. 6,417,324, issued Jul. 9, 2002).

The present application is also a Continuation-In-Part of prior U.S. application Ser. No. 09/839,447, filed Apr. 20, 2001 now abandoned, which is a continuation-in-part of prior U.S. application Ser. No. 09/556,605, filed Apr. 21, 2000 (now U.S. Pat. No. 6,417,324, issued Jul. 9, 2002).

The present application claims priority to all of the above-referenced prior applications and the disclosures of these prior applications are hereby expressly incorporated by reference in their entireties.

FIELD OF THE INVENTION

The present disclosure generally relates to compositions and methods for preventing and treating human diseases including cancer and those resulting from pathogens such as bacteria, yeast, parasites, fungus, viruses, and the like. More specifically, embodiments described herein concern the manufacture and use of specificity exchangers, which redirect existing antibodies in a subject to pathogens and cancer cells.

BACKGROUND OF THE INVENTION

Infection by pathogens, such as bacteria, yeast, parasites, fungus, and viruses, and the onset and spread of cancer present serious health concerns for all animals, including humans, farm livestock, and household pets. These health threats are exacerbated by the rise of strains that are resistant to vaccination and/or treatment. In the past, practitioners of pharmacology have relied on traditional methods of drug discovery to generate safe and efficacious compounds for the treatment of these diseases. Traditional drug discovery methods typically involve blindly testing potential drug candidate-molecules, often selected at random, in the hope that one might prove to be an effective treatment for some disease. With the advent of molecular biology, however, the focus of drug discovery has shifted to the identification of molecular targets associated with the etiological agent and the design of compounds that interact with these molecular targets.

One promising class of molecular targets are antigens found on the surface of bacteria, yeast, parasites, fungus, viruses, toxins and cancer cells. It has been shown that synthetic peptides corresponding to antibody regions (e.g., a CDR) can act as a mini antibody by binding to a particular antigen on a pathogen or cancer cell and neutralizing the pathogen or cancer cell in vitro. Although several antigen antagonists have promising therapeutic potential, there still remains a need for new compositions and methods to treat and prevent infection by pathogens and other disease.

Another promising class of molecular targets are the receptors found on the surface of bacteria, yeast, parasites, fungus, viruses, toxins and cancer cells, especially receptors that allow for attachment to a host cell or host protein (e.g., an extracellular matrix protein). Research in this area primarily focuses on the identification of the receptor and its ligand and the discovery of molecules that interrupt the interaction of the ligand with the receptor and, thereby, block adhesion to the host cell or protein. Although several receptor antagonists have promising therapeutic potential, there still remains a need for new compositions and methods to treat and prevent infection by pathogens and other diseases.

SUMMARY OF THE INVENTION

Embodiments described herein are directed to specificity exchangers comprising at least one specificity domain and at least one antigenic domain joined to said specificity domain, wherein said antigenic domain comprises a peptide or an epitope obtained from a pathogen or toxin. In some embodiments, the specificity exchanger is an antigen/antibody specificity exchanger that comprises a specificity domain having a sequence obtained from an antibody joined to an antigenic domain that comprises a peptide or an epitope obtained from a pathogen or toxin, preferably a viral antigen such as polio virus, TT virus, herpes virus, hepatitis virus, or human immunodeficiency virus (HIV). In other embodiments, the specificity exchanger is a ligand/receptor specificity exchanger that comprises a specificity domain having a ligand for a receptor joined to an antigenic domain that comprises a peptide or an epitope obtained from a pathogen or toxin, preferably a viral antigen such as polio virus, TT virus, herpes virus, hepatitis virus, or human immunodeficiency virus.

The length of the specificity domain of the specificity exchangers is desirably between at least 3–200 amino acids, preferably between at least 5–100 amino acids, more preferably between 8–50 amino acids, and still more preferably between 10–25 amino acids. The length of the antigenic domain of the specificity exchangers is desirably between at least 3–200 amino acids, preferably between at least 5–100 amino acids, more preferably between 8–50 amino acids, and still more preferably between 10–25 amino acids.

The specificity exchangers described herein comprise specificity domains that interact with antigens or receptors on pathogens, including, but not limited to, bacteria, yeast, parasites, fungus, and cancer cells. Some embodiments, for example, comprise a sequence obtained from an antibody that binds to a bacteria, hepatitis virus, or HIV. Other embodiments have a specificity domain that comprises a fragment of an extracellular matrix protein (e.g., between 3 and 14 amino acids, such as 3 to 5, 8, 9, 10, 12, or 14 consecutive amino acids of fibrinogen), a ligand for a receptor on a virus, or a ligand for a receptor on a cancer cell. In preferred embodiments, for example, the specificity domain comprises a ligand that is a fragment (e.g., between 3 and 20 amino acids, such as 3 to 5, 8, 9, 10, 12, 14, 17, and 20 consecutive amino acids) of an extracellular matrix protein selected from the group consisting of fibrinogen, collagen, vitronectin, laminin, plasminogen, thrombospondin, and fibronectin.

Several of the specificity exchangers described herein bind to a receptor found on a pathogen (vis a vis antigen/antibody interaction or ligand/receptor interaction). In some embodiments, the receptor is a bacterial adhesion receptor, for example, a bacterial adhesion receptor selected from the group consisting of extracellular fibrinogen binding protein (Efb), collagen binding protein, vitronectin binding protein, laminin binding protein, plasminogen binding protein, thrombospondin binding protein, clumping factor A (ClfA), clumping factor B (ClfB), fibronectin binding protein, coagulase, and extracellular adherence protein.

In some embodiments, the specificity exchangers comprise a specificity domain that comprises at least one of the following sequences: SEQ. ID. No. 1, SEQ. ID. No. 2, SEQ. ID. No. 3, SEQ. ID. No. 4, SEQ. ID. No. 5, SEQ. ID. No. 6, SEQ. ID. No. 7, SEQ. ID. No. 8, SEQ. ID. No. 9, SEQ. ID. No. 10, SEQ. ID. No. 11, SEQ. ID. No. 12, SEQ. ID. No. 13, SEQ. ID. No. 14, SEQ. ID. No. 15, SEQ. ID. No. 16, SEQ. ID. No. 17, SEQ. ID. No. 18, SEQ. ID. No. 19, SEQ. ID. No. 20, SEQ. ID. No. 21, SEQ. ID. No. 22, SEQ. ID. No. 23, SEQ. ID. No. 24, SEQ. ID. No. 25, SEQ. ID. No. 26, SEQ. ID. No. 27, SEQ. ID. No. 28, SEQ. ID. No. 29, SEQ. ID. No. 30, SEQ. ID. No. 31, SEQ. ID. No. 32, SEQ. ID. No. 33, SEQ. ID. No. 34, SEQ. ID. No. 35, SEQ. ID. No. 36, SEQ. ID. No. 37, SEQ. ID. No. 38, SEQ. ID. No. 39, SEQ. ID. No. 40, SEQ. ID. No. 41, SEQ. ID. No. 42, SEQ. ID. No. 43, SEQ. ID. No. 44, SEQ. ID. No. 45, SEQ. ID. No. 46, or SEQ. ID. No. 47.

In other embodiments, the specificity exchangers comprise an antigenic domain that comprises at least one of the following sequences: SEQ. ID. No. 48, SEQ. ID. No. 49, SEQ. ID. No. 50, SEQ. ID. No. 51, SEQ. ID. No. 52, SEQ. ID. No. 53, SEQ. ID. No. 54, SEQ. ID. No. 55, SEQ. ID. No. 56, SEQ. ID. No. 57, and SEQ. ID. No. 58, SEQ. ID. No. 59, SEQ. ID. No. 60, SEQ. ID. No. 61, SEQ. ID. No. 62, SEQ. ID. No. 63, SEQ. ID. No. 64, SEQ. ID. No. 65, SEQ. ID. No. 66, SEQ. ID. No. 67, SEQ. ID. No. 68, SEQ. ID. No. 69, SEQ. ID. No. 70, or SEQ. ID. No. 71.

More embodiments include specificity exchangers that comprise at least one of the following sequences: SEQ. ID. No. 72, SEQ. ID. No. 73, SEQ. ID. No. 74, SEQ. ID. No. 75, SEQ. ID. No. 76, SEQ. ID. No. 77, SEQ. ID. No. 78, SEQ. ID. No. 79, SEQ. ID. No. 80, SEQ. ID. No. 81, SEQ. ID. No. 82, SEQ. ID. No. 83, SEQ. ID. No. 84, SEQ. ID. No. 85, SEQ. ID. No. 86, SEQ. ID. No. 87, SEQ. ID. No. 88, SEQ. ID. No. 89, SEQ. ID. No. 90, SEQ. ID. No. 91, SEQ. ID. No. 92, SEQ. ID. No. 93, SEQ. ID. No. 94, SEQ. ID. No. 95, SEQ. ID. No. 96, SEQ. ID. No. 97, SEQ. ID. No. 98, SEQ. ID. No. 99, SEQ. ID. No. 100, SEQ. ID. No. 101, SEQ. ID. No. 102, SEQ. ID. No. 103, SEQ. ID. No. 104, SEQ. ID. No. 105, SEQ. ID. No. 106, SEQ. ID. No. 107, SEQ. ID. No. 108, SEQ. ID. No. 109, SEQ. ID. No. 110, SEQ. ID. No. 111, SEQ. ID. No. 112, SEQ. ID. No. 113, SEQ. ID. No. 114, SEQ. ID. No. 115, SEQ. ID. No. 118, SEQ. ID. No. 119, SEQ. ID. No. 120, SEQ. ID. No. 121, SEQ. ID. No. 122, SEQ. ID. No. 123, SEQ. ID. No. 124, SEQ. ID. No. 125, SEQ. ID. No. 126, SEQ. ID. No. 127, SEQ. ID. No. 128, SEQ. ID. No. 159, SEQ. ID. No. 160, SEQ. ID. No. 161, SEQ. ID. No. 162, SEQ. ID. No. 163, SEQ. ID. No. 164, SEQ. ID. No. 165, SEQ. ID. No. 166, SEQ. ID. No. 167, SEQ. ID. No. 168, SEQ. ID. No. 169, SEQ. ID. No. 170, SEQ. ID. No. 171, SEQ. ID. No. 172, SEQ. ID. No. 173, SEQ. ID. No. 174, SEQ. ID. No. 175, SEQ. ID. No. 176, SEQ. ID. No. 177, SEQ. ID. No. 178, SEQ. ID. No. 179, SEQ. ID. No. 180, SEQ. ID. No. 181, SEQ. ID. No. 182, SEQ. ID. No. 183, SEQ. ID. No. 184, SEQ. ID. No. 185, SEQ. ID. No. 186, SEQ. ID. No. 187, SEQ. ID. No. 188, SEQ. ID. No. 189, SEQ. ID. No. 190, SEQ. ID. No. 191, SEQ. ID. No. 192, SEQ. ID. No. 193, SEQ. ID. No. 194, SEQ. ID. No. 195, or SEQ. ID. No. 196.

Several embodiments also concern specificity exchangers that can be used to treat or prevent infection by a pathogen. One approach, for example, involves providing a therapeutically effective amount of a specificity exchanger to a subject, wherein said specificity exchanger comprises a specificity domain that interacts with a receptor or antigen on said pathogen, and an antigenic domain that comprises a peptide or an epitope obtained from a pathogen or toxin. Many of the specificity exchangers described herein can be used with these approaches. In some embodiments, the subject is monitored for a reduction of the pathogen after providing the specificity exchanger. In other approaches, the subject is identified as one in need of a molecule that redirects antibodies present in the subject to the pathogen prior to providing the specificity exchanger.

Several embodiments also concern specificity exchangers that can be used to treat or prevent bacterial infection. By one approach, a therapeutically effective amount of a specificity exchanger is provided to a subject, wherein said specificity exchanger comprises a specificity domain that interacts with a receptor or antigen on said bacteria, and an antigenic domain that comprises a peptide or an epitope obtained from a pathogen or toxin. Several specificity exchangers that interact with bacteria, for example, *Staphylococcus*, are described herein and any one of these can be used with these methods. In some approaches, the subject is monitored for a reduction of the bacteria after providing the specificity exchanger. In other approaches, the subject is identified as one in need of a molecule that redirects antibodies present in the subject to the bacteria prior to providing the specificity exchanger.

Still more embodiments concern specificity exchangers that can be used to treat or prevent viral infection. By one approach, a therapeutically effective amount of a specificity exchanger is provided to a subject, wherein said specificity exchanger comprises a specificity domain that interacts with a receptor or antigen on a virus, and an antigenic domain that comprises a peptide or an epitope obtained from a pathogen or toxin. Several specificity exchangers that interact with a virus, for example, a hepatitis virus, are described herein and any one of these can be used with this method. In some approaches, the subject is monitored for a reduction of the virus after providing the specificity exchanger. In other approaches, the subject is identified as one in need of a molecule that redirects antibodies present in the subject to the virus prior to providing the specificity exchanger.

Still more embodiments concern specificity exchangers that can be used to treat or prevent cancer. By one approach, a therapeutically effective amount of a specificity exchanger is provided to a subject, wherein said specificity exchanger comprises a specificity domain that interacts with a receptor or antigen on a cancer cell, and an antigenic domain that comprises a peptide or an epitope obtained from a pathogen or toxin. Several specificity exchangers that interact with a cancer cell, for example, a myeloma cell, are described herein and any one of these can be used with this method. In some approaches, the subject is monitored for a reduction of the pathogen after providing the specificity exchanger. In other approaches, the subject is identified as one in need of a molecule that redirects antibodies present in the subject to the pathogen prior to providing the specificity exchanger.

DETAILED DESCRIPTION OF THE PREFERRED EMBODIMENT

The following sections describe the manufacture, characterization, and use of specificity exchangers that bind pathogens and redirect antibodies that are present in a subject to the pathogen. Specificity exchangers are generally composed of two domains, a specificity domain and an antigenic domain. There are two general types of specificity exchangers differentiated by the nature of their specificity domains. The first type of specificity exchanger is an antigen/antibody specificity exchanger. Several antigen/antibody specificity exchangers are known in the art. See e.g., U.S. Pat. Nos. 5,869,232; 6,040,137; 6,245,895; 6,417,324; 6,469,143; and U.S. application Ser. Nos. 09/839,447 and 09/839,666; and International App. Nos. PCT/SE95/00468 and PCT/IB01/00844, all of which are hereby expressly incorporated by reference in their entireties.

Antigen/antibody specificity exchangers comprise an amino acid sequence of an antibody that specifically binds to an antigen (i.e., the specificity domain) joined to an amino acid sequence to which an antibody binds (i.e., the antigenic domain). Some specificity domains of antigen/antibody specificity exchangers comprise an amino acid sequence of a complementarity determining region (CDR), are at least 5 and less than 35 amino acids in length, are specific for bacterial antigens, HIV-1 antigens, or are specific for hepatitis viral antigens. Some antigenic domains of antigen/antibody specificity exchangers comprise a peptide having an antibody-binding region (epitope) of viral, bacterial, or fungal origin, are at least 5 and less than 35 amino acids in length, or contain antigenic peptides obtained from the polio virus, measles virus, hepatitis B virus, hepatitis C virus, or HIV-1.

The second type of specificity exchanger, the ligand/receptor specificity exchanger, is also composed of a specificity domain and an antigenic domain, however, the specificity domain of the ligand/receptor specificity exchanger comprises a ligand for a receptor that is present on a pathogen, as opposed to a sequence of an antibody that binds to an antigen. That is, a ligand/receptor specificity exchanger differs from an antibody/antigen specificity exchanger in that the ligand/receptor specificity exchanger does not contain a sequence of an antibody that binds an antigen but, instead, adheres to the pathogen through a ligand interaction with a receptor that is present on the pathogen. Several ligand/receptor specificity exchangers are also known in the art. See e.g., U.S. application Ser. Nos. 09/664,945 and 09/664,025; and International App. No. PCT/IB01/02327, all of which are hereby expressly incorporated by reference in their entireties.

Some specificity domains of ligand/receptor specificity exchangers comprise an amino acid sequence that is a ligand for a bacterial adhesion receptor (e.g., extracellular fibrinogen binding protein or clumping factor A or B), are at least 3 and less than 27 amino acids in length, or are specific for bacteria, viruses, or cancer cells. Some antigenic domains of ligand/receptor specificity exchangers comprise a peptide having an antibody-binding region (epitope) of a pathogen or toxin, are at least 5 and less than 35 amino acids in length, or contain antigenic peptides obtained from polio virus, TT virus, hepatitis B virus, and herpes simplex virus.

As used herein, the term "specificity exchanger" refers to both ligand/receptor specificity exchangers and antigen/antibody specificity exchangers. If a specific type of specificity exchanger is being described, either the term "ligand/receptor specificity exchanger" or "antigen/antibody specificity exchanger" is used. While there are two main types of specificity exchangers, certain embodiments include specificity exchangers with one or more ligands and one or more amino acid sequences of an antibody that specifically binds to an antigen. In some embodiments, the specificity exchangers described herein can have 1, 2, 3, 4, 5, 6, 7, 8, 9 or 10 ligands, which are the same or different molecules, in their specificity domain. Likewise, specificity exchangers can have a specificity domain that includes 1, 2, 3, 4, 5, 6, 7, 8, 9 or 10 amino acid sequences of an antibody that specifically bind to an antigen, which are the same or different molecules. The following section describes some general features of specificity exchangers.

Specificity Exchangers

Specificity exchangers have a variety of chemical structures but are typically characterized as having at least one specificity domain that interacts with a pathogen (vis a vis antigen/antibody interaction or ligand/receptor interaction), cancer cell, or toxin (e.g. a receptor or an antigen) and at least one antigenic domain that interacts with an antibody. Generally, the specificity exchangers described herein (i.e., antibody/antigen specificity exchangers and ligand/receptor specificity exchangers) comprise a specificity domain, which is at least 3 and less than or equal to 200 amino acids in length, joined to an antigenic domain (e.g., a peptide backbone), which is at least 3 and less than or equal to 200 amino acids in length, and the antigenic domain in conjunction with the specificity domain or by itself, reacts with high titer antibodies that are present in a subject (e.g., a human).

In some embodiments, for example, the specificity exchangers comprise a specificity domain that is any length between 3 and 200 amino acids. That is, at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, or 200 amino acids in length and said specificity domain is joined to an antigenic domain, which is any length between 3 and 200 amino acids; that is at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, or 200 amino acids in length.

Preferred specificity exchangers are peptides but some embodiments comprise derivatized or modified peptides, a peptidomimetic structure or chemicals. For example, a typical peptide-based specificity exchanger can be modified to have substituents not normally found on a peptide or to have substituents that are normally found on a peptide but are incorporated at regions that are not normal. In this vein, a peptide-based specificity exchanger can be acetylated, acylated, or aminated and the substituents that can be included on the peptide so as to modify it include, but are not limited to, H, alkyl, aryl, alkenyl, alkynl, aromatic, ether, ester, unsubstituted or substituted amine, amide, halogen or unsubstituted or substituted sulfonyl or a 5 or 6 member aliphatic or aromatic ring. Thus, the term "specificity exchanger" is a broad one that encompasses modified or unmodified peptide structures, as well as peptidomimetics and chemical structures.

There are many ways to make a peptidomimetic that resembles a peptide-based specificity exchanger. The naturally occurring amino acids employed in the biological production of peptides all have the L-configuration. Synthetic peptides can be prepared employing conventional synthetic methods, utilizing L-amino acids, D-amino acids, or various combinations of amino acids of the two different configurations. Synthetic compounds that mimic the conformation and desirable features of a peptide but that avoid the undesirable features, e.g., flexibility (loss of conformation) and bond breakdown are known as a "peptidomimetics". (See, e.g., Spatola, A. F. Chemistry and Biochemistry of Amino Acids. Peptides, and Proteins (Weistein, B, Ed.), Vol. 7, pp. 267–357, Marcel Dekker, New York (1983), which describes the use of the methylenethio bioisostere [$CH_2$ S] as an amide replacement in enkephalin analogues; and Szelke et al., In peptides: Structure and Function, Proceedings of the Eighth American Peptide Symposium, (Hruby and Rich, Eds.); pp. 579–582, Pierce Chemical Co., Rockford, Ill. (1983), which describes renin inhibitors having both the methyleneamino [$CH_2$ NH] and hydroxyethylene [$CHOHCH_2$] bioisosteres at the Leu-Val amide bond in the 6–13 octapeptide derived from angiotensinogen, all of which are expressly incorporated by reference in their entireties).

In general, the design and synthesis of a peptidomimetic that resembles a specificity exchanger involves starting with the sequence of a specificity exchanger and conformation data (e.g., geometry data, such as bond lengths and angles) of a desired specificity exchanger (e.g., the most probable simulated peptide), and using such data to determine the geometries that should be designed into the peptidomimetic. Numerous methods and techniques are known in the art for performing this step, any of which could be used. (See, e.g., Farmer, P. S., *Drug Design*, (Ariens, E. J. ed.), Vol. 10, pp. 119–143 (Academic Press, New York, London, Toronto, Sydney and San Francisco) (1980); Farmer, et al., in *TIPS*, 9/82, pp. 362–365; Verber et al., in *TINS*, 9/85, pp. 392–396; Kaltenbronn et al., in *J. Med. Chem*. 33: 838–845 (1990); and Spatola, A. F., in *Chemistry and Biochemistry of Amino Acids. Peptides, and Proteins*, Vol. 7, pp. 267–357, Chapter 5, "Peptide Backbone Modifications: A Structure-Activity Analysis of Peptides Containing Amide Bond Surrogates. Conformational Constraints, and Relations" (B. Weisten, ed.; Marcell Dekker: New York, pub.) (1983); Kemp, D. S., "Peptidomimetics and the Template Approach to Nucleation of β-sheets and α-helices in Peptides," Tibech, Vol. 8, pp. 249–255 (1990), all of which are expressly incorporated by reference in their entireties). Additional teachings can be found in U.S. Pat. Nos. 5,288,707; 5,552,534; 5,811,515; 5,817,626; 5,817,879; 5,821,231; and 5,874,529, all of which are expressly incorporated by reference in their entireties. Once the peptidomimetic is designed, it can be made using conventional techniques in peptide chemistry and/or organic chemistry.

Some embodiments include a plurality of specificity domains and/or a plurality of antigenic domains. One type of specificity exchanger that has a plurality of specificity domains and/or antigenic domains is referred to as a "multimerized specificity exchanger" because it has multiple specificity domains and/or antigenic domains that appear (e.g., are fused) in tandem on the same molecule. For example, a multimerized specificity domain can have two or more ligands that interact with one type of receptor, two or more ligands that interact with different types of receptors on the pathogen, two or more ligands that interact with different types of receptors on different pathogens, two or more antibody sequences that interact with one type of antigen on a pathogen, two or more antibody sequences that interact with different types of antigens on a pathogen, or two or more antibody sequences that interact with different types of antigens on different pathogens.

Similarly, a multimerized antigenic domain can be constructed to have multimers of the same epitope of a pathogen or different epitopes of a pathogen, which can also be multimerized. That is, some multimerized antigenic domains are multivalent because the same epitope is repeated. In contrast, some multimerized antigenic domains have more than one epitope present on the same molecule in tandem but the epitopes are different. In this respect, these antigenic domains are multimerized but not multivalent. Further, some multimerized antigenic domains are constructed to have different epitopes but the different epitopes are themselves multivalent because each type of epitope is repeated.

Some specificity exchangers or specificity domains or antigenic domains are disposed on or comprise a support. A "support" can be a carrier, a protein, a resin, a cell membrane, or any macromolecular structure used to join or immobilize specificity domains, antigenic domains, or the specificity exchangers themselves. For example, the antigenic domain can be thought of as a support (e.g., a backbone) onto which one or more specificity domains are joined. Further, a multimeric specificity exchanger can be made by joining a plurality of specificity domains to support that may be an antigenic domain in itself or may have a plurality of antigenic domains joined. Similarly, a specificity domain can be joined to a support onto which one or more antigenic domains are joined. Thus, a support can be used to link one or more specificity domains to one or more antigenic domains or the support can be an antigenic domain in itself.

Solid supports include, but are not limited to, the walls of wells of a reaction tray, test tubes, polystyrene beads, magnetic beads, nitrocellulose strips, membranes, microparticles such as latex particles, animal cells, Duracyte®, artificial cells, and others. A specificity exchanger or parts thereof can also be joined to inorganic supports, such as silicon oxide material (e.g. silica gel, zeolite, diatomaceous earth or aminated glass) by, for example, a covalent linkage through a hydroxy, carboxy, or amino group and a reactive group on the support.

In some embodiments, the macromolecular support has a hydrophobic surface that interacts with a portion of the specificity exchanger, by a hydrophobic non-covalent interaction. In some cases, the hydrophobic surface of the support is a polymer such as plastic or any other polymer in which hydrophobic groups have been linked such as polystyrene, polyethylene or polyvinyl. Additionally, a specificity exchanger, specificity domain, or antigenic domain can be covalently bound to supports including proteins and oligo/polysaccharides (e.g. cellulose, starch, glycogen, chitosane or aminated sepharose). In some embodiments, a reactive group on the molecule, such as a hydroxy or an amino group, is used to join to a reactive group on the carrier so as to create the covalent bond. Additional specificity exchangers comprise a support that has other reactive groups that are chemically activated so as to attach the specificity exchanger or parts thereof. For example, cyanogen bromide activated matrices, epoxy activated matrices, thio and thiopropyl gels, nitrophenyl chloroformate and N-hydroxy succinimide chlorformate linkages, or oxirane acrylic supports can be used. (Sigma). Furthermore, in some embodiments, a liposome or lipid bilayer (natural or synthetic) is contemplated as a support and a specificity exchanger, specificity domain, or antigenic domain can be attached to the membrane surface or are incorporated into the membrane by techniques in liposome engineering. By one approach, liposome multimeric supports comprise a specificity exchanger or parts thereof that is exposed on the surface.

Some specificity exchangers also comprise other elements in addition to the specificity domain and antigenic domain such as sequences that facilitate purification (e.g., polyhistidine tail), linkers that provide greater flexibility and reduce steric hindrance, and sequences that either provide greater stability to the specificity exchanger (e.g., resistance to protease degradation) or promote degradation (e.g., protease recognition sites). For example, the specificity exchangers can comprise cleavable signal sequences that promote cytoplasmic export of the peptide and/or cleavable sequence tags that facilitate purification on antibody columns, glutathione columns, and metal columns.

Specificity exchangers can also comprise elements that promote flexibility of the molecule, reduce steric hindrance, or allow the specificity exchanger to be attached to a support or other molecule. These elements are collectively referred to as "linkers". One type of linker that can be incorporated with a specificity exchanger, for example, is avidin or streptavidin (or their ligand—biotin). Through a biotin-avidin/streptavidin linkage, multiple specificity exchangers can be joined together (e.g., through a support, such as a resin, or directly) or individual specificity domains and antigenic domains can be joined. Another example of a linker that can be included in a specificity exchanger is referred to as a "λ linker" because it has a sequence that is found on λ phage. Preferred λ sequences are those that correspond to the flexible arms of the phage. These sequences can be included in a specificity exchanger (e.g., between the specificity domain and the antigenic domain or between multimers of the specificity and/or antigenic domains) so as to provide greater flexibility and reduce steric hindrance. Additionally, a plurality of alanine residues or other peptide sequences can be used as linkers.

Specificity exchangers can also include sequences that either confer resistance to protease degradation or promote protease degradation. By incorporating multiple cysteines in a specificity exchanger, for example, greater resistance to protease degradation can be obtained. These embodiments of the ligand/receptor specificity exchanger are expected to remain in the body for extended periods, which may be beneficial for some therapeutic applications. In contrast, specificity exchangers can also include sequences that promote rapid degradation so as to promote rapid clearance from the body. Many sequences that serve as recognition sites for serine, cysteine, and aspartic proteases are known and can be included in a specificity exchanger. The section below describes the specificity domains of antigen/antibody specificity exchangers in greater detail.

Specificity Domains of Antigen/Antibody Specificity Exchangers

The specificity domain of antigen/antibody specificity exchangers can include the amino-acid sequence of any antibody which specifically binds to a certain antigen, such as a hapten, for example. Preferred specificity domains of antigen/antibody specificity exchangers comprise an amino acid sequence of a complementarity determining region (CDR) or a framework region of a certain antibody. The CDRs of antibodies are responsible for the specificity of the antibody. X-ray crystallography has shown that the three CDRs of the variable (V) region of the heavy chain and the three CDRs of the V region of the light chain may all have contact with the epitope in an antigen-antibody complex.

In certain embodiments, single peptides corresponding to the CDRs of mAbs to various antigens and that are capable of mimicking the recognition capabilities of the respective mAb can be included in the specificity domain of the antigen/antibody specificity exchangers. Specifically a peptide corresponding to CDRH3 of a mAb specific for the V3 region of human immuno deficiency virus-1 gp160 can be included in the specificity domain. This peptide was shown to have neutralizing capacity when assayed in vitro. The CDRH3 can be derived from mAb F58, and Ab C1–5, and the like. Like CDRH3, the CDRH1 and/or CDRH2 domain of Ab $C_{1-5}$ can also be used in the specificity domains described herein. In other embodiments the specificity domain can include a peptide corresponding to CDRH2 of a mAb to hepatitis B virus core antigen (HBcAg). CDRH2 has demonstrated an ability to capture HBcAg. Several other peptides, derived from antibodies that bind HBcAg or hepatitis B virus e antigen (HBeAg) have been identified. See U.S. Pat. No. 6,417,324, issued Jul. 9, 2002; and U.S. patent application Ser. No. 09/839,447, filed Apr. 20, 2001 and U.S. patent application Ser. No. 10/153,271, filed May 21, 2002, all of which are hereby incorporated by reference in their entireties. These peptides (specificity domains) can be incorporated into antigen/antibody specificity exchangers so as to redirect antibodies present in a subject to hepatitis B virus.

TABLE I provides a non-exclusive list of specificity domains that can be used in the antigen/antibody specificity exchangers described herein. The section following TABLE I describes the specificity domains of ligand/receptor specificity exchangers in greater detail.

TABLE I

| SPECIFICITY DOMAINS FOR ANTIGEN/ANTIBODY SPECIFICITY EXCHANGERS | |
|---|---|
| CDLIYYDYEEDYYF: | SEQ ID NO: 43 |
| CDLIYYDYEEDYY: | SEQ ID NO: 44 |
| TYAMN: | SEQ ID NO: 45 |
| RVRSKSFNYATYYADSVKG: | SEQ ID NO: 46 |
| PAQGIYFDYGGFAY: | SEQ ID NO: 47 |

Specificity Domains for Ligand/Receptor Spceficity Exchangers

The diversity of ligand/receptor specificity exchangers is also equally vast because many different ligands that bind many different receptors on many different pathogens can be incorporated into a ligand/receptor specificity exchanger. The term "pathogen" generally refers to any etiological agent of disease in an animal including, but not limited to, bacteria, parasites, fungus, mold, viruses, and cancer cells. Similarly, the term "receptor" is used in a general sense to refer to a molecule (usually a peptide other than a sequence found in an antibody, but can be a carbohydrate, lipid, or nucleic acid) that interacts with a "ligand" (usually a peptide other than a sequence found in an antibody, or a carbohydrate, lipid, nucleic acid or combination thereof). The receptors contemplated do not have to undergo signal transduction and can be involved in a number of molecular interactions including, but not limited to, adhesion (e.g., integrins) and molecular signaling (e.g., growth factor receptors).

In certain embodiments, desired specificity domains include a ligand that has a peptide sequence that is present in an extracellular matrix protein (e.g., fibrinogen, collagen, vitronectin, laminin, plasminogen, thrombospondin, and fibronectin) and some specificity domains comprise a ligand that interacts with a bacterial adhesion receptor (e.g., extracellular fibrinogen binding protein (Efb), collagen binding protein, vitronectin binding protein, laminin binding protein, plasminogen binding protein, thrombospondin binding protein, clumping factor A (ClfA), clumping factor B (ClfB), fibronectin binding protein, coagulase, and extracellular adherence protein).

Investigators have mapped the regions of extracellular matrix proteins that interact with several receptors. (See e.g., McDevvit et al., *Eur. J. Biochem.*, 247:416–424 (1997); Flock, *Molecular Med. Today*, 5:532 (1999); and Pei et al., *Infect. and Immun.* 67:4525 (1999), all of which are herein expressly incorporated by reference in their entirety). Some receptors bind to the same region of the extracellular matrix protein, some have overlapping binding domains, and some bind to different regions altogether. Preferably, the ligands that make up the specificity domain have an amino acid sequence that has been identified as being involved in adhesion to an extracellular matrix protein. It should be understood, however, that random fragments of known ligands for any receptor on a pathogen can be used to generate ligand/receptor specificity exchangers and these candidate ligand/receptor specificity exchangers can be screened in the characterization assays described infra to identify the molecules that interact with the receptors on the pathogen.

Some specificity domains have a ligand that interacts with a bacterial adhesion receptor including, but not limited to, extracellular fibrinogen binding protein (Efb), collagen binding protein, vitronectin binding protein, laminin binding protein, plasminogen binding protein, thrombospondin binding protein, clumping factor A (ClfA), clumping factor B (ClfB), fibronectin binding protein, coagulase, and extracellular adherence protein. Ligands that have an amino acid sequence corresponding to the C-terminal portion of the gamma-chain of fibrinogen have been shown to competitively inhibit binding of fibrinogen to ClfA, a *Staphylococcus aureus* adhesion receptor. (McDevvit et al., *Eur. J. Biochem.*, 247:416–424 (1997)). Further, *Staphylococcus* organisms produce many more adhesion receptors such as Efb, which binds to the alpha chain fibrinogen, ClfB, which interacts with both the α and β chain of fibrinogen, and Fbe, which binds to the β chain of fibrinogen. (Pei et al., *Infect. and Immun.* 67:4525 (1999)). Accordingly, preferred specificity domains comprise between 3 and 30 amino acids, that is, at least 3, 4, 5, 6, 7, 8, 9, 10, 11, 12, 13, 14, 15, 16, 17, 18, 19, 20, 21, 22, 23, 24, 25, 26, 27, 28, 29, or 30 consecutive amino acids of a sequence present in a molecule (e.g., fibrinogen) that can bind to a bacterial adhesion receptor.

Specificity domains can also comprise a ligand that interacts with a viral receptor. Several viral receptors and corresponding ligands are known and these ligands or fragments thereof can be incorporated into a ligand/receptor specificity exchanger. For example, Tong et al., has identified an Hepadnavirus receptor, a 170 kd cell surface glycoprotein that interacts with the pre-S domain of the duck hepatitis B virus envelope protein (U.S. Pat. No. 5,929,220) and Maddon et al., has determined that the T cell surface protein CD4 (or the soluble form termed T4) interacts with gp120 of HIV (U.S. Pat. No. 6,093,539); both references are herein expressly incorporated by reference in their entireties. Thus, specificity domains that interact with a viral receptor can comprise regions of the pre-S domain of the duck hepatitis B virus envelope protein (e.g., amino acid residues 80–102 or 80–104) or regions of the T cell surface protein CD4 (or the soluble form termed T4) that interacts with gp120 of HIV (e.g., the extracellular domain of CD4/T4 or fragments thereof). Many more ligands for viral receptors exist and these molecules or fragments thereof can be used as a specificity domain.

Specificity domains can also comprise a ligand that interacts with a receptor present on a cancer cell. The proto-oncogene HER-2/neu (C-erbB2) encodes a surface growth factor receptor of the tyrosine kinase family, p185HER2. Twenty to thirty percent of breast cancer patients over express the gene encoding HER-2/neu (C-erbB2), via gene amplification. Thus, ligand/receptor specificity exchangers comprising a specificity domain that encodes a ligand for HER-2/neu (C-erbB2) are desirable embodiments.

Many types of cancer cells also over express or differentially express integrin receptors. Many preferred embodiments comprise a specificity domain that interacts with an integrin receptor. Although integrins predominantly interact with extracellular matrix proteins, it is known that these receptors interact with other ligands such as invasins, RGD-containing peptides (i.e., Arginine-Glycine-Aspartate), and chemicals. (See e.g., U.S. Pat. Nos. 6,090,944 and 6,090,388; and Brett et al., *Eur J Immunol*, 23:1608 (1993), all of which are hereby expressly incorporated by reference in their entireties). Ligands for integrin receptors include, but are not limited to, molecules that interact with a vitronectin receptor, a laminin receptor, a fibronectin receptor, a collagen receptor, a fibrinogen receptor, an $\alpha_4\beta_1$ receptor, an $\alpha_6\beta_1$ receptor, an $\alpha_3\beta_1$ receptor, an $\alpha_5\beta_1$ receptor, and an $\alpha_v\beta_3$receptor. Preferably, the specificity domain of an antigen/antibody specificity exchanger is between 5–35 amino acids in length. TABLE II lists several preferred specificity domains for ligand/receptor specificity exchangers. The section that follows TABLE II describes the antigenic domains of specificity exchangers in greater detail.

TABLE II

| SPECIFICITY DOMAINS FOR LIGAND/RECEPTOR SPECIFICITY EXCHANGERS | |
|---|---|
| YGEGQQHHLGGAKQAGDV | (SEQ. ID. No. 1) |
| MSWSLHPRNLILYFYALLFL | (SEQ. ID. No. 2) |
| ILYFYALLFLSTCVAYVAT | (SEQ. ID. No. 3) |
| SSTCVAYVATRDNCCILDER | (SEQ. ID. No. 4) |
| RDNCCILDERFGSYCPTTCG | (SEQ. ID. No. 5) |
| FGSYCPTTCGIADFLSTYQT | (SEQ. ID. No. 6) |

TABLE II-continued

SPECIFICITY DOMAINS FOR LIGAND/RECEPTOR SPECIFICITY EXCHANGERS

| Sequence | |
|---|---|
| IADFLSTYQTKVDKDLQSLE | (SEQ. ID. No. 7) |
| KVDKDLQSLEDILHQVENKT | (SEQ. ID. No. 8) |
| DILHQVENKTSEVKQLIKAI | (SEQ. ID. No. 9) |
| SEVKQLIKAIQLTYNPDESS | (SEQ. ID. No. 10) |
| QLTYNPDESSKPNMIDAATL | (SEQ. ID. No. 11) |
| KPNMIDAATLKSRIMLEEIM | (SEQ. ID. No. 12) |
| KSRIMLEEIMKYEASILTHD | (SEQ. ID. No. 13) |
| KYEASILTHDSSIRYLQEIY | (SEQ. ID. No. 14) |
| SSIRYLQEIYNSNNQKIVNL | (SEQ. ID. No. 15) |
| NSNNQKIVNLKEKVAQLEAQ | (SEQ. ID. No. 16) |
| CQEPCKDTVQIHDITGKDCQ | (SEQ. ID. No. 17) |
| IHDITGKDCQDIANKGAKQS | (SEQ. ID. No. 18) |
| DIANKGAKQSGLYFIKPLKA | (SEQ. ID. No. 19) |
| GLYFIKPLKANQQFLVYCEI | (SEQ. ID. No. 20) |
| NQQFLVYCEIDGSGNGWTVF | (SEQ. ID. No. 21) |
| DGSGNGWTVFQKRLDGSVDF | (SEQ. ID. No. 22) |
| QKRLDGSVDFKKNWIQYKEG | (SEQ. ID. No. 23) |
| KKNWIQYKEGFGHLSPTGTT | (SEQ. ID. No. 24) |
| FGHLSPTGTTEFWLGNEKIH | (SEQ. ID. No. 25) |
| EFWLGNEKIHLISTQSAIPY | (SEQ. ID. No. 26) |
| LISTQSAIPYALRVELEDWN | (SEQ. ID. No. 27) |
| ALRVELEDWNGRTSTADYAM | (SEQ. ID. No. 28) |
| GRTSTADYAMFKVGPEADKY | (SEQ. ID. No. 29) |
| FKVGPEADKYRLTYAYFAGG | (SEQ. ID. No. 30) |
| RLTYAYFAGGDAGDAFDGFD | (SEQ. ID. No. 31) |
| DAGDAFDGFDFGDDPSDKFF | (SEQ. ID. No. 32) |
| FGDDPSDKFFTSHNGMQFST | (SEQ. ID. No. 33) |
| TSHNGMQFSTWDNDNDKFEG | (SEQ. ID. No. 34) |
| WDNDNDKFEGNCAEQDGSGW | (SEQ. ID. No. 35) |
| NCAEQDGSGWWMNKCHAGHL | (SEQ. ID. No. 36) |
| WMNKCHAGHLNGVYYQGGTY | (SEQ. ID. No. 37) |
| NGVYYQGGTYSKASTPNGYD | (SEQ. ID. No. 38) |
| SKASTPNGYDNGIIWATWKT | (SEQ. ID. No. 39) |
| NGIIWATWKTRWYSMKKTTM | (SEQ. ID. No. 40) |
| RWYSMKKTTMKIIPFNRLTI | (SEQ. ID. No. 41) |
| KIIPFNRLTIGEGQQHHLGGAKQAGDV | (SEQ. ID. No. 42) |

Antigenic Domains

The diversity of antigenic domains that can be used in the ligand/receptor specificity exchangers and antibody/antigen specificity exchangers is quite large because a pathogen or toxin can present many different epitopes. Desirably, the antigenic domains used with the specificity exchangers are peptides obtained from surface proteins or exposed proteins from bacteria, fungi, plants, molds, viruses, cancer cells, and toxins. It is also desired that the antigenic domains comprise a peptide sequence that is rapidly recognized as non-self by existing antibodies in a subject, preferably by virtue of naturally acquired immunity or vaccination. For example, many people are immunized against childhood diseases including, but not limited to, small pox, measles, mumps, rubella, and polio. Thus, antibodies to epitopes on these pathogens can be produced by an immunized person. Desirable antigenic domains have a peptide that contains one or more epitopes that is recognized by antibodies in the subject that are present in the subject to respond to pathogens such as small pox, measles, mumps, rubella, herpes, hepatitis, and polio.

Some embodiments, however, have antigenic domains that interact with an antibody that has been administered to the subject. For example, an antibody that interacts with an antigenic domain on a specificity exchanger can be co-administered with the specificity exchanger. Further, an antibody that interacts with a specificity exchanger may not normally exist in a subject but the subject has acquired the antibody by introduction of a biologic material or antigen (e.g., serum, blood, or tissue) so as to generate a high titer of antibodies in the subject. For example, subjects that undergo blood transfusion acquire numerous antibodies, some of which can interact with an antigenic domain of a specificity exchanger. Some preferred antigenic domains for use in a specificity exchanger also comprise viral epitopes or peptides obtained from pathogens such as the herpes simplex virus, hepatitis B virus, TT virus, and the poliovirus.

Preferably, the antigenic domains comprise an epitope or peptide obtained from a pathogen or toxin that is recognized by a "high-titer antibody." The term "high-titer antibody" as used herein, refers to an antibody that has high affinity for an antigen (e.g., an epitope on an antigenic domain). For example, in a solid-phase enzyme linked immunosorbent assay (ELISA), a high titer antibody corresponds to an antibody present in a serum sample that remains positive in the assay after a dilution of the serum to approximately the range of 1:100–1:1000 in an appropriate dilution buffer. Other dilution ranges include 1:200–1:1000, 1:200–1:900, 1:300–1:900, 1:300–1:800, 1:400–1:800, 1:400–1:700, 1:400–1:600, and the like. In certain embodiments, the ratio between the serum and dilution buffer is approximately: 1:100, 1:150, 1:200, 1:250, 1:300, 1:350, 1:400, 1:450, 1:500, 1:550, 1:600, 1:650, 1:700, 1:750, 1:800, 1:850, 1:900, 1:950, 1:1000. Approaches to determine whether the epitope or peptide obtained from a pathogen or toxin is recognizable by a high titer antibody are also provided infra in the Examples.

Epitopes or peptides of a pathogen that can be included in an antigenic domain of a specificity exchanger include the epitopes or peptide sequences disclosed in Swedish Pat No. 9901601-6; U.S. Pat. No. 5,869,232; Mol. Immunol. 28: 719–726 (1991); and J. Med. Virol. 33:248–252 (1991); all of which are herein expressly incorporated by reference in their entireties. Preferred antigenic domains, have an epitope or peptide obtained form herpes simplex virus gG2 protein, hepatitis B virus s antigen (HBsAg), hepatitis B virus e antigen (HBeAg), hepatitis B virus c antigen (HBcAg), TT virus, and the poliovirus or combination thereof or comprise a sequence selected from the group consisting of SEQ. ID. Nos. 48–71. TABLE III provides the amino acid sequence of several preferred antigenic domains that can be used with the specificity exchangers described herein. The section that follows TABLE III describes several approaches to make specificity exchangers.

TABLE III

| ANTIGENIC DOMAINS | |
|---|---|
| GLYSSIWLSPGRSYFET | (SEQ. ID. No. 48) |
| YTDIKYNPFTDRGEGNM | (SEQ. ID. No. 49) |
| DQNIHMNARLLIRSPFT | (SEQ. ID. No. 50) |
| LIRSPFTDPQLLVHTDP | (SEQ. ID. No. 51) |
| QKESLLFPPVKLLRRVP | (SEQ. ID. No. 52) |
| PALTAVETGAT | (SEQ. ID. No. 53) |
| STLVPETT | (SEQ. ID. No. 54) |
| TPPAYRPPNAPIL | (SEQ. ID. No. 55) |
| EIPALTAVE | (SEQ. ID. No. 56) |
| LEDPASRDLV | (SEQ. ID. No. 57) |
| HRGGPEEF | (SEQ. ID. No. 58) |
| HRGGPEE | (SEQ. ID. No. 59) |
| VLICGENTVSRNYATHS | (SEQ. ID. No. 60) |
| KINTMPPFLDTELTAPS | (SEQ. ID. No. 61) |
| PDEKSQREILLNKIASY | (SEQ. ID. No. 62) |
| TATTTTYAYPGTNRPPV | (SEQ. ID. No. 63) |
| STPLPETT | (SEQ. ID. No. 64) |
| PPNAPILS | (SEQ. ID. No. 65) |
| RPPNAPILST | (SEQ. ID. No. 66) |
| KEIPALTAVETG | (SEQ. ID. No. 67) |
| PAHSKEIPALTA | (SEQ. ID. No. 68) |
| WGCSGKLICT | (SEQ. ID. No. 69) |
| CTTAVPWNAS | (SEQ. ID. No. 70) |
| QRKTKRNTNRR | (SEQ. ID. No. 71) |

Methods of Making Specificity Exchangers

Many different specificity exchangers can be made using conventional techniques in recombinant engineering and/or peptide chemistry. In some embodiments, the specificity domains and antigenic domains of the specificity exchangers are made separately and are subsequently joined together (e.g., through linkers or by association with a common carrier molecule) and in other embodiments, the specificity domain and antigenic domain are made as part of the same molecule. For example, any of the specificity domains listed in TABLES I and II can be joined to any of the antigenic domains of TABLE III. Although the specificity and antigenic domains can be made separately and joined together through a linker or carrier molecule (e.g., a complex comprising a biotinylated specificity domain, streptavidin, and a biotinylated antigenic domain), it is preferred that the specificity exchangers are made as fusion proteins. Thus, preferred embodiments include fusion proteins comprising any of the specificity domains listed in TABLES I and II can be joined to any of the antigenic domains of TABLE III.

Specificity exchangers can be generated in accordance with conventional methods of protein engineering, protein chemistry, organic chemistry, and molecular biology. Additionally, some commercial enterprises manufacture made-to-order peptides and a specificity exchanger can be obtained by providing such a company with the sequence of a desired specificity exchanger and employing their service to manufacture the agent according to particular specifications (e.g., Bachem AG, Switzerland). Preferably, the specificity exchangers are prepared by chemical synthesis methods (such as solid phase peptide synthesis) using techniques known in the art, such as those set forth by Merrifield et al., *J. Am. Chem. Soc.* 85:2149 (1964), Houghten et al., *Proc. Natl. Acad. Sci. USA*, 82:51:32 (1985), Stewart and Young (*Solid phase peptide synthesis*, Pierce Chem Co., Rockford, Ill. (1984), and Creighton, 1983*, Proteins: Structures and Molecular Principles*, W. H. Freeman & Co., N.Y.; all references are herein expressly incorporated by reference in their entireties.

By another approach, solid phase peptide synthesis is performed using a peptide synthesizer, such as an Applied Biosystems 430A peptide synthesizer (Applied Biosystems, Foster City, Calif.). Each synthesis uses a p-methylbenzylhydrylamine solid phase support resin (Peptide International, Louisville, Ky.) yielding a carboxyl terminal amide when the peptides are cleaved off from the solid support by acid hydrolysis. Prior to use, the carboxyl terminal amide can be removed and the specificity exchangers can be purified by high performance liquid chromatography (e.g., reverse phase high performance liquid chromatography (RP-HPLC) using a PepS-15 C18 column (Pharmacia, Uppsala, Sweden)) and sequenced on an Applied Biosystems 473A peptide sequencer. An alternative synthetic approach uses an automated peptide synthesizer (Syro, Multisyntech, Tubingen, Germany) and 9-fluorenylmethoxycarbonyl (fmoc) protected amino acids (Milligen, Bedford, Mass.).

In still other embodiments, the specificity exchangers can be synthesized with a Milligen 9050 peptide synthesizer using 9-fluorenylmethoxy-carbonyl-protected amino acid esters. Synthesized specificity exchangers can be analysed and/or purified by reverse phase HPLC using a Pep-S 5 m column (Pharmacia-LKB, Uppsala, Sweden), run with a gradient from 10% to 60% $CH3CN$ against water containing 0.1% trifluoro-acetic acid.

While the specificity exchangers can be chemically synthesized, it can be more efficient to produce these polypeptides by recombinant DNA technology using techniques well known in the art. Such methods can be used to construct expression vectors containing nucleotide sequences encoding a specificity exchanger and appropriate transcriptional and translational control signals. The expression construct can then be transfected to cells. After the transfected cells express the specificity exchanger, the specificity exchanger can be purified or isolated from the cells or cell supernatent. It is important to note that any recombinant methodology can be used to synthesize the specificity exchangers described herein, including, for example, in vitro recombinant DNA techniques, synthetic techniques, and in vivo genetic recombination.

Alternatively, RNA capable of encoding a specificity exchanger can be chemically synthesized using, for example, synthesizers. See, for example, the techniques described in *Oligonucleotide Synthesis*, 1984, Gait, M. J. ed., IRL Press, Oxford, which is incorporated by reference herein in its entirety.

A variety of host-expression vector systems can be utilized to express the specificity exchangers. Where the specificity exchanger is a soluble molecule it can be recovered from the culture, i.e., from the host cell in cases where the peptide or polypeptide is not secreted, and from the culture media in cases where the peptide or polypeptide is secreted by the cells. However, the expression systems also encompass engineered host cells that express membrane bound specificity exchangers. Purification or enrichment of the specificity exchangers from such expression systems can be accomplished using appropriate detergents and lipid micelles and methods well known to those skilled in the art.

The expression systems that can be used include, but are not limited to, microorganisms such as bacteria (e.g., *E. coli* or *B. subtilis*) transformed with recombinant bacteriophage DNA, plasmid DNA or cosmid DNA expression vectors containing nucleotide sequences encoding a specificity exchanger; yeast (e.g., *Saccharomyces, Pichia*) transformed with recombinant yeast expression vectors containing nucleotide sequences encoding specificity exchangers; insect cell systems infected with recombinant virus expression vectors (e.g., *Baculovirus*) containing nucleic acids encoding the specificity exchangers; or mammalian cell systems (e.g., HeLa, COS, CHO, BHK, 293, or 3T3 cells) harboring recombinant expression constructs containing nucleic acids encoding specificity exchangers.

In bacterial systems, a number of expression vectors can be advantageously selected depending upon the use intended for the specificity exchanger. For example, when a large quantity is desired (e.g., for the generation of pharmaceutical compositions of specificity exchangers) vectors that direct the expression of high levels of fusion protein products that are readily purified can be desirable. Such vectors include, but are not limited, to the *E. coli* expression vector pUR278 (Ruther et al., *EMBO J.*, 2:1791 (1983), in which the specificity exchanger coding sequence can be ligated individually into the vector in frame with the lacZ coding region so that a fusion protein is produced; pIN vectors (Inouye & Inouye, *Nucleic Acids Res.*, 13:3101–3109 (1985); Van Heeke & Schuster, *J. Biol. Chem.*, 264:5503–5509 (1989)); and the like. The pGEX vectors can also be used to express foreign polypeptides as fusion proteins with glutathione S-transferase (GST). In general, such fusion proteins are soluble and can be purified from lysed cells by adsorption to glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The specificity exchanger gene coding sequence can be cloned individually into non-essential regions (for example the polyhedrin gene) of the virus and placed under control of an AcNPV promoter (for example the polyhedrin promoter). Successful insertion of a specificity exchanger gene coding sequence will result in inactivation of the polyhedrin gene and production of non-occluded recombinant virus, (i.e., virus lacking the proteinaceous coat coded for by the polyhedrin gene). These recombinant viruses are then used to infect *Spodoptera frugiperda* cells in which the inserted gene is expressed. (E.g., see Smith et al., *J. Virol.* 46: 584 (1983); and Smith, U.S. Pat. No. 4,215,051).

In mammalian host cells, a number of viral-based expression systems can be utilized. In cases where an adenovirus is used as an expression vector, a nucleic acid sequence encoding a specificity exchanger can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing the specificity exchanger gene product in infected hosts. (See e.g., Logan & Shenk, *Proc. Natl. Acad. Sci. USA* 81:3655–3659 (1984)). Specific initiation signals can also be required for efficient translation of inserted specificity exchanger nucleotide sequences (e.g., the ATG initiation codon and adjacent sequences). In most cases, an exogenous translational control signal, including, perhaps, the ATG initiation codon, should be provided. Furthermore, the initiation codon should be in phase with the reading frame of the desired coding sequence to ensure translation of the entire insert. These exogenous translational control signals and initiation codons can be of a variety of origins, both natural and synthetic. The efficiency of expression can also be enhanced by the inclusion of appropriate transcription enhancer elements, transcription terminators, etc. (See Bittner et al., *Methods in Enzymol.*, 153:516–544 (1987)).

In addition, a host cell strain can be chosen that modulates the expression of the inserted sequences, or modifies and processes the gene product in the specific fashion desired. Such modifications (e.g., glycosylation) and processing (e.g., cleavage) of protein products can be important for some embodiments. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product can be used. Such mammalian host cells include, but are not limited to, HeLa, CHO, VERO, BHK, HeLa, COS, MDCK, 293, 3T3, and W138 cells.

For long-term, high-yield production of recombinant proteins, stable expression is preferred. For example, cell lines that stably express the specificity exchangers described above can be engineered. Rather than using expression vectors that contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells are allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn are cloned and expanded into cell lines. This method is advantageously used to engineer cell lines which express a specificity exchanger.

A number of selection systems can be used, including but not limited to the herpes simplex virus thymidine kinase (Wigler, et al., *Cell* 11:223 (1977)), hypoxanthine-guanine phosphoribosyltransferase (Szybalska & Szybalski, *Proc. Natl. Acad. Sci. USA* 48:2026 (1962)), and adenine phosphoribosyltransferase (Lowy, et al., *Cell* 22:817 (1980)) genes can be employed in tk$^-$, hgprt$^-$ or aprt$^-$ cells, respectively. Also, antimetabolite resistance can be used as the basis of selection for the following genes: dhfr, which confers resistance to methotrexate (Wigler, et al., *Proc. Natl. Acad. Sci. USA* 77:3567 (1980)); O'Hare, et al., *Proc. Natl. Acad. Sci. USA* 78:1527 (1981)); gpt, which confers resistance to mycophenolic acid (Mulligan & Berg, *Proc. Natl.*

*Acad. Sci. USA* 78:2072 (1981)); neo, which confers resistance to the aminoglycoside G-418 (Colberre-Garapin, et al., *J. Mol. Biol.* 150:1 (1981)); and hygro, which confers resistance to hygromycin (Santerre, et al., *Gene* 30:147 (1984)). The following section describes several types of in vitro and in vivo characterization assays that can be used to identify specificity exchangers that bind to pathogens and redirect antibodies present in a subject to the pathogen.

Specificity Exchanger Characterization Assays

Preferably, after a specificity exchanger is synthesized it is analyzed for its ability to interact with a receptor or antigen and/or the ability to interact with an antibody that is specific for the antigenic domain. The term "characterization assay" refers to an assay, experiment, or analysis made on a specificity exchanger, which evaluates the ability of a specificity exchanger to interact with a receptor or antigen (e.g., a surface receptor or protein present in bacteria, virus, mold, or fungi) and/or an antibody present in a subject or made to be present in a subject (e.g., an antibody that recognizes an epitope or peptide of a pathogen that is part of an antigenic domain), or effect the proliferation of a pathogen. Encompassed by the term "characterization assay" are binding studies (e.g., enzyme immunoassays (EIA), enzyme-linked immunoassays (ELISA), competitive binding assays, computer generated binding assays, support bound binding studies, and one and two hybrid systems), and infectivity studies (e.g., reduction of viral infection, propagation, and attachment to a host cell). For example, some in vitro characterization assays evaluate the ability of a specificity exchanger to bind to a support having a receptor or antigen of a pathogen or fragment thereof disposed thereon or vice versa. Other in vitro characterization assays assess the ability of a specificity exchanger to bind to an antibody specific for the antigenic domain of the specificity exchanger.

Several of these types of in vitro approaches employ a multimeric specificity exchanger, specificity domain, or antigenic domain, as described above. For example, a support-bound ligand/receptor specificity exchanger can be contacted with "free" adhesion receptors and an association can be determined directly (e.g., by using labeled adhesion receptors) or indirectly (e.g., by using a labeled ligand directed to an adhesion receptor). Thus, candidate ligand/receptor specificity exchangers are identified as bona fide ligand/receptor specificity exchangers by virtue of the association of the receptors with the support-bound candidate ligand/receptor specificity exchanger. Alternatively, support-bound adhesion receptors can be contacted with "free" ligand/receptor specificity exchangers and the amount of associated ligand/receptor specificity exchanger can be determined directly (e.g., by using labeled ligand/receptor specificity exchanger) or indirectly (e.g., by using a labeled antibody directed to the antigenic domain of the ligand/receptor specificity exchanger). Similarly, by using an antibody specific for the antigenic domain of a specificity exchanger disposed on a support and labeled specificity exchanger (or a secondary detection reagent, e.g., a labeled receptor or antibody to the specificity exchanger) the ability of the antibody to bind to the antigenic domain of the specificity exchanger can be determined. Additionally, some characterization assays are designed to determine whether a specificity exchanger can bind to both the target and the redirected antibody.

Cellular characterization assays are also employed to evaluate the ability of the specificity exchanger to bind to a pathogen or affect infection or proliferation of the pathogen in cultured cells. In vivo characterization assays are also employed to evaluate the ability of specificity exchangers to redirect antibodies to a pathogen or to reduce the proliferation of a pathogen in diseased animals. In general, the characterization assays can be classified as: (1) in vitro characterization assays, (2) cellular characterization assays, and (3) in vivo characterization assays. A discussion of each type of characterization assay is provided in the following sections.

In Vitro Characterization Assays

There are many types of in vitro assays that can be used to determine whether a specificity exchanger binds to a particular receptor or antigen and whether an antibody found in a subject can bind to the antigenic domain of the specificity exchanger. Most simply, the receptor or antigen is bound to a support (e.g., a petri dish) and the association of the specificity exchanger with the receptor or antigen is monitored directly or indirectly, as described above. Similarly, a primary antibody directed to the antigenic domain of a specificity exchanger (e.g., an antibody found in a subject) can be bound to a support and the association of the specificity exchanger with the primary antibody can be determined directly (e.g., using labeled specificity exchanger) or indirectly (e.g., using labeled receptor, antigen or a labeled secondary antibody that interacts with an epitope on the specificity exchanger that does not compete with the epitope recognized by the primary antibody).

Another approach involves a sandwich-type assay, wherein the receptor or antigen is bound to a support, the specificity exchanger is bound to the receptor or antigen, and the primary antibody is bound to the specificity exchanger. If labeled primary antibody is used, the presence of a receptor or antigen/specificity exchanger/primary antibody complex can be directly determined. The presence of the receptor or antigen/specificity exchanger/primary antibody complex can also be determined indirectly by using, for example, a labeled secondary antibody that reacts with the primary antibody at an epitope that does not interfere with the binding of the primary antibody to the specificity exchanger. In some cases, it may be desired to use a labeled tertiary antibody to react with an unlabeled secondary antibody, thus, forming a receptor or antigen/specificity exchanger/primary antibody/secondary antibody/labeled tertiary antibody complex.

The following examples (EXAMPLES 1–5) describe the preparation and characterization of antigen/antibody specificity exchangers. EXAMPLE 1 describes the preparation of several antigen/antibody specificity exchangers.

EXAMPLE 1

The antigen/antibody specificity exchangers provided in TABLE IV are synthetic peptides synthesized according to a method for multiple peptide synthesis and by a Milligen 9050 peptide synthesizer using 9-fluorenylmethoxy-carbonyl-protected amino acid esters. These peptides were analysed and/or purified by reverse phase HPLC using a Pep-S 5 m column (Pharmacia-LKB, Uppsala, Sweden), run with a gradient from 10% to 60% CH3CN against water containing 0.1% trifluoro-acetic acid.

TABLE IV

| | | |
|---|---|---|
| Peptide 1: | CDLIYYDYEEDYYFPPNAPILS | (SEQ ID NO: 118) |
| Peptide 2: | CDLIYYDYEEDYYFRPPNAPILST | (SEQ ID NO: 119) |
| Peptide 3: | CDLIYYDYEEDYYFKEIPALTAVETG | (SEQ ID NO: 120) |
| Peptide 4: | CDLIYYDYEEDYYFPAHSKEIPALTA | (SEQ ID NO: 121) |
| Peptide 5: | CDLIYYDYEEDYYFWGCSGKLICT | (SEQ ID NO: 122) |
| Peptide 6: | CDLIYYDYEEDYYFCTTAVPWNAS | (SEQ ID NO: 123) |
| Peptide 7: | CDLIYYDYEEDYYFKRPPNAPILSTCDLIYYDYEEDYYF | (SEQ ID NO: 124) |
| Peptide 8: | TYAMNPPNAPILS | (SEQ ID NO: 125) |
| Peptide 9: | RVRSKSFNYATYYADSVKGPPNAPILS | (SEQ ID NO: 126) |
| Peptide 10: | PAQGIYFDYGGFAYPPNAPILS | (SEQ ID NO: 127) |
| Peptide 11: | CDLIYYDYEEDYYQRKTKRNTNRR | (SEQ ID NO: 128) |

TABLE V illustrates the specific regions of the antigen/antibody specificity exchangers provided in TABLE IV. These antigen/antibody specificity exchangers include specificity domains that comprise peptides containing the CDRH3 domain of mAb F58 or CDRH1, CDRH2, CDRH3 domain of mAb C1–5. These antigen/antibody specificity exchangers further comprise antigenic domains obtained from various viral proteins.

TABLE V

| Peptide No. | Specificity Domain | link | Antigenic Domain | Source of Antigenic Domain aas |
|---|---|---|---|---|
| 1. | SEQ ID NO 43 | peptide bond | SEQ ID NO 65 | HBc/eAg, aas 134–141 |
| 2. | SEQ ID NO 43 | peptide bond | SEQ ID NO 66 | HBc/eAg, aas 133–142 |
| 3. | SEQ ID NO 43 | peptide bond | SEQ ID NO 67 | Polio VP1, aas 39–50 |
| 4. | SEQ ID NO 43 | peptide bond | SEQ ID NO 68 | Polio VP1, aas 35–46 |
| 5. | SEQ ID NO 43 | peptide bond | SEQ ID NO 69 | HIV-1 gp41, aas 596–605 |
| 6. | SEQ ID NO 43 | peptide bond | SEQ ID NO 70 | HIV-1 gp41, aas 603–612 |
| 7. | 2(SEQ ID NO 43) | Lys | SEQ ID NO 66 | HBc/eAg, aas 133–142 |
| 8. | SEQ ID NO 45 | peptide bond | SEQ ID NO 65 | HBc/eAg, aas 134–141 |
| 9. | SEQ ID NO 46 | peptide bond | SEQ ID NO 65 | HBc/eAg, aas 134–141 |
| 10. | SEQ ID NO 47 | peptide bond | SEQ ID NO 65 | HBc/eAg, aas 134–141 |
| 11. | SEQ ID NO 44 | peptide bond | SEQ ID NO 71 | HCV core 8–18 |

Note: aas = amino acids

The following example describes an evaluation of the ability of the specificity exchangers described in EXAMPLE 1 to bind to antigen.

EXAMPLE 2

The specificity exchangers prepared in EXAMPLE 1 were then evaluated using enzyme immuno assays (EIAS). Strain-specific HIV-1 V3 peptides were coated on microtiter wells (Nunc 96F Certificated; Nunc, Copenhagen, Denmark) in 100 ml portions at concentrations of from 10 mg/ml to 0.01 mg/ml in 0.05 M sodium carbonate buffer, pH 9.6, overnight at +4° C. Excess peptides were removed by washing with PBS containing 0.05% Tween 20. The peptide-coated plates were assayed for binding using the specificity exchangers prepared in EXAMPLE 1, diluted from 100 mg/ml to 0.01 mg/ml in PBS containing 1% BSA, 2% goat serum, and 0.05% Tween 20. The dilutions of these specificity exchangers were added in 100 ml portions and incubated with the adsorbed V3 peptides for 60 minutes at +37° C. Excess specificity exchangers were removed by washing. Bound specificity exchangers were indicated using the respective mAb or anti-serum and incubating for 60 minutes at +37° C. The amount of bound antibody was indicated by an additional incubation of enzyme-labeled secondary antibody, rabbit anti-mouse Ig (P260, Dako, Copenhagen, Denmark) for mAbs, and goat anti-human IgG (A-3150; Sigma Chemicals, St. Louis, Mo.) for human antibodies. The amount of bound conjugate was determined by addition of substrate and the absorbencies were measured at 492 nm or 405 nm in a spectrophotometer. When adsorbed to microplates all specificity exchangers provided in TABLE IV except for Peptide Nos. 4 and 7 were found to be reactive with the respective antibodies. TABLE VI provides the binding results for Peptides 1–4.

TABLE VI

| Peptide | Antibody | Amount peptide added (ng/0.1 ml) to solid phase | | | | | |
|---|---|---|---|---|---|---|---|
| No. | used | 1,000 | 100 | 10 | 1 | 0.1 | 0.01 |
| 1 | 14E11 | 2.500 | 1.675 | 0.030 | 0.010 | 0.009 | 0.008 |
| 2 | 14E11 | 2.500 | 1.790 | 0.008 | 0.006 | 0.008 | 0.006 |
| 3 | CBV | 2.500 | 1.142 | 0.036 | 0.020 | 0.019 | 0.036 |
| | human A | 1.945 | 1.850 | 0.486 | 0.088 | 0.115 | 0.116 |
| | human B | 1.342 | 0.770 | 0.130 | 0.065 | 0.090 | 0.095 |
| 4 | CBV | 0.020 | 0.018 | 0.015 | 0.016 | 0.017 | 0.018 |
| | human A | 0.059 | 0.081 | 0.108 | 0.109 | 0.097 | 0.100 |
| | human B | 0.052 | 0.072 | 0.091 | 0.098 | 0.083 | 0.100 |

Note: Regression analysis of the relation between absorbance and peptide concentration gives $p < 0.01$.

The next example demonstrates the ability of the antigen/antibody specificity exchangers described in EXAMPLE 1 to simultaneously bind to a particular antigen, HIV-1 V3 peptide, MN-strain, and antibodies that are specific for the respective antigenic domains.

EXAMPLE 3

As indicated by data shown in TABLES VII, VIII, and IX, all of the HIV-specific antigen/antibody specificity exchangers were found to directly bind to the HIV-1 V3 peptide. The data provided in TABLES VII, VIII, and IX also show that the reactivity to the HIV-1 V3 peptide was found to be dependent on both concentrations of the specificity exchangers and the V3 peptides, indicating a specific reactivity.

TABLE VII illustrates the ability of the antigen/antibody specificity exchanger to simultaneously bind the HIV-1 V3 peptide antigen (vis a vis the CDR sequence of the specificity domain) and the monoclonal antibodies specific for the particular antigenic domain of the specificity exchangers. Values are given as the absorbance at 492 nm. TABLE VIII illustrates the ability of the antigen/antibody specificity exchanger to simultaneously bind the HIV-1 V3 peptide antigen (vis a vis the CDR sequence of the specificity domain) and human anti-polio VP1 polyclonal antibodies specific for the antigenic region on the tested specificity exchanger. Values are given as the absorbance at 405 nm. TABLE IX illustrates the ability of the antigen/antibody specificity exchanger to simultaneously bind the HIV-1 V3 peptide antigen (vis a vis the CDR sequence of the specificity domain) and the human anti-HCV core polyclonal anti-bodies specific for the antigenic region on the tested specificity exchanger. Values are given as the absorbance at 405 nm.

The results provided in TABLES VII, VIII, and IX clearly show that antibodies specific for HIV-1 gp41, HBc/eAg, poliovirus 1 VP 1, and HCV core proteins were redirected to the HIV-1 V3 peptide antigen. It was also found, that pre-incubation of equimolar concentrations of mAb 14E11 and the corresponding specificity exchanger did not alter the ability of the specificity exchanger complex to bind to the V3 peptide. This indicated that antigenic domains could be joined to a CDR peptide (a specificity domain) while retaining the antigen binding ability of the specificity domain.

TABLE VII a:

| Peptide No. | Anti-body used | Amount of test peptide (ng/0.1 ml) | Amount V3 peptide added (ng/0.1 ml) to solid phase | | | | | |
|---|---|---|---|---|---|---|---|---|
| | | | 1,000 | 500 | 250 | 125 | 62.5 | 31.25 |
| 1 | 14E11 | 10,000 | 2.500 | 2.500 | 2.500 | 2.338 | 1.702 | 1.198 |
| | | 5,000 | 2.500 | 2.500 | 2.500 | 2.190 | 1.622 | 1.122 |
| | | 2,500 | 2.500 | 2.500 | 2.500 | 2.039 | 1.394 | 0.990 |
| | | 1,250 | 2.500 | 2.500 | 2.500 | 1.712 | 0.930 | 0.771 |
| | | 625 | 1.936 | 0.824 | 0.380 | 0.152 | 0.056 | 0.053 |
| | | 312 | 0.196 | 0.085 | 0.044 | 0.043 | 0.030 | 0.025 | b:

| Peptide No. | Anti-body used | Amount of test peptide (ng/0.1 ml) | Amount V3 peptide added (ng/0.1 ml) | | | | | |
|---|---|---|---|---|---|---|---|---|
| | | | 1,000 | 500 | 250 | 125 | 62.5 | 31.25 |
| 4 | 14E11 | 10,000 | 2.500 | 2.500 | 2.133 | 1.560 | 1.070 | 0.829 |
| | | 5,000 | 2.500 | 2.500 | 1.963 | 1.645 | 1.074 | 0.981 |
| | | 2,500 | 2.500 | 2.500 | 1.729 | 1.404 | 0.962 | 0.747 |
| | | 1,250 | 2.500 | 2.424 | 1.433 | 1.327 | 0.795 | 0.488 |
| | | 625 | 0.835 | 0.359 | 0.200 | 0.120 | 0.088 | 0.073 |
| | | 312 | 0.099 | 0.054 | 0.042 | 0.049 | 0.045 | 0.025 |

TABLE VII-continued c:

| Peptide No. | Anti-body used | Amount of test peptide (ng/0.1 ml) | Amount V3 peptide added (ng/0.1 ml) to solid phase | | | | | |
|---|---|---|---|---|---|---|---|---|
| | | | 1,000 | 100 | 10 | 1 | 0.1 | 0.01 |
| 3 | CBV | 10,000 | 0.523 | 0.498 | 0.162 | 0.161 | 0.017 | 0.017 |
| | | 1,000 | 0.053 | 0.054 | 0.031 | 0.027 | 0.010 | 0.010 |
| | | 100 | 0.034 | 0.037 | 0.025 | 0.029 | 0.010 | 0.010 |
| | | 10 | 0.023 | 0.022 | 0.014 | 0.014 | 0.010 | 0.009 |
| | | 1 | 0.013 | 0.044 | 0.014 | 0.017 | 0.027 | 0.009 |
| | | 0.1 | 0.011 | 0.009 | 0.008 | 0.032 | 0.013 | 0.013 |

Note: Regression analysis of the relation between absorbance and CDR peptide concentration, and relation between absorbance and V3 peptide concentration gives $p < 0.01$, respectively.

TABLE VIII a:

| Peptide No. | Anti-body used | Amount of test peptide (ng/0.1 ml) | Amount V3 peptide added (ng/0.1 ml) to solid phase | | | | | |
|---|---|---|---|---|---|---|---|---|
| | | | 1,000 | 500 | 250 | 125 | 62.5 | 31.25 |
| 3 | human A | 10,000 | 1.538 | 1.356 | 1.448 | 1.052 | 0.280 | 0.123 |
| | | 5,000 | 1.179 | 1.050 | 1.006 | 0.557 | 0.136 | 0.087 |
| | | 2,500 | 0.684 | 0.558 | 0.604 | 0.216 | 0.084 | 0.067 |
| | | 1,250 | 0.367 | 0.358 | 0.332 | 0.162 | 0.075 | 0.062 |
| | | 625 | 0.228 | 0.238 | 0.220 | 0.121 | 0.083 | 0.063 |
| | | 312 | 0.171 | 0.154 | 0.154 | 0.103 | 0.072 | 0.060 | b:

| Peptide No. | Anti-body used | Amount of test peptide (ng/0.1 ml) | Amount V3 peptide added (ng/0.1 ml) to solid phase | | | | | |
|---|---|---|---|---|---|---|---|---|
| | | | 1.000 | 500 | 250 | 125 | 62.5 | 31.25 |
| 3 | human B | 10,000 | 0.366 | 0.352 | 0.352 | 0.200 | 0.074 | 0.056 |
| | | 5,000 | 0.206 | 0.217 | 0.188 | 0.131 | 0.063 | 0.053 |
| | | 2,500 | 0.134 | 0.132 | 0.126 | 0.091 | 0.061 | 0.055 |
| | | 1,250 | 0.107 | 0.114 | 0.108 | 0.077 | 0.060 | 0.054 |
| | | 625 | 0.082 | 0.104 | 0.087 | 0.075 | 0.063 | 0.056 |
| | | 312 | 0.083 | 0.091 | 0.094 | 0.077 | 0.068 | 0.060 |

Note: Regression analysis of the relation between absorbance and CDR peptide concentration, and relation between absorbance and V3 peptide concentration gives $p < 0.01$, respectively.

TABLE IX

| Peptide No. | Anti-body used | Amount of V3 peptide (ng/0.1 ml) | Amount of test peptide added (ng/0.1 ml) | | | | | |
|---|---|---|---|---|---|---|---|---|
| | | | 62 | 31 | 15 | 7.5 | 3.7 | 1.8 |
| 11 | human HCV-C | 625 | 2.500 | 2.416 | 2.097 | 1.473 | 0.973 | 0.630 |
| | | 78 | 2.500 | 2.335 | 1.781 | 1.225 | 0.825 | 0.564 |
| | | 39 | 2.389 | 2.287 | 1.626 | 1.081 | 0.664 | 0.389 |
| 11 | human HCV-D | 625 | 1.999 | 1.490 | 1.184 | 0.751 | 0.458 | 0.428 |
| | | 78 | 1.758 | 1.370 | 1.025 | 0.612 | 0.468 | 0.380 |
| | | 39 | 1.643 | 0.993 | 0.833 | 0.497 | 0.343 | 0.287 |
| 11 | human HCV-E | 625 | 2.368 | 2.165 | | 1.104 | 0.645 | 0.462 |
| | | 78 | 2.156 | 1.824 | 1.396 | 0.733 | 0.514 | 0.352 |
| | | 39 | 1.893 | 1.683 | 1.110 | 0.756 | 0.310 | 0.272 |

The next example demonstrates the ability of the antigen/antibody specificity exchangers to simultaneously bind to another antigen, residues 71–90 of HBc/eAg with an Ile at position 80, and antibodies that are specific for the respective antigenic domains.

EXAMPLE 4

The ability of antigen/antibody specificity exchangers to redirect antibodies was further evaluated in a system where the CDRH1, CDRH2 and CDRH3 sequences from mAb C1–5 were added to the epitope sequence for mAb 14E11 (residues 135–141 of the HBc/eAg sequence (PNAPILS SEQ ID No. 116). A peptide corresponding to the epitope sequence for mAb C1–5, residues 71–90 of HBc/eAg with an Ile at position 80, was adsorbed to microplates. The antigen/-antibody specificity exchangers, based on the C1–5 CDRs, were then added, and the amount bound CDR peptide was indicated by the epitope specific mAb 14E11. The results provided in TABLE X clearly show that the mAb 14E11 was redirected by the antigen/antibody specificity exchanger containing the CDRH2 sequence to the PNAPILS (SEQ ID No. 116) sequence. Also, this reactivity was dependent on the amount specificity exchanger added, indicating a specific reaction (p<0.01, Regression analysis).

TABLE XI

| HIV-1 V3 peptide attached to solid-phase | Reactivity (absorbance at 405 nm) of specificity exchanger peptide added in the indicated amount (ng) | | | | | |
|---|---|---|---|---|---|---|
| | 500 | 250 | 125 | 62.5 | 31.25 | 15.625 |
| Subtype A | 0.378 | 0.126 | 0.078 | 0.068 | 0.062 | 0.017 |
| Subtype B | 2.686 | 2.536 | 1.710 | 1.329 | 0.360 | 0.157 |
| Subtype C | 1.261 | 0.514 | 0.111 | 0.077 | 0.051 | 0.020 |
| Subtype D | 0.17 | 0.079 | 0.065 | 0.028 | 0.029 | 0.026 |
| Subtype E | 0.22 | 0.090 | 0.093 | 0.032 | 0.063 | 0.030 |

The following examples (EXAMPLES 6–8) describe the preparation and characterization of ligand/receptor specificity exchangers. EXAMPLE 6 describes a characterization assay that was performed to determine whether a specificity domain derived from the C-terminal domain of fibrinogen inhibits the binding of clumping factor (Clf) to fibrinogen.

EXAMPLE 6

In this example, several peptides corresponding to the C-terminal domain of fibrinogen (Fib) were analyzed for

TABLE X

| CDR sequence | Antibody used | Amount c71-90 peptide (ng/0.1 ml) | Amount of test peptide added (ng/0.1 ml) | | | | | |
|---|---|---|---|---|---|---|---|---|
| | | | 10.000 | 5.000 | 2.500 | 1.250 | 625 | 312 |
| Peptide 8: | 14E11 | 625 | 0.003 | 0.002 | 0.002 | 0.002 | 0.002 | 0.002 |
| CDRH1 | | 312 | 0.002 | 0.002 | 0.004 | 0.003 | 0.006 | 0.004 |
| (SEQ ID NO 45) | | 78 | 0.003 | 0.003 | 0.005 | 0.005 | 0.003 | 0.003 |
| Peptide 9: | 14E11 | 625 | 2.500 | 1.303 | 0.070 | 0.012 | 0.003 | 0.002 |
| CDRH2 | | 312 | 2.500 | 1.070 | 0.058 | 0.011 | 0.003 | 0.002 |
| (SEQ ID NO 46) | | 78 | 2.500 | 0.868 | 0.039 | 0.008 | 0.003 | 0.003 |
| Peptide 10: | 14E11 | 625 | 0.004 | 0.003 | 0.004 | 0.003 | 0.003 | 0.003 |
| CDRH3 | | 312 | 0.004 | 0.003 | 0.004 | 0.004 | 0.003 | 0.003 |
| (SEQ ID NO 47) | | 78 | 0.005 | 0.004 | 0.005 | 0.005 | 0.004 | 0.004 |

The next example provides more evidence that antigen/antibody specificity exchangers redirect antibodies.

EXAMPLE 5

This example describes experiments that verified that antigen/antibody specificity exchangers containing a CDRH3 sequence, a specificity domain directed to an HIV-1 antigen, and an antigenic domain that contains an HBc/eAg epitope recognized by mAb 14E11 redirected HBc/eAg specific antibody to HIV-1 V3 peptides of several different subtypes. As shown in TABLE XI, the HBc/eAg specific antibody efficiently bound to the specificity exchangers that were also bound to the HIV-1 antigen, which was affixed to microtiter plates. Thus, antigen/antibody specificity exchangers effectively redirect antibodies antigens that are present on pathogens.

their ability to block the binding of clumping factor (Clf) to fibrinogen. (See TABLE XII). These peptides were manufactured using standard techniques in peptide synthesis using finoc chemistry (Syro, MultiSynTech, Germany). Preferably, the peptides are purified by reverse-phase HPLC. A competition enzyme immunoassay was then performed to determine whether the peptides were able to block the interaction between Clf and fibrinogen. The results of these experiments are shown in TABLE XII. The smallest peptide from fibrinogen found to inhibit the interaction between Clf and fibrinogen was HLGGAKQAGD (SEQ. ID No. 117). Substitution of the first two amino acids of this peptide with alanine and lysine had a significant effect on the ability of the peptide to block the interaction between Clf and fibrinogen (e.g., the peptide ALGGAKQAGD (SEQ. ID No. 129) was unable to block the Clf/fibrinogen interaction).

TABLE XII

| Seq. ID No. | (Fib) peptide | Inhibition of (Fib/Clf) interaction |
|---|---|---|
| 130 | LTIGEGQQHHLGGAKQAGDV | + |

TABLE XII-continued

| Seq. ID No. | (Fib) peptide | Inhibition of (Fib/Clf) interaction |
|---|---|---|
| 131 | GEGQQHHLGGAKQAGDV | + |
| 132 | QQHHLGGAKQAGDV | + |
| 133 | QHHLGGAKQAGDV | + |
| 134 | HHLGGAKQAGDV | + |
| 135 | HLGGAKQAGDV | + |
| 136 | LGGAKQAGDV | – |
| 137 | GGAKQAGDV | – |
| 138 | GAKQAGDV | – |
| 139 | QHHLGGAKQAGD | + |
| 140 | QHHLGGAKQAG | + |
| 141 | QHHLGGAKQA | – |
| 142 | QHHLGGAKQ | – |
| 143 | QHHLGGAK | +/– |
| 144 | QHHLGGA | – |
| 145 | HHLGGAKQAGDV | + |
| 146 | HHLGGAKQAGD | + |
| 147 | HHLGGAKQAG | + |
| 148 | HLGGAKQAGDV | + |
| 149 | HLGGAKQAGD | + |
| 150 | ALGGAKQAG | – |
| 151 | HAGGAKQAG | + |
| 152 | HLAGAKQAG | + |
| 153 | HLGAAKQAG | + |
| 154 | HLGGGKQAG | + |
| 155 | HLGGAAQAG | +/– |
| 156 | HLGGAKAAG | + |
| 157 | HLGGAKQGG | + |
| 158 | HLGGAKQAA | + |

The next example describes the preparation and characterization of several ligand/receptor specificity exchangers that interact with the ClfA receptor found on *Staphylococcus*.

EXAMPLE 7

Ligand/receptor specificity exchangers having specificity domains (approximately 20 amino acids long) corresponding to various regions of the fibrinogen gamma-chain sequence were produced using standard techniques in peptide synthesis using fmoc chemistry (Syro, MultiSynTech, Germany) and these ligand/receptor specificity exchangers were analyzed for their ability to bind the ClfA receptor and an antibody specific for their respective antigenic domains. The sequences of these ligand/receptor specificity exchangers are listed in TABLE XIII and are provided in the Sequence listing (SEQ. ID. Nos. 72–115). The ligand/receptor specificity exchangers used in this analysis have an antigenic domain that comprises a peptide having an epitope of herpes simplex virus gG2 protein, which is recognized by a monoclonal antibody for herpes simplex virus gG2 proteins. Serial dilutions of these ligand/receptor specificity exchangers were made in phosphate buffered saline (PBS) containing 2 µg/ml goat serum. (Sigma Chemicals, St. Louis, Mo.) and 0.5% Tween 20 (PBS-GT). The receptor ClFA was passively adsorbed at 10 µg/ml to 96 well microtiter plates in 50 mM sodium carbonate buffer, pH 9.6, overnight at +4° C.

The diluted ligand/receptor specificity exchangers were then incubated on the plates for 60 minutes. The ability of the ligand/receptor specificity exchanger to interact with the receptor was determined by applying a primary antibody to the plate and incubating for 60 minutes (a 1:1000 dilution of mAb for herpes simplex virus gG2 proteins). The bound primary mAb was then indicated by a rabbit anti-mouse IgG (Sigma) secondary antibody and a peroxidase labeled goat anti-rabbit IgG (Sigma) tertiary antibody. The plates were developed by incubation with dinitro-phenylene-diamine (Sigma) and the absorbance at 405 nm was analyzed.

Every ligand/receptor specificity exchanger provided in TABLE XIII (SEQ. ID. Nos. 72–115) appreciably bound the immobilized ClfA and also bound the mAb specific for HSV gG2 protein. Accordingly, these ligand/receptor specificity exchangers redirected antibodies specific for HSV to a receptor found on a pathogen. Preferred ligand/receptor specificity exchangers are also provided in TABLE XIV.

TABLE XIII

LIGAND/RECEPTOR SPECIFICITY EXCHANGERS

| | |
|---|---|
| YGEGQQHHLGGAKQAGDVHRGGPEEF | (SEQ. ID. No. 72) |
| YGEGQQHHLGGAKQAGDVHRGGPEE | (SEQ. ID. No. 73) |
| YGEGQQHHLGGAKQAGDVSTPLPETT | (SEQ. ID. No. 74) |

TABLE XIII-continued

| LIGAND/RECEPTOR SPECIFICITY EXCHANGERS | |
|---|---|
| MSWSLHPRNLILYFYALLFLHRGGPEE | (SEQ. ID. No. 75) |
| ILYFYALLFLSTCVAYVATHRGGPEE | (SEQ. ID. No. 76) |
| SSTCVAYVATRDNCCILDERHRGGPEE | (SEQ. ID. No. 77) |
| RDNCCILDERFGSYCPTTCGHRGGPEE | (SEQ. ID. No. 78) |
| FGSYCPTTCGIADFLSTYQTHRGGPEE | (SEQ. ID. No. 79) |
| IADFLSTYQTKVDKDLQSLEHRGGPEE | (SEQ. ID. No. 80) |
| KVDKDLQSLEDILHQVENKTHRGGPEE | (SEQ. ID. No. 81) |
| DILHQVENKTSEVKQLIKAIHGGPEE | (SEQ. ID. No. 82) |
| SEVKQLIKAIQLTYNPDESSHRGGPEE | (SEQ. ID. No. 83) |
| QLTYNIPDESSKPNMIDAATLHRGGPEE | (SEQ. ID. No. 84) |
| KPNMIDAATLKSRIMLEEIMHRGGPEE | (SEQ. ID. No. 85) |
| KSRIMLEEIMKYEASTILTHDHRGGPEE | (SEQ. ID. No. 86) |
| KYEASILTHDSSIRYLQEIYHRGGPEE | (SEQ. ID. No. 87) |
| SSIRYLQEIYNSNNQKIVNLHRGGPEE | (SEQ. ID. No. 88) |
| NSNNQKIVNLKEKVAQLEAQHRGGPEE | (SEQ. ID. No. 89) |
| CQEPCKDTVQIHDITGKDCQHRGGPEE | (SEQ. ID. No. 90) |
| IHDITGKDCQDIANKGAKQSHRGGPEE | (SEQ. ID. No. 91) |
| DIANKGAKQSGLYFIKPLKAHRGGPEE | (SEQ. ID. No. 92) |
| GLYFIKPLKANQQFLVYCEIHRGGPEE | (SEQ. ID. No. 93) |
| NQQFLVYCEIDGSGNGWTVFHRGGPEE | (SEQ. ID. No. 94) |
| DGSGNGWTVFQKRLDGSVDFHRGGPEE | (SEQ. ID. No. 95) |
| QKRLDGSVDFKKNWIQYKEGHRGGPEE | (SEQ. ID. No. 96) |
| KKNWIQYKEGFGHLSPTGTTHRGGPEE | (SEQ. ID. No. 97) |
| FGHLSPTGTTEFWLGNEKIHHRGGPEE | (SEQ. ID. No. 98) |
| EFWLGNEKIHLISTQSAIPYHRGGPEE | (SEQ. ID. No. 99) |
| LISTQSAIPYALRVELEDWNHRGGPEE | (SEQ. ID. No. 100) |
| ALRVELEDWNGRTSTADYAMHRGGPEE | (SEQ. ID. No. 101) |
| GRTSTADYAMFKVGPEADKYHRGGPEE | (SEQ. ID. No. 102) |
| FKVGPEADKYRLTYAYFAGGHRGGPEE | (SEQ. ID. No. 103) |
| RLTYAYFAGGDAGDAFDGFDHRGGPEE | (SEQ. ID. No. 104) |
| DAGDAFDGFDFGDDPSDKFFHRGGPEE | (SEQ. ID. No. 105) |
| FGDDPSDKFFTSHNGMQFSTHRGGPEE | (SEQ. ID. No. 106) |
| TSHNGMQFSTWDNDNDKFEGHRGGPEE | (SEQ. ID. No. 107) |
| WDNDNDKFEGNCAEQDGSGWHRGGPEE | (SEQ. ID. No. 108) |
| NCAEQDGSGWWMNKCHAGHLHRGGPEE | (SEQ. ID. No. 109) |

TABLE XIII-continued

LIGAND/RECEPTOR SPECIFICITY EXCHANGERS

| | |
|---|---|
| WMNKCHAGHLNGVYYQGGTYHRGGPEE | (SEQ. ID. No. 110) |
| NGVYYQGGTYSKASTPNGYDHRGGPEE | (SEQ. ID. No. 111) |
| SKASTPNGYDNGTIIWATWKTHRGGPEE | (SEQ. ID. No. 112) |
| NGIIWATWKTRWYSMKKTTMHRGGPEE | (SEQ. ID. No. 113) |
| RWYSMKKTTMKIIPFNRLTIHRGGPEE | (SEQ. ID. No. 114) |
| KIIPFNRLTIGEGQQHHLGGAKQAGDVHRGGPEE | (SEQ. ID. No. 115) |

TABLE XIV

LIGAND/RECEPTOR SPECIFICITY EXCHANGERS

| Ligand/receptor Specificity Exchanger | Seq. ID No. |
|---|---|
| HRGGPEEF-HHLGGAKQAGD | 159 |
| HRGGPEEF-HHLGGAKRAGR | 160 |
| HRGGPEEF-HHLGGARRAGR | 161 |
| HRGGPEEF-HHLGHAKQAGR | 162 |
| HRGGPEEF-HHLGHARQAGR | 163 |
| HRGGPEEF-HHLGHAKRAGL | 164 |
| HRGGPEEF-HHLGHAKRAGR | 165 |
| HHLGGAKQAGD-HRGGPEEF | 166 |
| HHLGGAKRAGR-HRGGPEEF | 167 |
| HHLGGARRAGR-HRGGPEEF | 168 |
| HHLGHAKQAGR-HRGGPEEF | 169 |
| HHLGHARQAGR-HRGGPEEF | 170 |
| HHLGHAKRAGL-HRGGPEEF | 171 |
| HHLGHAKRAGR-HRGGPEEF | 172 |
| PALTAVETGATNPL-HHLGGAKQAGD | 173 |
| PALTAVETGATNPL-HHLGGAKRAGR | 174 |
| PALTAVETGATNPL-HHLGGARRAGR | 175 |
| PALTAVETGATNPL-HHLGHAKQAGR | 176 |
| PALTAVETGATNPL-HHLGHAR AGR | 177 |
| PALTAVETGATNPL-HHLGHAKRAGL | 178 |
| PALTAVETGATNPL-HHLGHAKRAGR | 179 |
| HHLGGAKQAGD-PALTAVETGATNPL | 180 |
| HHLGGAKRAGR-PALTAVETGATNPL | 181 |
| HHLGGARRAGR-PALTAVETGATNPL | 182 |
| HHLGHAKQAGR-PALTAVETGATNPL | 183 |
| HHLGHARQAGR-PALTAVETGATNPL | 184 |
| HHLGHAKRAGL-PALTAVETGATNPL | 185 |
| HHLGHAKRAGR-PALTAVETGATNPL | 186 |

The next example describes another characterization assay that was performed to determine whether ligand/receptor specificity exchangers bind to a receptor that is present on a bacteria and thereby redirect an antibody specific for the antigenic domain of the specificity exchanger to the bacterial receptor.

EXAMPLE 8

Ligand/receptor specificity exchangers having specificity domains that bind to clumping factor (Clf) and antigenic domains that correspond to an epitope derived from the polio virus were produced using standard techniques in peptide synthesis using fmoc chemistry (Syro, MultiSynTech, Germany). See TABLE XV. These ligand/receptor specificity exchangers were analyzed for their ability to inhibit the interaction between CLF and fibrinogen. In these experiments, the ligand/specificity exchangers described in TABLE XV were manufactured and various concentrations of these molecules were added to an enzyme competition immunoassay containing Clf and fibrinogen. The lowest inhibiting concentration, which is the lowest peptide concentration needed to inhibit the Clf/Fib interaction, was ascertained. Accordingly, the lower the concentration needed to inhibit the Fib/Clf interaction, the more effective the inhibitor. Additionally, the lowest solid-phase bound peptide concentration, which is the lowest tested concentration of peptide recognized by anti-poliovirus antibodies in the immunoassay, was determined. Some of the peptides used (e.g., CPALTAVETGCTNP-LAAHHLGGAKQAG (SEQ ID No. 187), HHLGGAKQAG-AA-CPALTAVETGCTNPL (SEQ ID No. 188), CPALTAVETGC-TNPLHHLGGAKQAG (SEQ ID No. 189), and HHLGGAKQAG-CPALTAVETGCTNPL (SEQ ID No. 190)), designated by asterisks in TABLE XV, were cyclized between the two artificially introduced cystiene residues. These experiments revealed that HHLGGAKQAG-AA-CPALTAVETGCTNPL* (SEQ ID No. 191) and HHLGGAKQAG-CPALTAVETGCTNPL (SEQ ID No. 190) effectively inhibited the interaction of Clf with fibrinogen and retained functional poliovirus epitopes.

TABLE XV

| SEQ ID | Peptide sequence | Lowest inhibiting Conc. (µ/ml) | Lowest epitope on solid-phase (µg/ml) |
|---|---|---|---|
| 192 | CPALTAVETGCTNPL-AA-HHLGGAKQAG* | >625 | 1.6 |
| 187 | CPALTAVETGCTNPL-AA-HHLGGAKQAG | 625 | 1.6 |
| 191 | HHLGGAKQAG-AA-CPALTAVETGCTNPL* | 69 | 8 |
| 188 | HHLGGAKQAG-AA-CPALTAVETGCTNPL | 625 | >200 |
| 193 | CPALTAVETGC-TNPLHHLGGAKQAG* | 625 | 1.6 |
| 189 | CPALTAVETGC-TNPLHHLGGAKQAG | 208 | 1.6 |
| 194 | HHLGGAKQAG-CPALTAVETGCTNPL* | 208 | >200 |
| 190 | HHLGGAKQAG-CPALTAVETGCTNPL | 23 | 1.6 |
| 195 | PALTAVETGATNPL-HHLGGAKQAG | >625 | 1.6 |
| 196 | HHLGGAKQAG-PALTAVETGATNPL | >625 | >200 |

The next section describes several cellular-based characterization assays that can be preformed to determine whether an antigen/antibody specificity exchanger or a ligand/receptor specificity exchanger binds to a pathogen or inhibits the proliferation of a pathogen.

Cell-based Characterization Assays

In another type of characterization assay, a cell-based approach is used to evaluate the ability of a specificity exchanger to bind to a pathogen and redirect an antibody specific for the antigenic domain of the ligand/receptor specificity exchanger to the pathogen. This analysis also reveals the ability of the specificity exchanger to inhibit proliferation of a pathogen because, in the body of a subject, the interaction of the ligand/receptor specificity exchanger with a pathogen and an antibody directed to the antigenic domain of the ligand/receptor specificity exchanger is followed by humoral and cellular responses that purge the pathogen from the subject (e.g., complement fixation and macrophage degradation).

In general, the cell-based characterization assays involve providing antigen/antibody specificity exchangers or ligand/receptor specificity exchangers to cultured pathogens and monitoring the association of the ligand/receptor specificity exchanger with the pathogen. Several types of cell-based characterization assays can be used and the example below describes some of the preferred characterization assays in greater detail.

EXAMPLE 9

One type of cell-based characterization assay involves binding of a specificity exchanger to bacteria disposed on a support. Accordingly, bacteria (e.g., *Staphylococcus aureus*, or *Escherichia coli*.) are grown in culture or on an agar plate in a suitable growth media (e.g., LB broth, blood broth, LB agar or blood agar). The cells are then transferred to a membrane (e.g., nitrocellulose or nylon) by either placing the culture on the membrane under vacuum (e.g., using a dot-blot manifold apparatus) or by placing the membrane on the colonies for a time sufficient to permit transfer. The cells that are bound to the membrane are then provided a serial dilution of a specificity exchanger (e.g., 500 ng, 1 μg, 5 μg, 10 μg, 25 μg, and 50 μg of the specificity exchanger in a total volume of 200 μl of PBS). Antigen/antibody specificity exchangers that comprise a specificity domain that binds to a protein present on the bacteria (e.g., Clf) can be evaluated in this manner, for example. Ligand/receptor specificity exchangers having a specificity domain comprising a ligand for a receptor present on the bacteria (e.g., Clf) can also be evaluated using this approach.

In one experiment, for example, the ligand/receptor specificity exchangers listed in TABLES XIII or XIV are used. The diluted ligand/receptor specificity exchangers are then incubated on the membranes for 60 minutes. Subsequently, the non-bound ligand/receptor specificity exchangers are removed and the membrane is washed with PBS (e.g., 3 washes with 2 ml of PBS per wash). Next, a 1:100–1:1000 dilution of a primary antibody that interacts with the antigenic domain of the particular ligand/receptor specificity exchanger (e.g., mAb for herpes simplex virus gG2 protein for some of the specificity exchangers) is provided and the binding reaction is allowed to occur for 60 minutes. Again, the membrane is washed with PBS (e.g., 3 washes with 2 ml of PBS per wash) to remove unbound primary antibody. Appropriate controls include the membrane itself, bacteria on the membrane without a ligand/receptor specificity exchanger, and bacteria on the membrane with ligand/receptor specificity exchanger but no primary antibody.

To detect the amount of ligand/receptor specificity exchanger bound to the bacteria on the membrane, a secondary antibody (e.g., rabbit anti-mouse IgG (Sigma)) and a tertiary antibody (e.g., a peroxidase labeled goat anti-rabbit IgG (Sigma)) are used. Of course, a labeled secondary antibody that interacts with the primary antibody can be used as well. As above, the secondary antibody is contacted with the membrane for 60 minutes and the non-bound secondary antibody is washed from the membrane with PBS (e.g., 3 washes with 2 ml of PBS per wash). Then, the tertiary antibody is contacted with the membrane for 60 minutes and the non-bound tertiary antibody is washed from the membrane with PBS (e.g., 3 washes with 2 ml of PBS per wash). The bound tertiary antibody can be detected by incubating the membrane with dinitro-phenylene-diamine (Sigma).

Another approach involves the use of an immobilized ligand/receptor specificity exchanger. Accordingly, primary antibody (e.g., mAb for herpes simplex virus gG2 protein for some of the specificity exchangers) is bound to a petri dish. Once the primary antibody is bound, various dilutions of a ligand/receptor specificity exchanger (e.g., a ligand/receptor specificity exchanger provided in TABLES XIII or XIV) are added to the coated dish. The ligand/receptor specificity exchanger is allowed to associate with the primary antibody for 60 minutes and the non-bound ligand/receptor specificity exchanger is washed away (e.g., three washes with 2 ml of PBS). Appropriate controls include petri dishes without primary antibody or ligand/receptor specificity exchanger.

Subsequently, a turbid solution of bacteria (e.g., *Staphylococcus*) are added to the petri dishes and the bacteria are allowed to interact with the immobilized ligand/receptor specificity exchanger for 60 minutes. The non-bound bacteria are then removed by washing with PBS (e.g., 3 washes with 2 ml of PBS). Next, growth media (e.g., LB broth) is added to the petri dish and the culture is incubated overnight. Alternatively, LB agar is added to the petri dish and the culture is incubated overnight. An interaction between the ligand/receptor specificity exchanger and the bacteria can be observed visually (e.g., turbid growth media, which can be quantified using spectrophotometry or an analysis of the appearance of colonies on the agar).

By modifying the approaches described above, one of skill in the art can evaluate the ability of a specificity exchanger to interact with a virus. For example, soluble fragments of T4 glycoprotein have been shown to interact with a human immunodeficiency virus (HIV) envelope glycoprotein. (See e.g., U.S. Pat. No. 6,093,539, herein expressly incorporated by reference in its entirety). Ligand/receptor specificity exchangers having a specificity domain comprising a fragment of T4 glycoprotein that interacts with HIV envelope glycoprotein (e.g., amino acids 1–419 of the T4 glycoprotein sequence provided in U.S. Pat. No. 6,093,539 or a portion thereof) can be made by synthesizing a fusion protein having the specificity domain joined to an antigenic domain. Although peptide chemistry can be used to make the ligand/receptor specificity exchanger, it is preferred that an expression construct having the fragment of T4 glycoprotein joined to an antigenic domain is made and transfected into a suitable cell. The expression and purification strategies described in U.S. Pat. No. 6,093,539 and above can also be employed.

Once the ligand/receptor specificity exchanger has been constructed a filter binding assay is performed. Accordingly, serial ten-fold dilutions of HIV inoculum are applied to a membrane (e.g. nitrocellulose or nylon) in a dot blot apparatus under constant vacuum. Then serial ten fold dilutions of the ligand/receptor specificity exchanger are applied to the bound HIV particles. The ligand/receptor specificity exchanger is contacted with the particles for 60 minutes before applying vacuum and washing with PBS (e.g., 3 washes with 2 ml of PBS per wash)). Once the non-bound ligand/receptor specificity exchanger is removed, ten fold serial dilutions of the primary antibody, which binds to the antigenic domain, are added to the samples and the binding reaction is allowed to occur for 60 minutes. Then a vacuum is applied and the non-bound primary antibody is washed with PBS (e.g., 3 washes with 2 ml of PBS per wash)). The detection of the bound primary antibody can be accomplished, as described above.

The ability of a specificity exchanger to interact with a virus can also be evaluated in a sandwich-type assay. Accordingly, a primary antibody that interacts with the antigenic domain of the specificity exchanger is immobilized in micro titer wells and serial dilutions of specificity exchanger are added to the primary antibody so as to create a primary antibody/specificity exchanger complex, as described above. Next, ten fold serial dilutions of HIV inoculum are added and the binding reaction is allowed to occur for 60 minutes. Non-bound HIV particles are removed by successive washes in PBS. Detection of the bound HIV particles can be accomplished using a radiolabeled anti-HIV antibody (e.g., antibody obtained from sera from a person suffering with HIV infection).

While the examples above describe cell-based assays using bacteria and a virus, modifications of these approaches can be made to study the interaction of specificity exchangers with mammalian cells. For example, the ability of a ligand/receptor specificity exchanger to interact with an integrin receptor present on a cancer cell can be determined as follows. Melanoma cells that express an $\alpha_v\beta_3$ receptor (e.g., M21 human melanoma cells) bind fibrinogen and this interaction can be blocked by administering an RGD containing peptide (See e.g., Katada et al., *J. Biol. Chem.* 272: 7720 (1997) and Felding-Habermann et al., *J. Biol. Chem.* 271:5892–5900 (1996); both references herein expressly incorporated by reference in their entireties). Similarly, many other types of cancer cells express integrins that interact with RGD peptides. By one approach, cancer cells that expresses an RGD-responsive integrin (e.g., M21 human melanoma cells) are cultured to confluency. M21 cells can be grown in DMEM media with 10% fetal bovine serum, 20 mM Hepes, and 1 mM pyruvate.

Preferably, the cells are stained with hydroethidine (Polysciences, Inc., Warrington, Pa.) at 20 $\mu$g/ml final concentration ($2\times10^6$ cells/ml) for 30 min at 37° C. and then washed twice to remove excess dye. Hydroethidine intercalates into the DNA resulting in a red fluorescent labeling of the cells and does not impair the cell's adhesive functions. The staining provides a way to quantify the binding of a ligand/receptor specificity exchanger to the cells. That is, the total number of hydroethidine stained cells can be compared to the number of cells bound to a fluorescently labeled primary antibody/specificity exchanger complex so as to determine the binding efficiency.

Accordingly, the stained cells are incubated with various dilutions of a ligand/receptor specificity exchanger comprising a RGD sequence (e.g., GRGDSPHRGGPEE (SEQ. ID No. 197) or WSRGDWHRGGPEE (SEQ. ID No. 198)). After a 60-minute incubation, the non-bound ligand/receptor specificity exchanger is removed by several washes in DMEM media with 10% fetal bovine serum, 20 mM Hepes, and 1 mM pyruvate (e.g., 3 washes of 5 ml of media). Next, a 1:100–1:1000 dilution of a primary antibody that interacts with the antigenic domain of the ligand/receptor specificity exchanger (e.g., mAb for herpes simplex virus gG2 protein) is provided and the binding reaction is allowed to occur for 60 minutes. Subsequently, several washes in media are performed to remove any non-bound primary antibody. Appropriate controls include stained cells without ligand/receptor specificity exchanger or stained cells without primary antibody.

Following binding of the primary antibody, a goat anti-mouse FITC labeled antibody (1:100 dilution) (Sigma) is added and binding is allowed to occur for 60 minutes. Again, several media washes are made to remove any non-bound secondary antibody. Analysis is made by flow cytometry with filter settings at 543/590 nm for hydroethidine and 495/525 nm for fluorescin. One will observe an appreciable binding of primary antibody to the ligand/receptor specificity exchanger/cell complex, which will demonstrate that the ligand/receptor specificity exchanger will have an effect on the cell. It should be emphasized that modifications of the approach described above can be easily made to accommodate the evaluation of an antigen/antibody specificity exchanger.

The next example describes experiments that verified that ligand/receptor specificity exchangers efficiently bind to pathogens in culture and redirect antibodies that are specific for the antigenic domains of the ligand/receptor specificity domains to the pathogen.

EXAMPLE 10

A ligand/receptor specificity exchanger comprising a fragment of fibrinogen (specificity domain) joined to a peptide obtained from the hepatitis B virus (antigenic domain) was found to bind to adhesion receptors present on a pathogen in culture (Murine myeloma cells (SP2/0 cells)). A ligand/receptor specificity exchanger having the sequence RGDSAATPPAYR (SEQ ID No. 199) was manufactured using standard techniques in peptide synthesis using fmoc chemistry (Syro, MultiSynTech, Germany). This peptide has a specificity domain that binds adhesion receptors on a pathogen, a spacer (the AA), and an antigenic domain that has an epitope recognized by the monoclonal antibody 57/8, an epitope present on the hepatitis B virus e antigen (HBeAg).

Murine myeloma cells (SP2/0 cells) were washed in serum free media and were incubated with the ligand/receptor specificity exchanger or a control peptide derived from hepatitis C virus (HCV) NS3 domain at a concentration of 50 $\mu$g/ml. The cells were then washed and the amount of surface bound peptide was detected by labeling the cells with the the anti-HBV (57/8) antibody. Surface bound antibody was indicated by an FITC labelled anti-mouse IgG conjugate diluted $\frac{1}{500}$ and the level of surface staining was determined by fluorescent microscopy.

Microscopy revealed that cells incubated with the control peptide did not show significant staining, whereas, cells incubated with the ligand/receptor specificity exchanger showed significant surface staining consistent with the location of surface expressed adhesion receptors. These experiments verified that ligand/receptor specificity exchangers comprising fragments of fibrinogen effectively bound adhesion recpetors on a pathogen (a myeloma cell) and redirected anti-HBV antibodies to the tumor cells. It should be emphasized that modifications of the approach described above can be easily made to accommodate the evaluation of an antigen/antibody specificity exchanger. The next section describes characterization assays that are performed in animals.

In Vivo Characterization Assays

Characterization assays also include experiments that evaluate specificity exchangers in vivo. There are many animal models that are suitable for evaluating the ability of a a specificity exchanger to inhibit pathogenic infection. Mice are preferred because they are easy to maintain and are susceptible to bacterial infection, viral infection, and cancer. Chimpanzees are also preferred because of their close genetic relationship to humans. The next example provides one in vivo approach to evaluate the ability of a ligand specificity exchanger to bind to a pathogen, redirect antibodies specific for the antigenic domain of the ligand/receptor specificity exchanger, and thereby inhibit the proliferation of the pathogen. It should be emphasized that modifications of the approach described below can be easily made to accommodate the evaluation of an antigen/antibody specificity exchanger.

EXAMPLE 11

To test the ability of a ligand/receptor specificity exchanger to treat a bacterial infection in mice, the following characterization assay can be performed. Several female CF-1 outbred mice (Charles Rivers Laboratories) of approximately 8 weeks of age and 25 gram body mass are inoculated intraperitoneally with overnight cultures of Staphylococcus aureus. Blood samples are drawn from the mice and tests are conducted to verify that Staphylococcus aureus is present in the subjects.

The infected mice are injected with a suitable amount of a ligand specificity exchanger that interacts with the Clf receptor (e.g., a ligand/receptor specificity exchanger comprising a fragment of fibrinogen). A small sample (e.g. 0.5 mL) of human serum that contains antibodies specific for the antigenic domain is also injected into the infected mice. For various time points after the injection of the human serum for up to two weeks, the mice are monitored for the presence and prevalence of Staphylococcus aureus. The progress or decline in Staphylococcus aureus infection is plotted. The data will show that the ligand/receptor specificity exchanger efficiently inhibited the proliferation of Staphylococcus aureus.

Another approach to evaluate the efficacy of a ligand/receptor specificity exchanger in mice is provided in the next example. It should be emphasized that modifications of the approach described below can be easily made to accommodate the evaluation of an antigen/antibody specificity exchanger.

EXAMPLE 12

To test the ability of a ligand/receptor specificity exchanger to treat a bacterial infection the following characterization assay can be performed. Several female CF-1 outbred mice (Charles Rivers Laboratories) of approximately 8 weeks of age and 25 gram body mass are vaccinated with the antigenic domains of the ligand/receptor specificity exchangers to be tested. Preferably, the antigenic domains are coupled to a carrier and are administered with an adjuvant. For example, the antigenic domains can be fused to keyhole limpet hemocyanin or bovine serum albumin, which act as both a carrier and adjuvant or an adjuvant such as Freund's adjuvant, aluminum hydroxide, or lysolecithin can be used. Once a high titer of antibody to the antigenic domains can be verified by, for example, immunodiffusion or EIA, the immunized mice are inoculated intraperitoneally with overnight cultures of Staphylococcus aureus NTCC 10649. The inoculums are adjusted to yield approximately 100×LD$_{50}$ or log 6.6 for S. aureus.

Serial dilutions of ligand/receptor specificity exchangers (e.g., the ligand/receptor specificity exchangers provide in Table IV) are formulated in sterile water for injection and are administered by the subcutaneous (SC) or oral (PO) route at one and five hours post infection. Concurrently with each trial, the challenge LD$_{50}$ is validated by inoculation of untreated mice with log dilutions of the bacterial inoculum. Preferably, a five log dilution range of the bacterial challenges is inoculated into five groups of ten mice each (ten mice per log dilution). A mortality rate of 100% will be produced in all groups of untreated mice at the 100×LD$_{50}$ challenge inoculum. Mice are monitored daily for mortality for seven days. The mean effective dose to protect 50% of the mice (ED$_{50}$) can be calculated from cumulative mortality by logarithmic-probit analysis of a plotted curve of survival versus dosage as described in *Antimicrob. Agents Chemother.* 31: 1768–1774 and *Proc. Soc. Exp. Biol. Med.* 1994, 57, 261–264, each of which are hereby expressly incorporated by reference in their entireties. As one of skill in the art will appreciate, similar approaches can be used to test the ability of ligand/receptor specificity exchangers to inhibit viral infection and cancer.

The specificity exchangers described herein can be formulated in pharmaceuticals and administered to subjects in need of an agent that inhibits the proliferation of a pathogen. The section below describes several pharmaceuticals comprising specificity exchangers that interact with a receptor on a pathogen. The following section describes the preparation of pharmaceuticals comprising a specificity exchanger.

Pharmaceuticals Comprising a Specificity Exchanger

The specificity exchangers described herein are suitable for incorporation into pharmaceuticals for administration to subjects in need of a compound that treats or prevents infection by a pathogen. In preferred embodiments, specificity exchangers are incorporated into pharmaceuticals, as active ingredients for administration to subjects in need of compounds that treat or prevent infection by a pathogen or cancer in animals, including humans. These pharmacologically active compounds can be processed in accordance with conventional methods of galenic pharmacy to produce medicinal agents for administration to mammals including humans. In some embodiments, these pharmaceuticals can contain excipients, binders, emulsifiers, carriers, and other auxiliary agents in addition to the specificity exchanger. In other embodiments, the active ingredients can be incorporated into a pharmaceutical product with and without modification.

Further, the manufacture of pharmaceuticals or therapeutic agents that deliver the pharmacologically active compounds of this invention by several routes are aspects of the present invention. For example, and not by way of limitation, DNA, RNA, and viral vectors having sequences encoding a specificity exchanger that interacts with a receptor or other antigen on a pathogen are used with embodiments of the invention. Nucleic acids encoding a specificity exchanger can be administered alone or in combination with other active ingredients.

The specificity exchangers described herein can be employed in admixture with conventional excipients, i.e., pharmaceutically acceptable organic or inorganic carrier substances suitable for parenteral, enteral (e.g., oral) or topical application that do not deleteriously react with the pharmacologically active ingredients described herein. Suitable pharmaceutically acceptable carriers include, but are not limited to, water, salt solutions, alcohols, gum arabic, vegetable oils, benzyl alcohols, polyethylene glycols, gelatine, carbohydrates such as lactose, amylose or starch, magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, etc. Many more vehicles that can be used are described in *Remmington's Pharmaceutical Sciences*, 15th Edition, Easton:Mack Publishing Company, pages 1405–1412 and 1461–1487(1975) and The National *Formulary* XIV, 14th Edition, Washington, American Pharmaceutical Association (1975), herein incorporated by reference. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like so long as the auxiliary agents does not deleteriously react with the specificity exchangers.

The effective dosage and method of administration of a specificity exchanger provided in a pharmaceutical, therapeutic protocol, or applied to a medical device varies depending on the intended use, the patient, and the frequency of administration. Therapeutic efficacy and toxicity of such compounds can be determined by standard pharmaceutical procedures in cell cultures or experimental animals, e.g., $ED_{50}$ (the dose therapeutically effective in 50% of the population). For example, the effective dose of a specificity exchanger can be evaluated using the characterization assays described above. The data obtained from these assays is then used in formulating a range of dosage for use with other organisms, including humans. The dosage of such compounds lies preferably within a range of circulating concentrations that include the $ED_{50}$ with no toxicity. The dosage varies within this range depending upon type of specificity exchanger, the dosage form employed, sensitivity of the organism, and the route of administration.

Normal dosage amounts of a specificity exchanger can vary from approximately 1 to 100,000 micrograms, up to a total dose of about 10 grams, depending upon the route of administration. Desirable dosages include about 250 mg–1 mg, about 50 mg–200 mg, and about 250 mg–500 mg.

In some embodiments, the dose of a specificity exchanger preferably produces a tissue or blood concentration or both from approximately 0.1 $\mu$M to 500 mM. Desirable doses produce a tissue or blood concentration or both of about 1 to 800 $\mu$M. Preferable doses produce a tissue or blood concentration of greater than about 10 $\mu$M to about 500 $\mu$M. Although doses that produce a tissue concentration of greater than 800 $\mu$M are not preferred, they can be used. A constant infusion of a specificity exchanger can also be provided so as to maintain a stable concentration in the tissues as measured by blood levels.

The exact dosage is chosen by the individual physician in view of the patient to be treated. Dosage and administration are adjusted to provide sufficient levels of the active moiety or to maintain the desired effect. Additional factors that can be taken into account include the severity of the disease, age of the organism being treated, and weight or size of the organism; diet, time and frequency of administration, drug combination(s), reaction sensitivities, and tolerance/response to therapy. Short acting pharmaceutical compositions are administered daily or more frequently whereas long acting pharmaceutical compositions are administered every 2 or more days, once a week, or once every two weeks or even less frequently.

Routes of administration of the pharmaceuticals include, but are not limited to, topical, transdermal, parenteral, gastrointestinal, transbronchial, and transalveolar. Transdermal administration is accomplished by application of a cream, rinse, gel, etc. capable of allowing the specificity exchangers to penetrate the skin. Parenteral routes of administration include, but are not limited to, electrical or direct injection such as direct injection into a central venous line, intravenous, intramuscular, intraperitoneal, intradermal, or subcutaneous injection. Gastrointestinal routes of administration include, but are not limited to, ingestion and rectal. Transbronchial and transalveolar routes of administration include, but are not limited to, inhalation, either via the mouth or intranasally.

Compositions having the specificity exchangers that are suitable for transdermal or topical administration include, but are not limited to, pharmaceutically acceptable suspensions, oils, creams, and ointments applied directly to the skin or incorporated into a protective carrier such as a transdermal device ("transdermal patch"). Examples of suitable creams, ointments, etc. can be found, for instance, in the Physician's Desk Reference. Examples of suitable transdermal devices are described, for instance, in U.S. Pat. No. 4,818,540 issued Apr. 4, 1989 to Chinen, et al., herein expressly incorporated by reference in its entirety.

Compositions having the specificity exchangers that are suitable for parenteral administration include, but are not limited to, pharmaceutically acceptable sterile isotonic solutions. Such solutions include, but are not limited to, saline and phosphate buffered saline for injection into a central venous line, intravenous, intramuscular, intraperitoneal, intradermal, or subcutaneous injection.

Compositions having the specificity exchangers that are suitable for transbronchial and transalveolar administration include, but are not limited to, various types of aerosols for inhalation. Devices suitable for transbronchial and transalveolar administration of these are also embodiments. Such devices include, but are not limited to, atomizers and vaporizers. Many forms of currently available atomizers and vaporizers can be readily adapted to deliver compositions having the specificity exchangers described herein.

Compositions having the specificity exchangers that are suitable for gastrointestinal administration include, but not limited to, pharmaceutically acceptable powders, pills or liquids for ingestion and suppositories for rectal administration. Due to the ease of use, gastrointestinal administration, particularly oral, is a preferred embodiment. Once the pharmaceutical comprising the specificity exchanger has been obtained, it can be administered to an organism in need to treat or prevent pathogenic infection.

Aspects of the invention also include a coating for medical equipment to prevent infection or the spread of disease. The term "medical equipment" is to be construed broadly and includes for example prosthetics, implants, and instruments. Coatings suitable for use on medical devices can be provided by a gel or powder containing the specificity exchanger or by a polymeric coating into which a specificity exchanger is suspended. Suitable polymeric materials for coatings of devices are those that are physiologically acceptable and through which a therapeutically effective amount of the specificity exchanger can diffuse. Suitable polymers include, but are not limited to, polyurethane, polymethacrylate, polyamide, polyester, polyethylene, polypropylene, polystyrene, polytetrafluoroethylene, polyvinylchloride, cellulose acetate, silicone elastomers, collagen, silk, etc. Such coatings are described, for instance, in U.S. Pat. No. 4,612,337, herein expressly incorporated by reference in its entirety. The section below describes methods of treating and preventing disease using the specificity exchangers described herein.

Methods of Treatment and Prevention of Disease Using Specificity Exchangers

Several embodiments also concern approaches to use the specificity exchangers to treat or prevent proliferation of a pathogen. Some methods involve providing a specificity exchanger to a subject in need of treatment and/or prevention of bacterial infection, fungal infection, viral infection, and cancer. For example, pharmaceuticals comprising a specificity exchanger can be provided to a subject in need to treat and/or prevent infection by a pathogen that has a receptor or an antigen. Such subjects in need can include individuals at risk of contacting a pathogen or individuals who are already infected by a pathogen. These individuals can be identified by standard clinical or diagnostic techniques.

By one approach, for example, a subject suffering from a bacterial infection is identified as a subject in need of an agent that inhibits proliferation of a pathogen. This subject is then provided a therapeutically effective amount of a specificity exchanger. The specificity exchanger used in this method comprises a specificity domain that interacts with a receptor (e.g., extracellular fibrinogen binding protein (Efb), collagen binding protein, vitronectin binding protein, laminin binding protein, plasminogen binding protein, thrombospondin binding protein, clumping factor A (ClfA), clumping factor B (ClfB), fibronectin binding protein, coagulase, and extracellular adherence protein) or another antigen present on the bacteria. The specificity exchanger also comprises an antigenic domain that has peptide or an epitope obtained from a pathogen or toxin, preferably, a peptide or an epitope that is recognized by high titer antibodies that are already present in the subject in need. It may also be desired to screen the subject in need for the presence of high titer antibodies that recognize the antigenic domain prior to providing the subject with the specificity exchanger. This screening can be accomplished by EIA or ELISA using immobilized antigenic domain or specificity exchanger, as described above.

Similarly, a subject in need of an agent that inhibits viral infection can be provided a specificity exchanger that recognizes a receptor or antigen present on the particular etiologic agent. Accordingly, a subject in need of an agent that inhibits viral infection is identified by standard clinical or diagnostic procedures. Next, the subject in need is provided a therapeutically effective amount of a specificity exchanger that interacts with the receptor or another antigen present on the type of virus infecting the individual. As above, it may be desired to determine whether the subject has a sufficient titer of antibody to interact with the antigenic domain of the specificity exchanger prior to providing the specificity exchanger.

In the same vein, a subject in need of an agent that inhibits the proliferation of cancer can be provided a specificity exchanger that interacts with a receptor or antigen present on the cancer cell. For example, a subject in need of an agent that inhibits proliferation of cancer is identified by standard clinical or diagnostic procedures; then the subject in need is provided a therapeutically effective amount of a specificity exchanger that interacts with a receptor present on the cancer cells infecting the subject. As noted above, it may be desired to determine whether the subject has a sufficient titer of antibody to interact with the antigenic domain of the specificity exchanger prior to providing the specificity exchanger.

Other embodiments include methods of treating a disease or disorder associated with a known antigen or receptor in an individual in need of an increased number of antigen-specific antibodies. Methods can include providing to said individual, a sufficient amount of a tailor-made specificity exchanger that binds to the known antigen or receptor and certain antibodies known to exist in the individual. An individual in need of an increased number of antigen-specific antibodies against a known antigen or receptor, which causes a disease or disorder in said individual, may be one who will benefit from getting a rapid increase in the number of such antigen-specific antibodies, or who even lacks or has insufficient ability to elicit antibodies against said known antigen. The individual may be a human or non-human mammal.

In certain embodiments, tailor-made specificity exchangers are designed so that certain antibodies existing in the patient in question, (e.g. antibodies against viral proteins, such as antibodies against poliovirus, antibodies against virus causing measles, antibodies against hepatitis B virus, antibodies against hepatitis C virus, antibodies against HIV- 1, whether induced by natural infection or vaccination) bind to the amino-acid sequence of the antigenic domain and the amino-acid sequence of the specificity domain binds to a known antigen or receptor of a pathogen causing a disease or disorder in said patient (e.g. HIV). Thus, existing antibodies in-said patent are redirected to said known antigen or receptor (against which said patient e.g. lacks or has insufficient amount of desired antibodies). A specific example of an specificity exchanger is a peptide which binds to antibodies against poliovirus and also binds specifically to HIV virus. Thus, already high titres in a patient of antibodies against poliovirus may thus be used to fight HIV infection in said patient.

Specificity exchangers described herein can also be provided to subjects as a prophylactic to prevent the onset of disease. Virtually anyone can be provided a specificity exchanger described herein for prophylactic purposes, (e.g., to prevent a bacterial infection, viral infection, or cancer). It is desired, however, that subjects at a high risk of contracting a particular disease are identified and provided a specificity exchanger. Subjects at high risk of contracting a disease include individuals with a family history of disease, the elderly or the young, or individuals that come in frequent contact with a pathogen (e.g., health care practitioners). Accordingly, subjects at risk of becoming infected by a pathogen are identified and then are provided a prophylactically effective amount of specificity exchanger.

One prophylactic application for the specificity exchangers described herein concerns coating or cross-linking the specificity exchanger to a medical device or implant. Implantable medical devices tend to serve as foci for infection by a number of bacterial species. Such device-associated infections are promoted by the tendency of these organisms to adhere to and colonize the surface of the device. Consequently, there is a considerable need to develop surfaces that are less prone to promote the adverse biological reactions that typically accompany the implantation of a medical device.

By one approach, the medical device is coated in a solution of containing a specificity exchanger. Prior to implantation, medical devices (e.g., a prosthetic valve) can be stored in a solution of specificity exchangers, for example. Medical devices can also be coated in a powder or gel having a specificity exchanger. For example, gloves, condoms, and intrauterine devices can be coated in a powder or gel that contains a specificity exchanger that interacts with a bacterial or viral receptor. Once implanted in the body, these specificity exchangers provide a prophylactic barrier to infection by a pathogen.

In some embodiments, the specificity exchanger is immobilized to the medical device. As described above, the medical device is a support to which a specificity exchanger can be attached. Immobilization may occur by hydrophobic interaction between the specificity exchanger and the medical device but a preferable way to immobilize a specificity exchanger to a medical device involves covalent attachment. For example, medical devices can be manufactured with a reactive group that interacts with a reactive group present on the specificity exchanger.

By one approach, a periodate is combined with a specificity exchanger comprising a 2-aminoalcohol moiety to form an aldehyde-functional exchanger in an aqueous solution having a pH between about 4 and about 9 and a temperature between about 0 and about 50 degrees Celsius. Next, the aldehyde-functional exchanger is combined with the biomaterial surface of a medical device that comprises a primary amine moiety to immobilize the specificity exchanger on the support surface through an imine moiety. Then, the imine moiety is reacted with a reducing agent to form an immobilized specificity exchanger on the biomaterial surface through a secondary amine linkage. Other approaches for cross-linking molecules to medical devices, (such as described in U.S. Pat. No. 6,017,741, herein expressly incorporated by reference in its entirety); can be modified to immobilize the specificity exchanger described herein. The next section describes the use of specificity exchangers as diagnostic reagents.

Specificity Exchangers as Diagnostic Reagents

Other embodiments concern the use of specificity exchangers as diagnostic reagents. In this context, specificity exchangers can be used to detect the presence or absence of specific antigens or receptors in biological samples (e.g. body fluid or tissue samples). Accordingly, in certain embodiments, these diagnostic specificity exchangers can be used instead of antisera or monoclonal antibodies in in vitro testing systems, such as immunological tests, e.g. Enzyme-Linked Immunosorbent Assay (ELISA), Enzyme Immunoassay (EIA), Western Blot, Radioimmunoassay (RIA) etc. Furthermore, the diagnostic specificity exchangers can be used to investigate the biological properties of biological systems.

Although the invention has been described with reference to embodiments and examples, it should be understood that various modifications can be made without departing from the spirit of the invention. It is important to note that skilled artisans will understand that the protocols and characterization assays described for ligand/receptor specificity exchangers can be similarly performed on antigen/antibody specificity exchangers by substituting known receptors for known antigens. Likewise, skilled artisans will also understand that the protocols and characterization assays described for antigen/antibody specificity exchangers can be similarly performed on ligand/receptor specificity exchangers by substituting known antigens for known receptors. Accordingly, the invention is limited only by the following claims. All references cited herein are hereby expressly incorporated by reference.

What is claimed is:

1. A ligand/receptor specificity exchanger comprising: at least one specificity domain comprising a ligand for a bacterial adhesion receptor; and at least one antigenic domain joined to said specificity domain, wherein said antigenic domain comprises at least 5 and less than 200 consecutive amino acids of a protein from a pathogen or a toxin.

2. The ligand/receptor specificity exchanger of claim 1, wherein said specificity domain comprises at least three consecutive amino acids of fibrinogen.

3. The ligand/receptor specificity exchanger of claim 1, wherein said antigenic domain comprises at least 5 and less than 50 consecutive amino acids of a protein from a pathogen or a toxin.

4. The ligand/receptor specificity exchanger of claim 2, wherein said antigenic domain comprises at least 5 and less than 50 consecutive amino acids of a protein from a pathogen or a toxin.

5. The ligand/receptor specificity exchanger of claim 1, wherein said antigenic domain comprises at least 5 and less than 50 consecutive amino acids of a protein from a virus.

6. The ligand/receptor specificity exchanger of claim 2, wherein said antigenic domain comprises at least 5 and less than 50 consecutive amino acids of a protein from a virus.

7. The ligand/receptor specificity exchanger of claim 5, wherein said antigenic domain comprises at least 5 and less than 50 consecutive amino acids of a protein from a herpes virus.

8. The ligand/receptor specificity exchanger of claim 6, wherein said antigenic domain comprises at least 5 and less than 50 consecutive amino acids of a protein from a herpes virus.

9. The ligand/receptor specificity exchanger of claim 6, comprising a sequence selected from the group consisting of SEQ. ID. No. 159, SEQ. ID. No. 160, SEQ. ID. No. 161, SEQ. ID. No. 162, SEQ. ID. No. 163, SEQ. ID. No. 164, SEQ. ID. No. 165, SEQ. ID. No. 166, SEQ. ID. No. 167, SEQ. ID. No. 168, SEQ. ID. No. 169, SEQ. ID. No. 170, SEQ. ID. No. 171, SEQ. ID. No. 172, SEQ. ID. No. 173, SEQ. ID. No. 174, SEQ. ID. No. 175, SEQ. ID. No. 176, SEQ. ID. No. 177, SEQ. ID. No. 178, SEQ. ID. No. 179, SEQ. ID. No. 180, SEQ. ID. No. 181, SEQ. ID. No. 182, SEQ. ID. No. 183, SEQ. ID. No. 184, SEQ. ID. No. 185, SEQ. ID. No. 186, SEQ. ID. No. 190, and SEQ. ID. No. 191.

10. The ligand/receptor specificity exchanger of claim 9, comprising a sequence selected from the group consisting of SEQ. ID. No. 190 and SEQ. ID. No. 191.

11. The ligand/receptor specificity exchanger of claim 6, consisting of a sequence selected from the group consisting of SEQ. ID. No. 159, SEQ. ID. No. 160, SEQ. ID. No. 161, SEQ. ID. No. 162, SEQ. ID. No. 163, SEQ. ID. No. 164, SEQ. ID. No. 165, SEQ. ID. No. 166, SEQ. ID. No. 167, SEQ. ID. No. 168, SEQ. ID. No. 169, SEQ. ID. No. 170, SEQ. ID. No. 171, SEQ. ID. No. 172, SEQ. ID. No. 173, SEQ. ID. No. 174, SEQ. ID. No. 175, SEQ. ID. No. 176, SEQ. ID. No. 177, SEQ. ID. No. 178, SEQ. ID. No. 179, SEQ. ID. No. 180, SEQ. ID. No. 181, SEQ. ID. No. 182, SEQ. ID. No. 183, SEQ. ID. No. 184, SEQ. ID. No. 185, SEQ. ID. No. 186, SEQ. ID. No. 190, and SEQ. ID. No. 191.

12. The ligand/receptor specificity exchanger of claim 11, consisting of a sequence selected from the group consisting of SEQ. ID. No. 190 and 191.

13. The ligand/receptor specificity exchanger of claim 6, comprising the sequence of SEQ. ID. No. 190.

14. The ligand/receptor specificity exchanger of claim 6, consisting of the sequence of SEQ. ID. No: 190.

15. The ligand/receptor specificity exchanger of claim 1, wherein said specificity domain comprises at least nine consecutive amino acids of fibrinogen.

16. The ligand/receptor specificity exchanger of claim 1, wherein said specificity domain comprises at least fifteen consecutive amino acids of fibrinogen.

17. The ligand/receptor specificity exchanger of claim 1, wherein said specificity domain comprises at least twenty-one consecutive amino acids of fibrinogen.

18. The ligand/receptor specificity exchanger of claim 1, wherein said specificity domain comprises at least twenty-seven consecutive amino acids of fibrinogen.

19. The ligand/receptor specificity exchanger of claim 1, wherein said specificity domain comprises at least thirty consecutive amino acids of fibrinogen.

* * * * *

UNITED STATES PATENT AND TRADEMARK OFFICE
CERTIFICATE OF CORRECTION

PATENT NO.        : 6,933,366 B2
APPLICATION NO. : 10/372735
DATED              : August 23, 2005
INVENTOR(S)       : Matti Sallberg et al.

It is certified that error appears in the above-identified patent and that said Letters Patent is hereby corrected as shown below:

On page 1, at column 2, line 2-3, please delete "lipopolyssaccharide" and insert --lipopolysaccharide--, therefor.
      On page 2, at column 1, line 2, below "WO95/08577" delete "WO 95 29938 11/1995".
      On page 2, at column 1, line 10, please delete "Proten" and insert --Protein--, therefor.
      On page 2, at column 1, line 18, please delete "irus" and insert --virus--, therefore.
      On page 2, at column 2, line 21, please delete "repolication" and insert --replication--, therefor.
      On page 2, at column 2, line 26, please delete "doman" and insert --domain--, therefor.
      On page 2, at column 2, line 44, please delete "an" and insert --a--, therefor.
      On page 3, at column 1, line 19, please delete "Immunobiology" arid insert --Immunology--, therefor.
      On page 3, at column 1, line 32, please delete "Immune" and insert --immune--, therefor.
      On page 3, at column 1, line 52, please delete "Afinity" and insert --Affinity--, therefor.
      On page 3, at column 1, line 59, please delete "invasin" and insert insert --invasion--, therefor.
      On page 3, at column 1, line 60, please delete "thorugh" and insert --through--, therefor.
      On page 3, at column 2, line 23, please delete "aureus" and insert --Aureus--, therefor.
      On page 3, at column 2, line 35, please delete "immunoglobulin" and insert --inmunologlobulin--, therefor.
      On page 3, at column 2, line 35, after "Lambda" please delete "." and insert --,--, therefor.
      On page 3, at column 2, line 42, after "Acid" please delete ".".
      On page 3, at column 2, line 54, after "between" please insert --the--.
      On page 3, at column 2, line 63, please delete "epidermidis" and insert --Epidermidis--, therefor.
      On page 10, line 63, please delete "Specficity" and insert --Specificity--, therefor.
      On page 12, line 6, please delete "an" and insert --a--, therefor.
      On page 18, line 37, please delete "W1 38" and insert --WI38--, therefor.
      On page 24, line 7, in Table VII, after "amount" please delete "V3".
      On page 26, line 47 (approximately), please delete "finoc" and insert --fmoc--, therefor.

UNITED STATES PATENT AND TRADEMARK OFFICE
CERTIFICATE OF CORRECTION

PATENT NO. : 6,933,366 B2
APPLICATION NO. : 10/372735
DATED : August 23, 2005
INVENTOR(S) : Matti Sallberg et al.

It is certified that error appears in the above-identified patent and that said Letters Patent is hereby corrected as shown below:

On page 28, line 30, please delete "CIFA" and insert --CIfA --, therefor.
    On page 29, in Table XIII, line 9 (SEQ. ID. No. 82), please delete "DILHQVENKTSEVKQLIKAIHGGPEE" and insert --DILHQVENKTSEVKQLIKAIHRGGPEE--, therefor.
    On page 29, in Table XIII, line 11 (SEQ. ID. No. 84), please delete "QLTYNIPDESSKPNMIDAATLHRGGPEE" and insert --QLTYNPDESSKPNMIDAATLHRGGPEE--, therefor.
    On page 29, in Table XIII, line 13 (SEQ. ID. No. 86), please delete "KSRIMLEEIMKYEASTILTHDHRGGPEE" and insert --KSRIMLEEIMKYEASILTHDHRGGPEE--, therefor.
    On page 31, in Table XIII, line 4 (SEQ. ID No. 112), please delete "SKASTPNGYDNGTIIWATWKTHRGGPE" and insert --SKASTPNGYDNGIIWATWKTHRGGPEE--, therefor.
    On page 31, in Table XIVI, line 54 (SEQ. ID. No. 177), please delete "PALTAVETGATNPL-HHLGHAR AGR" and inser --PALTAVETGATNPL-HHLGHARQAGR--, therefor.
    On page 33, in Table XV, line 4, after "Cong." Please delete "µ/ml" and insert --µg/ml--, therefor.
    On page 33, line 27, please delete "preformed" and insert --performed--, therefor.
    On page 35, line 54, please delete "wash))" and insert --wash)--, therefor.
    On page 35, line 60, please delete "wash))" and insert --wash)--, therefor.
    On page 37, line 31 (approximately), after "with" please delete "the".
    On page 37, line 32 (approximately), please delete "labelled" and insert --labeled--, therefor.
    On page 37, line 41, please delete "recpetors" and insert --receptors--, therefor.
    On page 37, line 52, before "specificity" please delete "a".
    On page 43, line 9, before "specificity" please delete "an" and insert --a--, therefor.
    On page 61, line 41, before "SEQ" please insert --<210>--.
    On page 61, line 42, before "LENGTH" please insert --<211>--.
    On page 61, line 43, before "TYPE" please insert --<212>--.

UNITED STATES PATENT AND TRADEMARK OFFICE
CERTIFICATE OF CORRECTION

PATENT NO. : 6,933,366 B2
APPLICATION NO. : 10/372735
DATED : August 23, 2005
INVENTOR(S) : Matti Sallberg et al.

It is certified that error appears in the above-identified patent and that said Letters Patent is hereby corrected as shown below:

On page 122, line 24, In Claim 14, please delete "No:" and insert --No.--, therefor.

Signed and Sealed this

Seventh Day of November, 2006

JON W. DUDAS
*Director of the United States Patent and Trademark Office*